(12) United States Patent
McWherter et al.

(10) Patent No.: US 6,660,257 B1
(45) Date of Patent: Dec. 9, 2003

(54) CIRCULAR PERMUTEINS OF FLT3 LIGAND

(75) Inventors: Charles A. McWherter, Wildwood, MO (US); Yiqing Feng, St. Louis, MO (US); John P. Mc Kearn, Glencoe, MO (US); Nicholas R. Staten, St. Louis, MO (US); Philip R. Streeter, Glencoe, MO (US); Susan L. Woulfe, Ballwin, MO (US); Nancy I. Minster, Chesterfield, MO (US); John C. Minnerly, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 636 days.

(21) Appl. No.: 08/955,090

(22) Filed: Oct. 21, 1997

Related U.S. Application Data
(60) Provisional application No. 60/030,094, filed on Oct. 25, 1996.

(51) Int. Cl.$^7$ .......................... A61K 38/19; C07K 14/52
(52) U.S. Cl. ................... 424/85.1; 424/198.1; 530/351; 530/399; 514/2; 514/12
(58) Field of Search ............................... 435/69.5, 69.7, 435/325, 360, 365.1, 252.3, 320.1; 530/350, 351, 399; 536/23.1, 23.4; 935/10, 13; 424/85.1, 192.1, 198.1; 514/2, 12

(56) References Cited

U.S. PATENT DOCUMENTS

| | | |
|---|---|---|
| 5,554,512 A | 9/1996 | Lyman et al. |
| 5,635,599 A | 6/1997 | Pastan et al. |

FOREIGN PATENT DOCUMENTS

| | | |
|---|---|---|
| EP | 0 627 487 A2 | 5/1994 |
| WO | WO94/26891 | 11/1994 |
| WO | WO94/28391 | 12/1994 |
| WO | WO95/24469 | 9/1995 |
| WO | WO95/27732 | 10/1995 |
| WO | WO97/12985 | 4/1997 |

OTHER PUBLICATIONS

M. Kotzmann et al., European Journal of Clinical Investigation, 1996. 26:1175–1181.*

Reeke et al, "Three–Dimensional Structure of Favin: Saccharide Binding–Cyclic Permutation in Leguminous Lectins", Science, Nov. 28, 1986, vol. 234 pp 1108–1111.

Luger et al, "An 8–fold Ba Barrel Protein with Redundant Folding Possibilites", Protein Engineering, Vol 3 pp 249–258 (1990).

Cunningham et al, "Favion versus concanavalin A: Circularly permuted amino acid sequences", Proc. Natl. Acad. Sci. USA, Jul. 1979, vol. 76, No. 7, pp. 3218–3222.

Protasova et al, Circularly permuted dihydrofolate reductase of E.coli has functional activity and a destabilized tertiary structure:, Protein Engineering, 1994, vol. 7, No. 11, pp. 1373–1777.

Zhang et al, "Circular Permutation of T4 Lysozyme", Biochemistry, Vol 32, No. 46, 1993.

Luger et al, "Correct Folding of Circularly Permuted Variants of a Ba Barrel Enzyme in Vivo", Science, Vol 234(1989).

Hahn et al, "Native–like in vivo folding of a circularly permuted jellyroll protein shown by crystal structure analysis", Proc. Natl. Acad. Sci. USA, 1994, vol. 91, pp. 10417–10421.

Lin et al, "Rearranging the domains of pepsinogen", Protein Science, 1995, Vol 4, pp 159–166.

Yang et al, "Aspartate transcarbamoylase containing circularly permuted catalytic polypeptide chains", Proc. Natl. Acad. Sci. USA, 1993, vol. 90, pp. 11980–11984.

Vignai et al, "Circular permutation within the coenzyme binding domain of the tetrameric glyceraldehyde–3–phosphate dehydrogenase from Bacillus stearothermophilus", Protein Science, 1995, Vol 4., pp. 994–1000.

Goldenberg et al, "Circular and Circularly Permuted Forms of Bovine Pancreatic Trypsin Inhibitor", J. Mol. Biol. 1983, vol. 165, pp. 407–413.

Hemperly et al, "Circular permutation of amino acid sequences among legume lectins", TIBS, 1983, pp. 100–102.

Kreitman et al, "Circularly permuted interleukin 4 retains proliferative and binding activity", Cytokine, 1995, vol. 7, No. 4, pp. 311–318.

Li et al, "Degradation of Ornithine Decarboxylase", Mol. and Cel. Biol. 1993, vol. 13, No. 4, pp. 2377–2383.

Ritco et al, "Is the Continuity of the Domains Required for the Correct Folding of a Two–Domain Protein?", Biochemistry, 1995, vol. 34, pp. 16543–16551.

Garrett et al, "Are turns required for the folding of ribonuclease T1?", Protein Science, 1996, Vol 5., pp. 204–211.

Komar et al, "Kinetics of translation" FEBS Letters, 1995 vol. 376, pp. 195–198.

MacGregor et al, "A circularly permuted a–amylase–type", FEBS Letters, 1996, vol. 378, pp. 263–266.

Koebnik et al, "Membrane Assembly of Circulary Permuted Variants", JMB, 1995, vol. 250, pp. 617–626.

Buchwalder et al, "A fully active variant of Dihydrofolate Reductase with a circularly permuted sequence", Biochemistry, 1992, vol. 31, pp. 1621–1630.

Viguera et al, "The order of secondary structure elements", J. Mol. Biol., 1995, vol. 247, pp. 670–681.

(List continued on next page.)

Primary Examiner—Gary Kunz
(74) Attorney, Agent, or Firm—S. Christopher Bauer; Pharmacia Corporation

(57) ABSTRACT

Disclosed are novel flt-3 receptor agonist proteins, DNAs which encode the flt-3 receptor agonist proteins, methods of making the flt-3 receptor agonist proteins and methods of using the flt-3 receptor agonist proteins.

11 Claims, 5 Drawing Sheets

OTHER PUBLICATIONS

Mullins et al. "Transposition of Protein Sequences: Circular Permutation of Ribonuclease T1", J. Am. Chem. Soc., 1994, vol. 116, pp. 5529–5533.

Horlick et al, "Permuteins of interleukin 1B—a simplified approach for the construction of permutated proteins having new termini", Protein Engineering, USA, 1992, vol. 5, pp. 427–431.

Kreitman et al, "A circularly permuted recombinant interleukin 4 toxin with increase activity", Proc. Natl. Acad. Sci. USA, 1994, vol. 91, pp. 6889–6893.

Hannum et al, "Ligand for FLT3/FLK2 receptor tyrosine kinase regulates growth of haematopoietic stem cells and is encoded by variant RNAs", Nature, 1994, vol. 368, pp. 643–648.

Lyman et al, "Cloning of the Human Homologue of the Murine flt3 Ligand: A Growth Factor for Early Hematopoietic Progenitor Cells", The AM. Soc. of Hematology, USA, 1994, pp. 2795–2801.

* cited by examiner

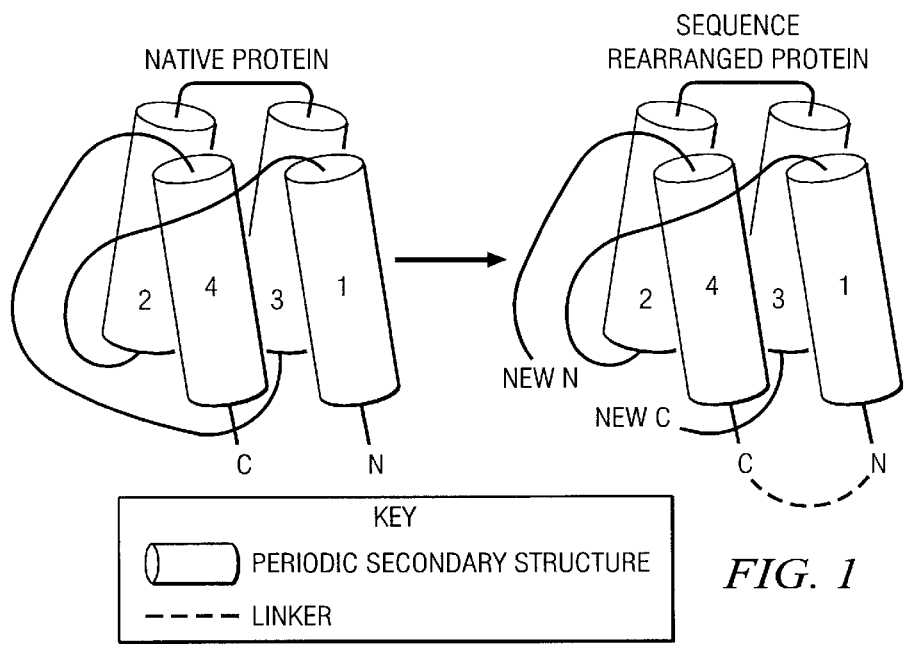
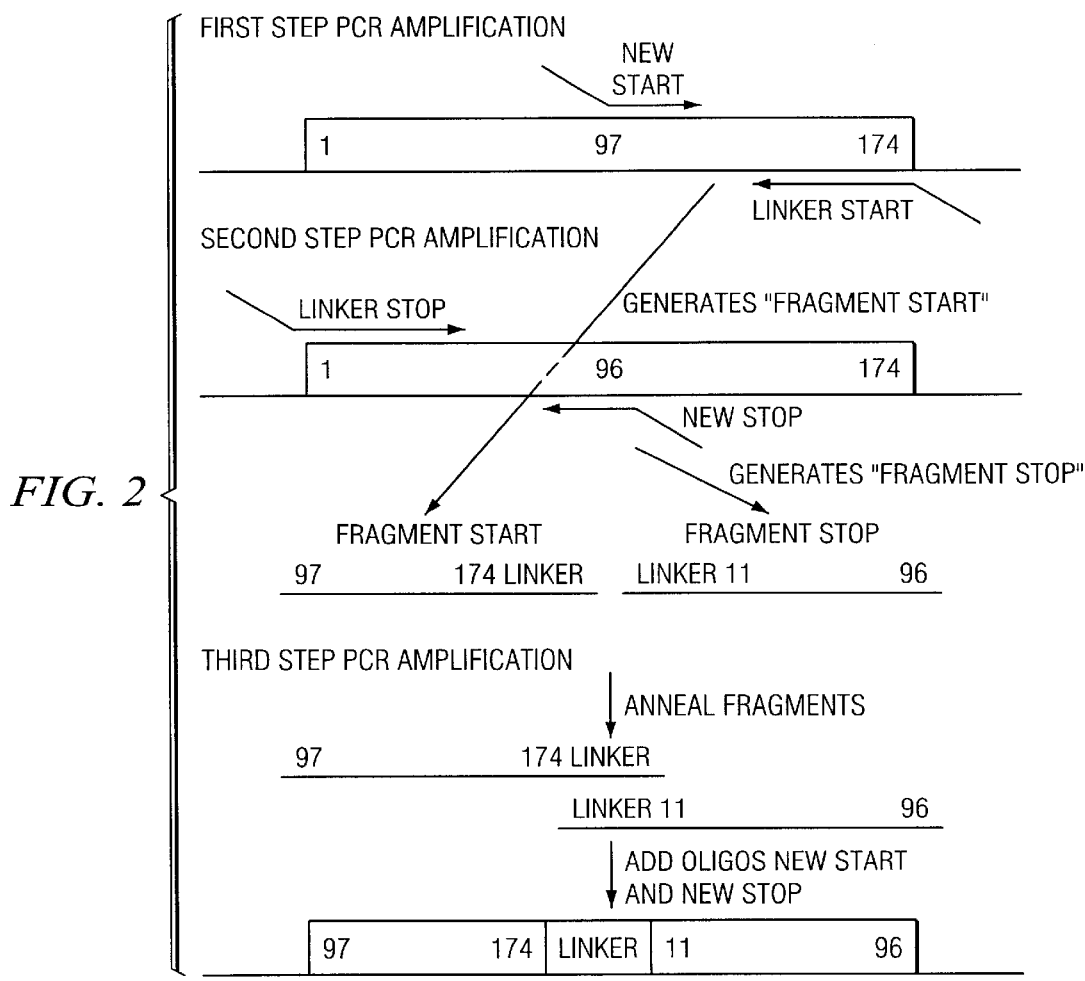

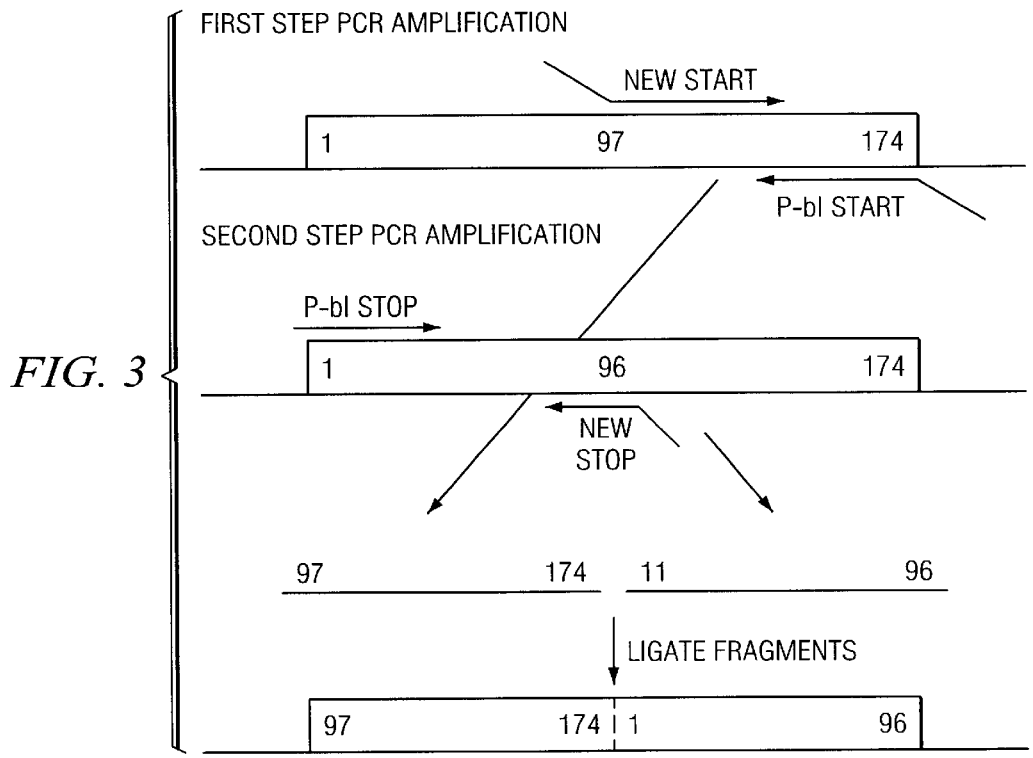
FIG. 3
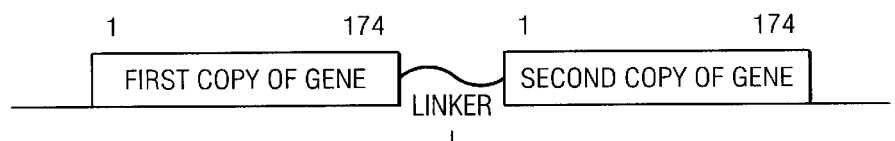
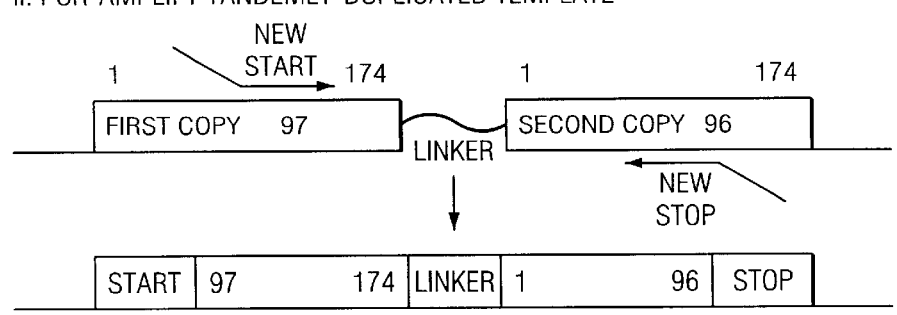
FIG. 4

```
     ACCCAGGACTGCTCCTTCCAACACAGCCCCATCTCCTCCGACTTCGCTGTCAAAATCCGT
  1  ---------+---------+---------+---------+---------+---------+  60
     TGGGTCCTGACGAGGAAGGTTGTGTCGGGGTAGAGGAGGCTGAAGCGACAGTTTTAGGCA

ThrGlnAspCysSerPheGlnHisSerProIleSerSerAspPheAlaValLysIleArg

GAGCTGTCTGACTACCTGCTTCAAGATTACCCAGTCACCGTGGCCTCCAACCTGCAGGAC
  61 ---------+---------+---------+---------+---------+---------+ 120
     CTCGACAGACTGATGGACGAAGTTCTAATGGGTCAGTGGCACCGGAGGTTGGACGTCCTG

GluLeuSerAspTyrLeuLeuGlnAspTyrProValThrValAlaSerAsnLeuGlnAsp

GAGGAGCTCTGCGGGGGCCTCTGGCGGCTGGTCCTGGCACAGCGCTGGATGGAGCGGCTC
 121 ---------+---------+---------+---------+---------+---------+ 180
     CTCCTCGAGACGCCCCCGGAGACCGCCGACCAGGACCGTGTCGCGACCTACCTCGCCGAG

GluGluLeuCysGlyGlyLeuTrpArgLeuValLeuAlaGlnArgTrpMetGluArgLeu

AAGACTGTCGCTGGGTCCAAGATGCAAGGCTTGCTGGAGCGCGTGAACACGGAGATACAC
 181 ---------+---------+---------+---------+---------+---------+ 240
     TTCTGACAGCGACCCAGGTTCTACGTTCCGAACGACCTCGCGCACTTGTGCCTCTATGTG

LysThrValAlaGlySerLysMetGlnGlyLeuLeuGluArgValAsnThrGluIleHis

TTTGTCACCAAATGTGCCTTTCAGCCCCCCCCCAGCTGTCTTCGCTTCGTCCAGACCAAC
 241 ---------+---------+---------+---------+---------+---------+ 300
     AAACAGTGGTTTACACGGAAAGTCGGGGGGGGGTCGACAGAAGCGAAGCAGGTCTGGTTG

PheValThrLysCysAlaPheGlnProProProSerCysLeuArgPheValGlnThrAsn

ATCTCCCGCCTCCTGCAGGAGACCTCCGAGCAGCTGGTGGCGCTGAAGCCCTGGATCACT
 301 ---------+---------+---------+---------+---------+---------+ 360
     TAGAGGGCGGAGGACGTCCTCTGGAGGCTCGTCGACCACCGCGACTTCGGGACCTAGTGA

IleSerArgLeuLeuGlnGluThrSerGluGlnLeuValAlaLeuLysProTrpIleThr

CGCCAGAACTTCTCCCGGTGCCTGGAGCTGCAGTGTCAGCCCGACTCCTCAACCCTGCCA
 361 ---------+---------+---------+---------+---------+---------+ 420
     GCGGTCTTGAAGAGGGCCACGGACCTCGACGTCACAGTCGGGCTGAGGAGTTGGGACGGT

ArgGlnAsnPheSerArgCysLeuGluLeuGlnCysGlnProAspSerSerThrLeuPro

CCCCCATGGAGTCCCCGGCCCCTGGAGGCCACAGCCCCGACAGCCCCGCAGCCCCCTCTG
 421 ---------+---------+---------+---------+---------+---------+ 480
     GGGGGTACCTCAGGGGCCGGGGACCTCCGGTGTCGGGGCTGTCGGGGCGTCGGGGGAGAC

ProProTrpSerProArgProLeuGluAlaThrAlaProThrAlaProGlnProProLeu
```

*FIG. 5a*

```
    CTCCTCCTACTGCTGCTGCCCGTGGGCCTCCTGCTGCTGGCCGCTGCCTGGTGCCTGCAC
481 ---------+---------+---------+---------+---------+---------+ 540
    GAGGAGGATGACGACGACGGGCACCCGGAGGACGACGACCGGCGACGGACCACGGACGTG

LeuLeuLeuLeuLeuLeuProValGlyLeuLeuLeuLeuAlaAlaAlaTrpCysLeuHis

TGGCAGAGGACGCGGCGGAGGACACCCCGCCCTGGGGAGCAGGTGCCCCCCGTCCCCAGT
541 ---------+---------+---------+---------+---------+---------+ 600
    ACCGTCTCCTGCGCCGCCTCCTGTGGGGCGGGACCCCTCGTCCACGGGGGGCAGGGGTCA

TrpGlnArgThrArgArgArgThrProArgProGlyGluGlnValProProValProSer

CCCCAGGACCTGCTGCTTGTGGAGCACTGA
601 ---------+---------+---------+ 630
    GGGGTCCTGGACGACGAACACCTCGTGACT

ProGlnAspLeuLeuLeuValGluHisEnd
```

*FIG. 5b*

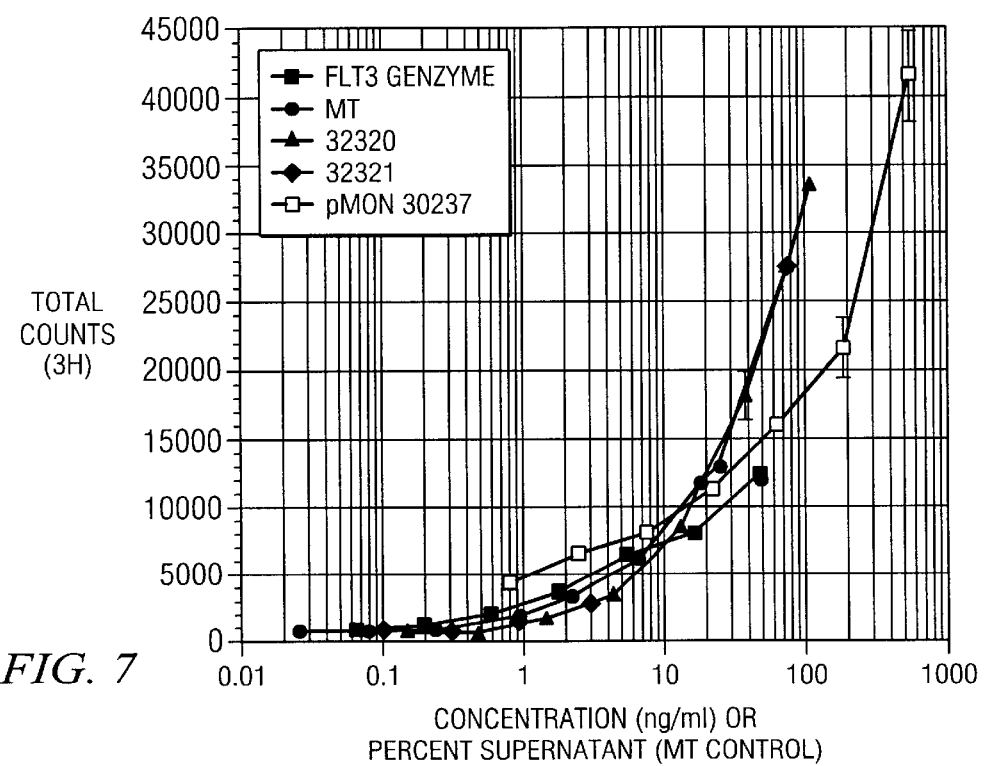

*FIG. 7*

```
    ACCCAGGACTGCTCCTTCCAACACAGCCCCATCTCCTCCGACTTCGCTGTCAAAATCCGT
  1 ---------+---------+---------+---------+---------+---------+ 60
    TGGGTCCTGACGAGGAAGGTTGTGTCGGGGTAGAGGAGGCTGAAGCGACAGTTTTAGGCA

ThrGlnAspCysSerPheGlnHisSerProIleSerSerAspPheAlaValLysIleArg

GAGCTGTCTGACTACCTGCTTCAAGATTACCCAGTCACCGTGGCCTCCAACCTGCAGGAC
 61 ---------+---------+---------+---------+---------+---------+ 120
    CTCGACAGACTGATGGACGAAGTTCTAATGGGTCAGTGGCACCGGAGGTTGGACGTCCTG

GluLeuSerAspTyrLeuLeuGlnAspTyrProValThrValAlaSerAsnLeuGlnAsp

GAGGAGCTCTGCGGGGGCCTCTGGCGGCTGGTCCTGGCACAGCGCTGGATGGAGCGGCTC
121 ---------+---------+---------+---------+---------+---------+ 180
    CTCCTCGAGACGCCCCCGGAGACCGCCGACCAGGACCGTGTCGCGACCTACCTCGCCGAG

GluGluLeuCysGlyGlyLeuTrpArgLeuValLeuAlaGlnArgTrpMetGluArgLeu

AAGACTGTCGCTGGGTCCAAGATGCAAGGCTTGCTGGAGCGCGTGAACACGGAGATACAC
181 ---------+---------+---------+---------+---------+---------+ 240
    TTCTGACAGCGACCCAGGTTCTACGTTCCGAACGACCTCGCGCACTTGTGCCTCTATGTG

LysThrValAlaGlySerLysMetGlnGlyLeuLeuGluArgValAsnThrGluIleHis

TTTGTCACCAAATGTGCCTTTCAGCCCCCCCCCAGCTGTCTTCGCTTCGTCCAGACCAAC
241 ---------+---------+---------+---------+---------+---------+ 300
    AAACAGTGGTTTACACGGAAAGTCGGGGGGGGGTCGACAGAAGCGAAGCAGGTCTGGTTG

PheValThrLysCysAlaPheGlnProProProSerCysLeuArgPheValGlnThrAsn

ATCTCCCGCCTCCTGCAGGAGACCTCCGAGCAGCTGGTGGCGCTGAAGCCCTGGATCACT
301 ---------+---------+---------+---------+---------+---------+ 360
    TAGAGGGCGGAGGACGTCCTCTGGAGGCTCGTCGACCACCGCGACTTCGGGACCTAGTGA

IleSerArgLeuLeuGlnGluThrSerGluGlnLeuValAlaLeuLysProTrpIleThr

CGCCAGAACTTCTCCCGGTGCCTGGAGCTGCAGTGTCAGCCC
361 ---------+---------+---------+---------+-- 402
    GCGGTCTTGAAGAGGGCCACGGACCTCGACGTCACAGTCGGG

ArgGlnAsnPheSerArgCysLeuGluLeuGlnCysGlnPro
```

*FIG. 6*

CIRCULAR PERMUTEINS OF FLT3 LIGAND

The present application claims priority under Title 35, United States Code, §119 of U.S. Provisional application Serial No. 60/030,094, filed Oct. 25, 1996.

FIELD OF THE INVENTION

The present invention relates to human flt3 receptor agonists. These flt3 receptor agonists retain one or more activities of native flt3 ligand and may also show improved hematopoietic cell-stimulating activity and/or an improved activity profile which may include reduction of undesirable biological activities associated with native flt3 ligand and/or have improved physical properties which may include increased solubility, stability and refold efficiency.

BACKGROUND OF THE INVENTION

Colony stimulating factors which stimulate the differentiation and/or proliferation of bone marrow cells have generated much interest because of their therapeutic potential for restoring depressed levels of hematopoietic stem cell-derived cells. Colony stimulating factors in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. Certain factors such as flt3 ligand are able to predominately affect stem cells.

Tyrosine kinase receptors are growth factor receptors that regulate the proliferation and differentiation of a number of cell. Certain tyrosine kinase receptors function within the hematopoietic system. Flt3 ligand (Rosnet et al., *Oncogene*, 6:1641–1650, 1991) and flk-2 (Matthews et al., *Cell*, 65:1143–1152, 1991) are forms of a tyrosine kinase receptor that is related to c-fms and c-kit receptors. The flk-2 and flt3 receptors are similar in amino acid sequence and vary at two amino acid residues in the extracellular domain and diverge in a 31 amino acid segment located near the C-terminus.

flt3 ligand is a hematopoietic growth factor which has the property of being able to regulate the growth and differentiation of hematopoietic progenitor and stem cells. Because of its ability to support the growth and proliferation of progenitor cells, flt3 receptor agonists have potential for therapeutic use in treating hematopoietic disorders such as aplastic anemia and myelodysplastic syndromes. Additionally, flt3 receptor agonists will be useful in restoring hematopoietic cells to normal amounts in those cases where the number of cells has been reduced due to diseases or to therapeutic treatments such as radiation and chemotherapy.

WO 94/28391 discloses the native flt3 ligand protein sequence and a cDNA sequence encoding the flt3 ligand, methods of expressing flt3 ligand in a host cell transfected with the cDNA and methods of treating patients with a hematopoietic disorder using flt3 ligand.

U.S. Pat. No. 5,554,512 is directed to human flt3 ligand as an isolated protein, DNA encoding the flt3 ligand, host cells transfected with cDNAs encoding flt3 ligand and methods for treating patients with flt3 ligand.

WO 94/26891 provides mammalian flt3 ligands, including an isolate that has an insertion of 29 amino acids, and fragments there of.

Rearrangement of Protein Sequences

In evolution, rearrangements of DNA sequences serve an important role in generating a diversity of protein structure and function. Gene duplication and exon shuffling provide an important mechanism to rapidly generate diversity and thereby provide organisms with a competitive advantage, especially since the basal mutation rate is low (Doolittle, *Protein Science* 1:191–200, 1992).

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76:3218–3222, 1979; Teather & Erfle, *J. Bacteriol.* 172: 3837–3841, 1990; Schimming et al., *Eur. J. Biochem.* 204: 13–19, 1992; Yamiuchi and Minamikawa, *FEBS Lett.* 260:127–130, 1991: MacGregor et al., *FEBS Lett.* 378:263–266, 1996). The first in vitro application of this type of rearrangement to proteins was described by Goldenberg and Creighton (*J. Mol. Biol.* 165:407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165:407–413, 1983; Li & Coffino, *Mol. Cell. Biol.* 13:2377–2383, 1993). The proteins examined have represented a broad range of structural classes, including proteins that contain predominantly α-helix (interleukin-4; Kreitman et al., *Cytokine* 7:311–318, 1995), β-sheet (interleukin-1; Horlick et al., *Protein Eng.* 5:427–431, 1992), or mixtures of the two (yeast phosphoribosyl anthranilate isomerase; Luger et al., *Science* 243:206–210, 1989). Broad categories of protein function are represented in these sequence reorganization studies:

| Enzymes | |
|---|---|
| T4 lysozyme | Zhang et al., Biochemistry 32:12311–12318 (1993); Zhang et al., Nature Struct. Biol. 1:434–438 (1995) |
| dihydrofolate reductase | Buchwalder et al., Biochemistry 31:1621–1630 (1994); Protasova et al., Prot. Eng. 7:1373–1377 (1995) |
| ribonuclease T1 | Mullins et al., J. Am. Chem. Soc. 116:5529–5533 (1994); Garrett et al., Protein Science 5:204–211 (1996) |
| Bacillus β-glucanse | Hahn et al., Proc. Natl. Acad. Sci. U.S.A. 91:10417–10421 (1994) |
| aspartate transcarbamoylase | Yang & Schachman, Proc. Natl. Acad. Sci. U.S.A. 90:11980–11984 (1993) |
| phosphoribosyl anthranilate isomerase | Luger et al., Science 243:206–210 (1989); Luger et al., Prot. Eng. 3:249–258 (1990) |
| pepsin/pepsinogen | Lin et al., Protein Science 4:159–166 (1995) |
| glyceraldehyde-3-phosphate dehydrogenase | Vignais et al., Protein Science 4:994–1000 (1995) |
| ornithine | Li & Coffino, Mol. Cell. Biol. |

-continued

| | |
|---|---|
| decarboxylase yeast phosphoglycerate dehydrogenase | 13:2377–2383 (1993) Ritco-Vonsovici et al., Biochemistry 34:16543–16551 (1995) |
| Enzyme Inhibitor | |
| basic pancreatic trypsin inhibitor | Goldenberg & Creighton, J. Mol. Biol. 165:407–413 (1983) |
| Cytokines | |
| interleukin-1β | Horlick et al., Protein Eng. 5:427–431 (1992) |
| interleukin-4 | Kreitman et al., Cytokine 7:311–318 (1995) |
| Tyrosine Kinase Recognition Domain | |
| α-spectrin SH3 domain | Viguera, et al., J. Mol. Biol. 247:670–681 (1995) |
| Transmembrane Protein | |
| omp A | Koebnik & Krämer, J. Mol. Biol. 250:617–626 (1995) |
| Chimeric Protein | |
| interleukin-4-Pseudomonas exotoxin fusion molecule | Kreitman et al., Proc. Natl. Acad. Sci. U.S.A. 91:6889–6893 (1994). |

The results of these studies have been highly variable. In many cases substantially lower activity, solubility or thermodynamic stability were observed (E. coli dihydrofolate reductase, aspartate transcarbamoylase, phosphoribosyl anthranilate isomerase, glyceraldehyde-3-phosphate dehydrogenase, ornithine decarboxylase, omp A, yeast phosphoglycerate dehydrogenase). In other cases, the sequence rearranged protein appeared to have many nearly identical properties as its natural counterpart (basic pancreatic trypsin inhibitor, T4 lysozyme, ribonuclease T1, Bacillus β-glucanase, interleukin-1β, α-spectrin SH3 domain, pepsinogen, interleukin-4). In exceptional cases, an unexpected improvement over some properties of the natural sequence was observed, e.g., the solubility and refolding rate for rearranged α-spectrin SH3 domain sequences, and the receptor affinity and anti-tumor activity of transposed interleukin-4-Pseudomonas exotoxin fusion molecule (Kreitman et al., Proc. Natl. Acad. Sci. U.S.A. 91:6889–6893, 1994; Kreitman et al., Cancer Res. 55:3357–3363, 1995).

The primary motivation for these types of studies has been to study the role of short-range and long-range interactions in protein folding and stability. Sequence rearrangements of this type convert a subset of interactions that are long-range in the original sequence into short-range interactions in the new sequence, and vice versa. The fact that many of these sequence rearrangements are able to attain a conformation with at least some activity is persuasive evidence that protein folding occurs by multiple folding pathways (Viguera, et al., J. Mol. Biol. 247:670–681, 1995). In the case of the SH3 domain of α-spectrin, choosing new termini at locations that corresponded to β-hairpin turns resulted in proteins with slightly less stability, but which were nevertheless able to fold.

The positions of the internal breakpoints used in the studies cited here are found exclusively on the surface of proteins, and are distributed throughout the linear sequence without any obvious bias towards the ends or the middle (the variation in the relative distance from the original N-terminus to the breakpoint is ca. 10 to 80% of the total sequence length). The linkers connecting the original N- and C-termini in these studies have ranged from 0 to 9 residues. In one case (Yang & Schachman, Proc. Natl. Acad. Sci. U.S.A. 90:11980–11984, 1993), a portion of sequence has been deleted from the original C-terminal segment, and the connection made from the truncated C-terminus to the original N-terminus. Flexible hydrophilic residues such as Gly and Ser are frequently used in the linkers. Viguera, et al.(J. Mol. Biol. 247:670–681, 1995) compared joining the original N- and C-termini with 3-or 4-residue linkers; the 3-residue linker was less thermodynamically stable. Protasova et al. (Protein Eng. 7:1373–1377, 1994) used 3- or 5-residue linkers in connecting the original N-termini of E. coli dihydrofolate reductase; only the 3-residue linker produced protein in good yield.

SUMMARY OF THE INVENTION

The modified human flt3 receptor agonists of the present invention can be represented by the Formula:

$$X^1-(L)_a-X^2$$

wherein;

a is 0 or 1;

$X^1$ is a peptide comprising an amino acid sequence corresponding to the sequence of residues n+1 through J;

$X^2$ is a peptide comprising an amino acid sequence corresponding to the sequence of residues 1 through n;

n is an integer ranging from 1 to J-1; and

L is a linker.

In the formula above the constituent amino acids residues of human flt3 ligand are numbered sequentially 1 through J from the amino to the carboxyl terminus. A pair of adjacent amino acids within this protein may be numbered n and n+1 respectively where n is an integer ranging from 1 to J-1. The residue n+1 becomes the new N-terminus of the new flt3 receptor agonist and the residue n becomes the new C-terminus of the new flt3 receptor agonist.

The present invention relates to novel flt3 receptor agonists of the following formula:

```
ThrGlnAspCysSerPheGlnHisSerProIleSerSerAspPheAlaValLysIleArg
                        10                                  20

GluLeuSerAspTyrLeuLeuGlnAspTyrProValThrValAlaSerAsnLeuGlnAsp
                        30                                  40

GluGluLeuCysGlyGlyLeuTrpArgLeuValLeuAlaGlnArgTrpMetGluArgLeu
                        50                                  60
```

```
                              -continued
LysThrValAlaGlySerLysMetGlnGlyLeuLeuGluArgValAsnThrGluIleHis
                    70                                  80

PheValThrLysCysAlaPheGlnProProProSerCysLeuArgPheValGlnThrAsn
                    90                                  100

IleSerArgLeuLeuGlnGluThrSerGluGlnLeuValAlaLeuLysProTrpIleThr
                    110                                 120

ArgGlnAsnPheSerArgCysLeuGluLeuGlnCysGlnProAspSerSerThrLeuPro
                    130                                 140

ProProTrpSerProArgProLeuGluAlaThrAlaProThrAlaProGlnProProLeu
                    150                                 160

LeuLeuLeuLeuLeuLeuProValGlyLeuLeuLeuLeuAlaAlaAlaTrpCysLeuHis
                    170                                 180

TrpGlnArgThrArgArgArgThrProArgProGlyGluGlnValProProValProSer
                    190                                 200

ProGlnAspLeuLeuLeuValGluHis         SEQ ID NO:145
                    209
``` wherein the N-terminus is joined to the C-terminus directly or through a linker capable of joining the N-terminus to the C-terminus and having new C- and N-termini at amino acids;

| | | |
|---|---|---|
| 28–29 | 42–43 | 93–94 |
| 29–30 | 64–65 | 94–95 |
| 30–31 | 65–66 | 95–96 |
| 31–32 | 66–67 | 96–97 |
| 32–33 | 86–87 | 97–98 |
| 34–35 | 87–88 | 98–99 |
| 36–37 | 88–89 | 99–100 |
| 37–38 | 89–90 | 100–101 |
| 38–39 | 90–91 | 101–102 |
| 39–40 | 91–92 | 102–103 |
| 40–41 | 92–93 | respectively; and |
| 41–42 | | | additionally said flt3 receptor agonist polypeptide can be immediately preceded by (methionine$^{-1}$), (alanine$^{-1}$) or (methionine$^{-2}$, alanine$^{-1}$).

A preferred embodiment is human flt3 receptor agonist polypeptide, comprising a modified flt3 ligand amino acid sequence of the Formula:

```
ThrGlnAspCysSerPheGlnHisSerProIleSerSerAspPheAlaValLysIleArg
                    10                                  20

GluLeuSerAspTyrLeuLeuGlnAspTyrProValThrValAlaSerAsnLeuGlnAsp
                    30                                  40

GluGluLeuCysGlyGlyLeuTrpArgLeuValLeuAlaGlnArgTrpMetGluArgLeu
                    50                                  60

LysThrValAlaGlySerLysMetGlnGlyLeuLeuGluArgValAsnThrGluIleHis
                    70                                  80

PheValThrLysCysAlaPheGlnProProProSerCysLeuArgPheValGlnThrAsn
                    90                                  100

IleSerArgLeuLeuGlnGluThrSerGluGlnLeuValAlaLeuLysProTrpIleThr
                    110                                 120

ArgGlnAsnPheSerArgCysLeuGluLeuGlnCysGlnProAspSerSerThrLeu
                    130                    SEQ ID NO:144
``` wherein the N-terminus is joined to the C-terminus directly or through a linker capable of joining the N-terminus to the C-terminus and having new C- and N-termini at amino acids;

| | | |
|---|---|---|
| 28–29 | 42–43 | 93–94 |
| 29–30 | 64–65 | 94–95 |
| 30–31 | 65–66 | 95–96 |
| 31–32 | 66–67 | 96–97 |
| 32–33 | 86–87 | 97–98 |
| 34–35 | 87–88 | 98–99 |
| 36–37 | 88–89 | 99–100 |
| 37–38 | 89–90 | 100–101 |
| 38–39 | 90–91 | 101–102 |
| 39–40 | 91–92 | 102–103 |
| 40–41 | 92–93 | respectively; and |
| 41–42 | | | additionally said flt3 receptor agonist polypeptide can be immediately preceded by (methionine$^{-1}$), (alanine$^{-1}$) or (methionine$^{-2}$, alanine$^{-1}$)

The more preferred breakpoints at which new C-terminus and N-terminus can be made are 36–37, 37–38, 38–39, 39–40, 40–41, 41–42, 42–43, 64–65, 65–66, 66–67, 86–87, 87–88, 88–89, 89–90, 90–91, 91–92, 92–93, 93–94, 95,–96, 96–97, 97–98, 99–100 and 100–101

The most preferred breakpoints at which new C-terminus and N-terminus can be made are; 39–40, 65–66, 89–90, 99–100 and 100–101.

The flt3 receptor agonists of the present invention may contain amino acid substitutions, deletions and/or insertions. It is also intended that the flt3 receptor agonists of the present invention may also have amino acid deletions at either/or both the N- and C-termini of the original protein and or deletions from the new N-and/or C-termini of the sequence rearranged proteins in the formulas shown above.

The flt3 receptor agonists of the present invention may contain amino acid substitutions, deletions and/or insertions.

A preferred embodiment of the present invention the linker (L) joining the N-terminus to the C-terminus is a polypeptide selected from the group consisting of:

GlyGlyGlySer SEQ ID NO:38;
GlyGlyGlySerGlyGlyGlySer SEQ ID NO:39;
GlyGlyGlySerGlyGlyGlySerGlyGlyGlySer SEQ ID NO:40;
SerGlyGlySerGlyGlySer SEQ ID NO:41;
GluPheGlyAsnMet SEQ ID NO:42;
GluPheGlyGlyAsnMet SEQ ID NO:43;
GluPheGlyGlyAsnGlyGlyAsnMet SEQ ID NO:44;
GlyGlySerAspMetAlaGly SEQ ID NO:45;
SerGlyGlyAsnGly SEQ ID NO:46;
SerGlyGlyAsnGlySerGlyGlyAsnGly SEQ ID NO:47;
SerGlyGlyAsnGlySerGlyGlyAsnGlySerGlyGlyAsnGly SEQ ID NO:48;
SerGlyGlySerGlySerGlyGlySerGly SEQ ID NO:49;
SerGlyGlySerGlySerGlyGlySerGlySerGlyGlySerGly SEQ ID NO:50;
GlyGlyGlySerGlyGly SEQ ID NO:51;
GlyGlyGlySerGlyGlyGly SEQ ID NO:52;
GlyGlyGlySerGlyGlyGlySerGlyGly SEQ ID NO:53;
GlyGlyGlySerGlyGlyGlySerGlyGlyGlySerGly SEQ ID NO:54;
GlyGlyGlySerGlyGlyGlySerGlyGlyGlySerGlyGly SEQ ID NO:55;
GlyGlyGlySerGlyGlyGlySerGlyGlySerGlyGlyGlySerGly GlyGlySerGly SEQ ID NO:56;
GlyGlyGlySerGlyGlyGlySerGlyGlySerGlyGlyGlySerGly GlyGlySerGlyGlyGlySer GlyGlyGlySerGly SEQ ID NO:148;
ProProProTrpSerProArgProLeuGlyAlaThrAlaProThrAlaGly GlnProProLeu SEQ ID NO:149;
ProProProTrpSerProArgProLeuGlyAlaThrAlaProThr SEQ ID NO:150; and
ValGluThrValPheHisArgValSer-GlnAspGlyLeuLeuThrSer SEQ ID NO:151.

The present invention also encompasses recombinant human flt3 receptor agonists co-administered or sequentially with one or more additional colony stimulating factors (CSF) including, cytokines, lymphokines, interleukins, hematopoietic growth factors which include but are not limited to GM-CSF, G-CSF, c-mpl ligand (also known as TPO or MGDF), M-CSF, erythropoietin (FLT3), IL-1, IL-4, IL-2, IL-3, IL-5, IL-6, IL-7, IL-8, IL-9, IL-10, IL-11, IL-12, IL-13, IL-15, LIF, human growth hormone, B-cell growth factor, B-cell differentiation factor, eosinophil differentiation factor and stem cell factor (SCF) also known as steel factor or c-kit ligand (herein collectively referred to as "factors"). These co-administered mixtures may be characterized by having the usual activity of both of the peptides or the mixture may be further characterized by having a biological or physiological activity greater than simply the additive function of the presence of the flt3 receptor agonists or the second colony stimulating factor alone. The co-administration may also provide an enhanced effect on the activity or an activity different from that expected by the presence of the flt3 ligand or the second colony stimulating factor. The co-administration may also have an improved activity profile which may include reduction of undesirable biological activities associated with native human flt3 ligand. In addition to the list above, IL-3 variants taught in WO 94/12639 and WO 94/12638 fusion protein taught in WO 95/21197, and WO 95/21254 G-CSF receptor agonists disclosed in WO 97/12977, c-mpl receptor agonists disclosed in WO 97/12978, IL-3 receptor agonists disclosed in WO 97/12979 and multi-functional receptor agonists taught in WO 97/12985 can be co-administered with the polypeptides of the present invention. As used herein "IL-3 variants" refer to IL-3 variants taught in WO 94/12639 and WO 94/12638. As used herein "fusion proteins" refer to fusion protein taught in WO 95/21197, and WO 95/21254. As used herein "G-CSF receptor agonists" refer to G-CSF receptor agonists disclosed in WO 97/12978. As used herein "c-mpl receptor agonists" refer to c-mpl receptor agonists disclosed in WO 97/12978. As used herein "IL-3 receptor agonists" refer to IL-3 receptor agonists disclosed in WO 97/12979. As used herein "multi-functional receptor agonists" refer to multi-functional receptor agonists taught in WO 97/12985.

In addition, it is envisioned that in vitro uses would include the ability to stimulate bone marrow and blood cell activation and growth before the expanded cells are infused into patients. Another intended use is for the production of dendritic cells both in vivo and ex vivo.

BRIEF DESCRIPTION OF THE FIGURES

FIG. 1 schematically illustrates the sequence rearrangement of a protein. The N-terminus (N) and the C-terminus (C) of the native protein are joined through a linker, or joined directly. The protein is opened at a breakpoint creating a new N-terminus (new N) and a new C-terminus (new-C) resulting in a protein with a new linear amino acid sequence. A rearranged molecule may be synthesized de novo as linear molecule and not go through the steps of joining the original N-terminus and the C-terminus and opening of the protein at the breakpoint.

FIG. 2 shows a schematic of Method I, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the amino acid 11 (a.a. 1–10 are deleted) through a linker regionand a new C-terminus created at amino acid 96 of the original sequence.

FIG. 3 shows a schematic of Method II, for creating new proteins in which the original N-terminus and C-terminus of the native protein are joined without a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the original N-terminus and a new C-terminus created at amino acid 96 of the original sequence.

FIG. 4 shows a schematic of Method III, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to amino acid 1 through a linker region and a new C-terminus created at amino acid 96 of the original sequence.

FIGS. 5a and 5b shows the DNA sequence encoding the 209 amino acid mature form of flt3 ligand from Lyman et al. (*Oncogene* 11:1165–1172, 1995).

FIG. 6 shows the DNA sequence encoding the 134 amino acid soluble form of flt3 ligand from Lyman et al. (*Oncogene* 11:1165–1172, 1995).

FIG. 7 shows the bioactivity of the flt3 receptor agonists pMON32320 and pMON32321 compared to recombinant native flt3 (Genzyme) and pMON30237 (1–134 form of the flt3 ligand expressed by mammalian cell (BHK) culture) in the MUTZ-2 cell proliferation assay. MT=mock transfection.

DETAILED DESCRIPTION OF THE INVENTION

Flt3 receptor agonists of the present invention may be useful in the treatment of diseases characterized by decreased levels of hematopoietic cells.

A flt3 receptor agonist may be useful in the treatment or prevention of hematopoietic disorders. Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti-convulsants such as phenytoin or carbamazepine, anti-thyroids such as propylthiouracil and methimazole and diuretics. flt3 receptor agonists may be useful in preventing or treating the bone marrow suppression or hematopoietic deficiencies which often occur in patients treated with these drugs.

Hematopoietic deficiencies may also occur as a result of viral, microbial or parasitic infections, burns and as a result of treatment for renal disease or renal failure, e.g., dialysis. The present peptide may be useful in treating such hematopoietic deficiency.

Another aspect of the present invention provides plasmid DNA vectors for use in the method of expression of these novel flt3 receptor agonists. These vectors contain the novel DNA sequences described above which code for the novel polypeptides of the invention. Appropriate vectors which can transform host cells capable of expressing the flt3 receptor agonists include expression vectors comprising nucleotide sequences coding for the flt3 receptor agonists joined to transcriptional and translational regulatory sequences which are selected according to the host cells used. Vectors incorporating modified sequences as described above are included in the present invention and are useful in the production of the modified flt3 receptor agonist polypeptides. The vector employed in the method also contains selected regulatory sequences in operative association with the DNA coding sequences of the invention and capable of directing the replication and expression thereof in selected host cells.

As another aspect of the present invention, there is provided a novel method for producing the novel family of human flt3 receptor agonists. The method of the present invention involves culturing suitable cells or cell line, which has been transformed with a vector containing a DNA sequence coding for expression of the novel flt3 receptor agonist polypeptide. Suitable cells or cell lines may include various strains of bacteria such as *E. coli*, yeast, mammalian cells, or insect cells may be utilized as host cells in the method of the present invention.

Other aspects of the present invention are methods and therapeutic compositions for treating the conditions referred to above. Such compositions comprise a therapeutically effective amount of one or more of the flt3 receptor agonists of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.5–150 $\mu$g/kg of non-glycosylated flt3 receptor agonists protein per kilogram of body weight. Dosages would be adjusted relative to the activity of a given receptor agonist and it would not be unreasonable to note that dosage regimens may include doses as low as 0.1 microgram and as high as 1 milligram per kilogram of body weight per day. In addition, there may exist specific circumstances where dosages of flt3 receptor agonist would be adjusted higher or lower than the range of 0.5–150 micrograms per kilogram of body weight. These include co-administration with other CSF or growth factors; co-administration with chemotherapeutic drugs and/or radiation; the use of glycosylated flt3 receptor agonists; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration with the polypeptides of the present invention includes GM-CSF, G-CSF, c-mpl ligand (also known as TPO or MGDF), M-CSF, erythropoietin (EPO), IL-1, IL-4, IL-2, IL-3, IL-5, IL-6, IL-7, IL-8, IL-9, IL-10, IL-11, IL-12, IL-13, IL-15, LIF, human growth hormone, B-cell growth factor, B-cell differentiation factor, eosinophil differentiation factor and stem cell factor (SCF) also known as steel factor or c-kit ligand (herein collectively referred to as "factors"), or combinations thereof. In addition to the list above, IL-3 variants taught in WO 94/12639 and WO 94/12638 fusion protein taught in WO 95/21197, and WO 95/21254 G-CSF receptor agonists disclosed in WO 97/12977, c-mpl receptor agonists disclosed in WO 97/12978, IL-3 receptor agonists disclosed in WO 97/12979 and multi-functional receptor agonists taught in WO 97/12985 can be co-administered with the polypeptides of the present invention.

The flt3 receptor agonists of the present invention may be useful in the mobilization of hematopoietic progenitors and stem cells in peripheral blood. Peripheral blood derived progenitors have been shown to be effective in reconstituting patients in the setting of autologous marrow transplantation.

Hematopoietic growth factors, including G-CSF and GM-CSF, have been shown to enhance the number of circulating progenitors and stem cells in the peripheral blood. This has simplified the procedure for peripheral stem cell collection and dramatically decreased the cost of the procedure by decreasing the number of pheresis required. The flt3 receptor agonist of the present invention may be useful in mobilization of stem cells and further enhance the efficacy of peripheral stem cell transplantation.

The flt3 receptor agonists of the present invention may also be useful in the ex vivo expansion of hematopoietic progenitors. Colony stimulating factors (CSFs), such as G-CSF, have been administered alone, co-administered with other CSFs, or in combination with bone marrow transplants subsequent to high dose chemotherapy to treat the neutropenia and which is often the result of such treatment. However the period of severe neutropenia may not be totally eliminated. The myeloid lineage, which is comprised of monocytes (macrophages), granulocytes (including neutrophils) and megakaryocytes, is critical in preventing infections and bleeding which can be life-threatening. Neutropenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow or other tissues, such as spleen or peripheral blood, is limited, 2) Graft Versus Host Disease, 3) graft rejection and 4) possible contamination with tumor cells. Stem cells and progenitor cells make up a very small percentage of the nucleated cells in the bone marrow, spleen and peripheral blood. It is clear that a dose response exists such that a greater number of multipotential hematopoietic progenitors will enhance hematopoietic recovery. Therefore, the in vitro expansion of stem cells should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogeneic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells. The limited number of multipotential hematopoietic progenitors may be overcome by ex-vivo expansion of the multipotential hematopoietic progenitors. In addition, stem cells can be specifically isolated based on the presence of specific surface antigens such as CD34+ in order to decrease tumor cell contamination of the marrow graft.

The following patents contain further details on separating stem cells, CD34+ cells, culturing the cells with hematopoietic factors, the use of the cells for the treatment of patients with hematopoietic disorders and the use of hematopoietic factors for cell expansion and gene therapy.

5,061,620 relates to compositions comprising human hematopoietic stem cells provided by separating the stem cells from dedicated cells.

5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM CSF, IL-1, GM-CSF/IL-3 fusion protein and combinations thereof; (3) administering cellular preparation to a patient.

5,240,856 relates to a cell separator that includes an apparatus for automatically controlling the cell separation process.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from other cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1α, IL-3, IL-6 or GM-CSF is discussed in Brandt et al (*J. Clin. Invest.* 86:932–941, 1990).

One aspect of the present invention provides a method for selective ex-vivo expansion of stem cells. The term "stem cell" refers to the multipotential hematopoietic cells as well as early myeloid progenitor and precursors cells which can be isolated from bone marrow, spleen or peripheral blood. The term "expansion" refers to the proliferation and differentiation of the cells. The present invention provides a method for selective ex-vivo expansion of stem cells, comprising the steps of; (a) separating stem cells from other cells, (b) culturing the separated stem cells with a selective medium which contains a flt3 receptor agonist and optionally a second colony stimulating factor, and (c) harvesting the cultured stems cells. Stem cells, as well as committed progenitor cells destined to become neutrophils, erythrocytes, platelets, etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34+, Thy-1+ and lin−, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several subpopulations characterized by the presence or absence of co-expression of different lineage associated cell surface associated molecules. The most immature progenitor cells do not express any known lineage associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various colony stimulating factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various colony stimulating factors including c-kit ligand (Brandt et al., *Blood* 83:1507–1514, 1994; McKenna et al., *Blood* 86:3413–3420, 1995), IL-3 (Brandt et al., *Blood* 83:1507–1514, 1994; Sato et al., *Blood* 82:3600–3609, 1993), G-CSF (Sato et al., *Blood* 82:3600–3609, 1993), GM-CSF (Sato et al., *Blood* 82:3600–3609, 1993), IL-1 (Muench et al., *Blood* 81:3463–3473, 1993), IL-6 (Sato et al., *Blood* 82:3600–3609, 1993), IL-11 (Lemoli et al., *Exp. Hem.* 21:1668–1672, 1993; Sato et al., *Blood* 82:3600–3609, 1993), flt3 ligand (McKenna et al., *Blood* 86:3413 3420, 1995) and/or combinations thereof (Brandt et al., *Blood* 83:1507 1514, 1994; Haylock et al., *Blood* 80:1405–1412, 1992, Koller et al., *Biotechnology* 11:358–363, 1993; Lemoli et al., *Exp. Hem.* 21:1668–1672, 1993), McKenna et al., *Blood* 86:3413–3420, 1995; Muench et al., *Blood* 81:3463–3473, 1993; Patchen et al., *Biotherapy* 7:13–26, 1994; Sato et al., *Blood* 82:3600–3609, 1993; Smith et al., *Exp. Hem.* 21:870–877, 1993; Steen et al., *Stem Cells* 12:214–224, 1994; Tsujino et al., *Exp. Hem.* 21:1379–1386, 1993). Among the individual colony stimulating factors, hIL-3 has been shown to be one of the most potent in expanding peripheral blood CD34+ cells (Sato et al., *Blood* 82:3600–3609, 1993; Kobayashi et al., *Blood* 73:1836–1841, 1989). However, no single factor has been shown to be as effective as the combination of multiple factors. The present invention provides methods for ex vivo expansion that utilize novel flt3 receptor agonists.

Another aspect of the invention provides methods of sustaining and/or expanding hematopoietic precursor cells which includes inoculating the cells into a culture vessel which contains a culture medium that has been conditioned by exposure to a stromal cell line such as HS-5 (WO 96/02662, Roecklein and Torok-Strob, *Blood* 85:997–1105, 1995) that has been supplemented with a flt3 receptor agonist of the present invention.

It is also envisioned that uses of flt3 receptor agonists of the present invention would include blood banking applications, where the flt3 receptor agonists are given to a patient to increase the number of blood cells and blood products are removed from the patient, prior to some medical procedure, and the blood products are stored and transfused back into the patient after the medical procedure. Additionally, it is envisioned that uses of flt3 receptor agonists would include giving the flt3 receptor agonists to a blood donor prior to blood donation to increase the number of blood cells, thereby allowing the donor to safely give more blood.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270:404–410, 1995) include; 1) the treatment of many congenital metabolic disorders and immunodeficiencies (Kay and Woo, *Trends Genet.* 10:253–257, 1994), 2) neurological disorders (Friedmann, *Trends Genet.* 10:210–214, 1994), 3) cancer (Culver and Blaese, *Trends Genet.* 10:174–178, 1994) and 4) infectious diseases (Gilboa and Smith, *Trends Genet.* 10:139–144, 1994).

There are a variety of methods, known to those with skill in the art, for introducing genetic material into a host cell. A number of vectors, both viral and non-viral have been developed for transferring therapeutic genes into primary cells. Viral based vectors include; 1) replication deficient recombinant retrovirus (Boris-Lawrie and Temin, *Curr. Opin. Genet. Dev.* 3:102–109, 1993; Boris-Lawrie and Temin, *Annal. New York Acad. Sci.* 716:59–71, 1994; Miller, *Current Top. Microbiol. Immunol.* 158:1–24, 1992) and replication-deficient recombinant adenovirus (Berkner, *Bio-Techniques* 6:616–629, 1988; Berkner, *Current Top. Microbiol. Immunol.* 158:39–66, 1992; Brody and Crystal, *Annal. New York Acad. Sci.* 716:90–103, 1994). Non-viral based vectors include protein/DNA complexes (Cristiano et al., *PNAS USA*. 90:2122–2126, 1993; Curiel et al., *PNAS USA* 88:8850–8854, 1991; Curiel, *Annal. New York Acad. Sci.* 716:36–58, 1994), electroporation and liposome mediated delivery such as cationic liposomes (Farhood et al., *Annal. New York Acad. Sci.* 716:23–35, 1994).

The present invention provides an improvement to the existing methods of expanding hematopoietic cells, into which new genetic material has been introduced, in that it provides methods utilizing flt3 receptor agonists that may have improved biological activity and/or physical properties.

Another intended use of the flt-3 receptor agonists of the present invention is for the generation of larger numbers of dendritic cells, from precursors, to be used as adjuvants for immunization. Dendritic cells play a crucial role in the immune system. They are the professional antigen-presenting cells most efficient in the activation of resting T cells and are the major antigen-presenting cells for activation of naive T cells in vivo and, thus, for initiation of primary immune responses. They efficiently internalize, process and present soluble tumor-specific antigens (Ag). Dendritic cells have the unique capacity to cluster naive T cells and to respond to Ag encounter by rapid up-regulation of the expression of major histocompatability complex (MHC) and co-stimulatory molecules, the production of cytokines and migration towards lymphatic organs. Since dendritic cells are of central importance for sensitizing the host against a neoantigen for CD4-dependent immune responses, they may also play a crucial role in the generation and regulation of tumor immunity.

Dendritic cells originate from a bone marrow CD34+ precursor common to granulocytes and macrophages, and the existence of a separate dendritic cell colony-forming unit (CFU-DC) that give rise to pure dendritic cell colonies has been established in humans. In addition, a post-CFU CD14+ intermediate has been described with the potential to differentiate along the dendritic cell or the macrophage pathway under distinct cytokine conditions. This bipotential precursor is present in the bone marrow, cord blood and peripheral blood. Dendritic cells can be isolated by the cell specific marker, CD83, which is expressed on mature dendritic cells, to delineate the maturation of cultured dendritic cells.

Dendritic cells based strategies provide a method for enhancing immune response against tumors and infectious agents. AIDS is another disease for which dendritic cell based therapies can be used, since dendritic cells can play a major role in promoting HIV-1 replication. An immunotherapy requires the generation of dendritic cells from cancer patients, their in vitro exposure to tumor Ag, derived from surgically removed tumor masses, and reinjection of these cells into the tumor patients. Relatively crude membrane preparations of tumor cells will suffice as sources of tumor antigen, avoiding the necessity for molecular identification of the tumor antigen. The tumor antigen may also be synthetic peptides, carbohydrates, or nucleic acid sequences. In addition, concomitant administration of cytokines such as the flt-3 receptor agonists of the present invention may further facilitate the induction of tumor immunity. It is foreseen that the immunotherapy can be in an in vivo setting, wherein the flt-3 receptor agonists of the present invention is administered to a patient, having a tumor, alone or with other hematopoietic growth factors to increase the number of dendritic cells and endogenous tumor antigen is presented on the dendritic cells. It is also envisioned that in vivo immunotherapy can be with exogenous antigen. It is also envisioned that the immunotherapy treatment may include the mobilization of dendritic cell precursors or mature dendritic, by administering the flt-3 receptor agonists of the present invention alone or with other hematopoietic growth factors to the patient, removing the dendritic cell precursors or mature dendritic cells from the patient, exposing the dendritic cells to antigen and returning the dendritic cells to the patient. Furthermore, the dendritic cells that have been removed can be cultured ex vivo with the flt-3 receptor agonists of the present invention alone or with other hematopoietic growth factors to increase the number of dendritic cells prior to exposure to antigen. Dendritic cells based strategies also provide a method for reducing the immune response in auto-immune diseases.

Studies on dendritic cells have been greatly hampered by difficulties in preparing the cells in sufficient numbers and in a reasonably pure form. In an ex-vivo cell expansion setting, granulocyte-macrophage colony-stimulating factor (GM-CSF) and tumor necrosis factor-α (TNF-α) cooperate in the ex vivo generation of dendritic cells from hematopoietic progenitors (CD34+ cells) retrieved from bone marrow, cord blood, or peripheral blood and flk-2/flt-3 ligand and c-kit ligand (stem cell factor [SCF]) synergize to enhance the GM-CSF plus TNF-α induced generation of dendritic cells (Siena, S. et al. *Experimental Hematology* 23:1463–1471, 1995). Also provide is a method of ex vivo expansion of dendritic cell precursors or mature dendritic cells using the flt-3 receptor agonists of the present invention to provide sufficient quantities of dendritic cells for immunotherapy.

Determination of the Linker

The length of the amino acid sequence of the linker can be selected empirically or with guidance from structural information, or by using a combination of the two approaches.

When no structural information is available, a small series of linkers can be prepared for testing using a design whose length is varied in order to span a range from 0 to 50 Å and whose sequence is chosen in order to be consistent with surface exposure (hydrophilicity, Hopp & Woods, *Mol. Immunol.* 20: 483–489, 1983; Kyte & Doolittle, *J. Mol. Biol.* 157:105–132, 1982; solvent exposed surface area, Lee & Richards, *J. Mol. Biol.* 55:379–400, 1971) and the ability to adopt the necessary conformation without deranging the configuration of the flt3 receptor agonist (conformationally flexible; Karplus & Schulz, *Naturwissenschaften* 72:212–213, (1985). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, *Critical Rev. Biotech.* 12:437–462, 1992); if they are too long, entropy effects will likely destabilize the three-dimensional fold, and may also make folding kinetically impractical, and if they are too short, they will likely destabilize the molecule because of torsional or steric strain.

Those skilled in the analysis of protein structural information will recognize that using the distance between the chain ends, defined as the distance between the c-alpha carbons, can be used to define the length of the sequence to be used, or at least to limit the number of possibilities that must be tested in an empirical. selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser (SEQ ID NO:38) cassette approach mentioned above; or optionally a combination of the original sequence and new sequence having the appropriate total length may be used.

Determination of the Amino and Carboxyl Termini of flt3 Receptor Agonists

Sequences of flt3 receptor agonists capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence.

It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops; Kabsch & Sander, *Biopolymers* 22: 2577–2637, 1983; the degree of solvent exposure of amino acid residues, the extent and type of interactions of residues with one another (Chothia, *Ann. Rev. Biochem.* 53:537–572; 1984) and the static and dynamic distribution of conformations along the polypeptide chain (Alber & Mathews, *Methods Enzymol.* 154: 511–533, 1987). In some cases additional information is known about solvent exposure of residues; one example is a site of post-translational attachment of carbohydrate which is necessarily on the surface of the protein. When experimental structural information is not available, or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile & Salvatore, *Eur. J. Biochem.* 218:603–621, 1993). Thus using either the experimentally derived structural information or predictive methods (e.g., Srinivisan & Rose *Proteins: Struct., Funct. & Genetics*, 22: 81–99, 1995) the parental amino acid sequence is inspected to classify regions according to whether or not they are integral to the maintenance of secondary and tertiary structure. The occurrence of sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region.

TABLE 1

| OLIGONUCLEOTIDES | |
|---|---|
| NCOFLT | CTGACCATGGCNACCCAGGACTGCTCCTTCCAA SEQ ID NO:57; |
| HIND160 | ACTGAAGCTTAGGGCTGACACTGCAGCTCCAG SEQ ID NO:58; |
| HIND165 | ACTGAAGCTTACAGGGTTGAGGAGTCGGGCTG SEQ ID NO:59; |
| FL23For | GACTGCCATGGCNACYCAGGAYTGYTCYTTYCAACACAGCCCCATC SEQ ID NO:60; |
| FH3AFor | GACTGCCATGGCNACYCAGGAYTGYTCYTTYCAACACAGCCCCATC SEQ ID NO:61; |
| SCF.REV | TGTCCAAACTCATCAATGTATC SEQ ID NO:62; |
| 39FOR | CATGGCCATGGCCGACGAGGAGCTCTGCGGGGGCCTCT SEQ ID NO:63; |
| 39REV | GCTAGAAGCTTACTGCAGGTTGGAGGCCACGGTGAC SEQ ID NO:64; |
| 65FOR | CATGGCCATGGCCTCCAAGATGCAAGGCTTGCTGGAGC SEQ ID NO:65; |
| 65REV | GCTAGAAGCTTACCCAGCGACAGTCTTGAGCCGCTC SEQ ID NO:66; |
| 89FOR | CATGGCCATGGCCCCCCCCAGCTGTCTTCGCTTCGT SEQ ID NO:67; |
| 89REV | GCTAGAAGCTTAGGGCTGAAAGGCACATTTGGTGACA SEQ ID NO:68; |
| L5A | CCCTGTCTGGCGGCAACGGCACCCAGGACTGCTCCTTCCAAC SEQ ID NO:69; |
| L10A | GCGGTAACGGCAGTGGAGGTAATGGCACCCAGGACTGCTCCTTCCAAC SEQ ID NO:70; |
| L15A | ACGGCAGTGGTGGCAATGGGAGCGGCGGAAATGGAACCCAGGACTGCTCCT TCCAAC SEQ ID NO:71; |
| L5B | GTGCCGTTGCCGCCAGACAGGGTTGAGGAGTCGGGCTG SEQ ID NO:72; |
| L10B | ATTACCTCCACTGCCGTTACCGCCTGACAGGGTTGAGGAGTCGGGCTG SEQ ID NO:73; |
| L15B | GCTCCCATTGCCACCACTGCCGTTACCTCCAGACAGGGTTGAGGA GTCGGGCTG SEQ ID NO:74; |
| L15C | GATGAGGATCCGGTGGCAATGGGAGCGGCGGAAATGGAACCCAGG ACTGCTCCTTCCACC SEQ ID NO:75; |
| L15D | GATGACGGATCCGTTACCTCCAGACAGGGTTGAGGAGTCGGGCTG SEQ ID NO:76; |
| L15E | GATGACGGATCCGGAGGTAATGGCACCCAGGACTGCTCCTTCCAAC SEQ ID NO:77; |
| 339FOR2 | GACTGCCATGGCCGACGAGGAGCTCTGCG SEQ ID NO:78; |
| 339REV2 | GACTCAAGCTTACTGCAGGTTGGAGGCC SEQ ID NO:79; |

TABLE 1-continued

OLIGONUCLEOTIDES

| | | |
|---|---|---|
| 339-10FOR3 | GACTCGGGATCCGGAGGTTCTGGCACCCAGGACTGCTCC | SEQ ID NO: 80; |
| 339-15FOR2 | GACTGGGATCCGGTGGCAGTGGGAGCGGCGGATCTGGAACC | SEQ ID NO:81; |
| 339REV3 | GACTTGGGATCCACTACCTCCAGACAGGGTTGAGGAGTC | SEQ ID NO:82; |
| FLN3 | ACTGACGGATCCACCGCCCAGGGTTGAGGAGTCGGGCTG | SEQ ID NO:83; |
| FLN7 | ACTGACGGATCCACCTCCTGACCCACCGCCCAGGGTTGAGGAGTCGGGCTG SEQ ID NO:84; | |
| FLN11 | ACTGACGGATCCACCTCCTGACCCACCTCCTGACCCACCGCCCAG GGTTGAGGAGTCGGGCTG | SEQ ID NO:85; |
| C-term | ACGTAAAGCTTACAGGGTTGAGGAGTCG | SEQ ID NO:86; |
| FLC3 | GTCAGTGGATCCGGAGGTACCCAGGACTGCTCCTTCCAAC | SEQ ID NO:87; |
| FLC4 | GTCAGTGGATCCGGAGGTGGCACCCAGGACTGCTCCTTCCAAC SEQ ID NO:88; | |
| FLC10 | GTCAGTGGATCCGGAGGTGGCTCAGGGGAGGTAGTGGTACCCAG GACTGCTCCTTCCAAC | SEQ ID NO:89; |
| Flt36 | GTTGCCATGGCNTCNAAYCTGCARGAYGARGARCTGTGCGGGGGCCTCTGG CGGCTG | SEQ ID NO:90; |
| Flt37 | GTTGCCATGGCNAAYCTGCARGAYGARGARCTGTGYGGGGGCCTCTGGCG GCTGGTC | SEQ ID NO:91; |
| Flt38 | GTTGCCATGGCNCTGCARGAYGARGARCTGTGYGGYGGCCTCTGGCGGCTG GTCCTG | SEQ ID NO:92; |
| Flt39 | GTTGCCATGGCNCARGAYGARGARCTGTGYGGYGGYCTCTGGCGGCTGGTC CTGGCA | SEQ ID NO:93; |
| Flt40 | GTTGCCATGGCNGAYGARGARCTGTGYGGYGGYCTCTGGCGGCTGGTCCTG GCACAG | SEQ ID NO:94; |
| Flt41 | GTTGCCATGGCNGARGARCTGTGYGGYGGYCTCTGGCGGCTGGTCCTGGCA CAGCGC | SEQ ID NO:95; |
| Flt42 | GTTGCCATGGCNGARCTGTGYGGYGGYCTGTGGCGYCTGGTCCTGGCACAG CGCTGG | SEQ ID NO:96; |
| Flt43 | GTTGCCATGGCNCTGTGYGGYGGYCTGTGGCGYCTGGTCCTGGCACAGCGC TGGATG | SEQ ID NO:97; |
| 36REV | TATGCAAGCTTAGGCCACGGTGACTGGGTA | SEQ ID NO:98; |
| 37REV | TATGCAAGCTTAGGAGGCCACGGTGACTGG | SEQ ID NO:99; |
| 38REV | TATGCAAGCTTAGTTGGAGGCCACGGTGAC | SEQ ID NO:100; |
| 39REV | TATGCAAGCTTACAGGTTGGAGGCCACGGT | SEQ ID NO:101; |
| 4OREV | TATGCAAGCTTACTGCAGGTTGGAGGCCAC | SEQ ID NO:102, |
| 41REV | TATGCAAGCTTAGTCCTGCAGGTTGGAGGC | SEQ ID NO:103; |
| 42REV | TATGCAAGCTTACTCGTCCTGCAGGTTGGA | SEQ ID NO:104; |
| 43REV | TATGCAAGCTTACTCCTCGTCCTGCAGGTT | SEQ ID NO:105; |

TABLE 2

DNA sequences pMON30237.seq

GCCACCCAGGACTGCTCCTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCC SEQ ID NO:106;

pMON30238.seq

GCCACCCAGGACTGCTCCTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCCGACTCCTCAACCCTG SEQ ID NO:107;

pMON30239.seq

GCCACCCAGGACTGCTCCTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA

TABLE 2-continued

DNA sequences

CCAAATGTGCCTTTCAGGAGACCTCCGAGCAGCTGGTGGCGCTGAAGCCC
TGGATCACTCGCCAGAACTTCTCCCGGTGCCTGGAGCTGCAGTGTCAGCC
CGACTCCTCAACCCTG SEQ ID NO:108;

pMON32329.seq

GGAACTCAGGATTGTTCTTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCC SEQ ID NO:109;

pMON32330.seq

GGTACCCAGGATTGTTCTTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCCGACTCCTCAACCCTG SEQ ID NO:110;

pMON32341.seq

GCCACTCAGGACTGTTCTTTCCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCC SEQ ID NO:111;

pMON32342.seq

GCCACTCAGGACTGCTCTTTTCAACACAGCCCCATCTCCTCCGACTTCGC
TGTCAAAATCCGTGAGCTGTCTGACTACCTGCTTCAAGATTACCCAGTCA
CCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTC
CAAGATGCAAGGCTTGCTGGAGCGCGTGAACACGGAGATACACTTTGTCA
CCAAATGTGCCTTTCAGCCCCCCCCCAGCTGTCTTCGCTTCGTCCAGACC
AACATCTCCCGCCTCCTGCAGGAGACCTCCGAGCAGCTGGTGGCGCTGAA
GCCCTGGATCACTCGCCAGAACTTCTCCCGGTGCCTGGAGCTGCAGTGTC
AGCCCGACTCCTCAACCCTG SEQ ID NO:112;

pMON32320.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGAGGTAACGGATCCGGTGGCAATGGGAGCGGCGGAAATGGAAC
CCAGGACTGCTCCTTCCAACACAGCCCCATCTCCTCCGACTTCGCTGTCA
AAATCCGTGAGCTGTCTGACTACCTGCTTCAAGATTACCCAGTCACCGTG
GCCTCCAACCTGCAG SEQ ID NO:113;

pMON32321.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCAGGCGGTAACGGCAGTGGAGGTAATGGCACCCAGGACTGCTCCTT
CCAACACAGCCCCATCTCCTCCGACTTCGCTGTCAAAATCCGTGAGCTGT
CTGACTACCTGCTTCAAGATTACCCAGTCACCGTGGCCTCCAACCTGCAG
SEQ ID NO:114;

TABLE 2-continued

DNA sequences pMON32322.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGCGGCAACGGCACCCAGGACTGCTCCTTCCAACACAGCCCCAT
CTCCTCCGACTTCGCTGTCAAAATCCGTGAGCTGTCTGACTACCTGCTTC
AAGATTACCCAGTCACCGTGGCCTCCAACCTGCAG SEQ ID NO:115;

pMON32323.seq

GCCTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGTCTGGAGGTAACGGATCCGGTGGCA
ATGGGAGCGGCGGAAATGGAACCCAGGACTGCTCCTTCCAACACAGCCCC
ATCTCCTCCGACTTCGCTGTCAAAATCCGTGAGCTGTCTGACTACCTGCT
TCAAGATTACCCAGTCACCGTGGCCTCCAACCTGCAGGACGAGGAGCTCT
GCGGGGGCCTCTGGCGGCTGGTCCTGGCACAGCGCTGGATGGAGCGGCTC
AAGACTGTCGCTGGG SEQ ID NO:116;

pMON32324.seq

GCCTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGTCTGGAGGTAACGGATCCGGAGGTA
ATGGCACCCAGGACTGCTCCTTCCAACACAGCCCCATCTCCTCCGACTTC
GCTGTCAAAATCCGTGAGCTGTCTGACTACCTGCTTCAAGATTACCCAGT
CACCGTGGCCTCCAACCTGCAGGACGAGGAGCTCTGCGGGGGCCTCTGGC
GGCTGGTCCTGGCACAGCGCTGGATGGAGCGGCTCAAGACTGTCGCTGGG
SEQ ID NO:117;

pMON32325.seq

GCCTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGTCTGGCGGCAACGGCACGCAGGACT
GCTCCTTCCAACACAGCCCCATCTCCTCCGACTTCGCTGTCAAAATCCGT
GAGCTGTCTGACTACCTGCTTCAAGATTACCCAGTCACCGTGGCCTCCAA
CCTGCAGGACGAGGAGCTCTGCGGGGGCCTCTGGCGGCTGGTCCTGGCAC
AGCGCTGGATGGAGCGGCTCAAGACTGTCGCTGGG SEQ ID NO:118;

pMON32326.seq

GCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGAGGTAACGGCAGTGGTGGCAATGGGAGCGGTGGAAATGGAAC
CCAGGACTGCTCCTTCCAACACAGCCCCATCTCCTCCGACTTCGCTGTCA
AAATCCGTGAGCTGTCTGACTACCTGCTTCAAGATTACCCAGTCACCGTG
GCCTCCAACCTGCAGGACGAGGAGCTCTGCGGGGGCCTCTGGCGGCTGGT
CCTGGCACAGCGCTGGATGGAGCGGCTCAAGACTGTCGCTGGGTCCAAGA
TGCAAGGCTTGCTGGAGCGCGTGAACACGGAGATACACTTTGTCACCAAA
TGTGCCTTTCAGCCC SEQ ID NO:119;

pMON32327.seq

GCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCAGGCGGTAACGGCAGTGGAGGTAATGGCACCCAGGACTGCTCCTT
CCAACACAGCCCCATCTCCTCCGACTTCGCTGTCAAAATCCGTGAGCTGT
CTGACTACCTGCTTCAAGATTACCCAGTCACCGTGGCCTCCAACCTGCAG
GACGAGGAGCTCTGCGGGGGCCTCTGGCGGCTGGTCCTGGCACAGCGCTG
GATGGAGCGGCTCAAGACTGTCGCTGGGTCCAAGATGCAAGGCTTGCTGG
AGCGCGTGAACACGGAGATACACTTTGTCACCAAATGTGCCTTTCAGCCC
SEQ ID NO:120;

TABLE 2-continued

DNA sequences pMON32328.seq

GCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGCGGCAACGGCACGCAGGACTGCTCCTTCCAACACAGCCCCAT
CTCCTCCGACTTCGCTGTCAAAATCCGTGAGCTGTCTGACTACCTGCTTC
AAGATTACCCAGTCACCGTGGCCTCCAACCTGCAGGACGAGGAGCTCTGC
GGGGGCCTCTGGCGGCTGGTCCTGGCACAGCGCTGGATGGAGCGGCTCAA
GACTGTCGCTGGGTCCAAGATGCAAGGCTTGCTGGAGCGCGTGAACACGG
AGATACACTTTGTCACCAAATGTGCCTTTCAGCCC SEQ ID NO:121;

pMON32348.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGAGGTAGTGGATCCGGAGGTTCTGGCAACCCAGGACTGCTCCT
TCCAACACAGCCCCATCTCCTCCGACTTCGCTGTCAAAATCCGTGAGCTG
TCTGACTACCTGCTTCAAGATTACCCAGTCACCGTGGCCTCCAACCTGCA
G SEQ ID NO:122;

pMON32350.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGTCTGGAGGTAGTGGATCCGGTGGCAGTGGGAGCGGCGGATCTGGAAC
CCAGGACTGCTCCTTCCAACACAGCCCCATCTCCTCCGACTTCGCTGTCA
AAATCCGTGAGCTGTCTGACTACCTGCTTCAAGATTACCCAGTCACCGTG
GCCTCCAACCTGCAG SEQ ID NO:123;

FLT3N.seq

CCATGGCCACCCAGGACTGCTCCTTCCAACACAGCCCCATCTCCTCCGAC
TTCGCTGTCAAAATCCGTGAGCTGTCTGACTACCTGCTTCAAGATTACCC
AGTCACCGTGGCCTCCAACCTGCAGGACGAGGAGCTCTGCGGGGGCCTCT
GGCGGCTGGTCCTGGCACAGCGCTGGATGGAGCGGCTCAAGACTGTCGCT
GGGTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGGGCGGTGGATCC SEQ ID NO:124;

FLT3C.seq

GGATCCGGAGGTACCCAGGACTGCTCCTTCCAACACAGCCCCATCTCCTC
CGACTTCGCTGTCAAAATCCGTGAGCTGTCTGACTACCTGCTTCAAGATT
ACCCAGTCACCGTGGCCTCCAACCTGCAGGACGAGGAGCTCTGCGGGGGC
CTCTGGCGGCTGGTCCTGGCACAGCGCTGGATGGAGCGGCTCAAGACTGT
CGCTGGGTCCAAGATGCAAGGCTTGCTGGAGCGCGTGAACACGGAGATAC
ACTTTGTCACCAAATGTGCCTTTCAGCCCCCCCCCAGCTGTCTTCGCTTC
GTCCAGACCAACATCTCCCGCCTCCTGCAGGAGACCTCCGAGCAGCTGGT
GGCGCTGAAGCCCTGGATCACTCGCCAGAACTTCTCCCGGTGCCTGGAGC
TGCAGTGTCAGCCCGACTCCTCAACCCTGTAAGCTT EQ ID NO:125;

FLT7N.seq

CCATGGCCACCCAGGACTGCTCCTTCCAACACAGCCCCATCTCCTCCGAC
TTCGCTGTCAAAATCCGTGAGCTGTCTGACTACCTGCTTCAAGATTACCC
AGTCACCGTGGCCTCCAACCTGCAGGACGAGGAGCTCTGCGGGGGCCTCT
GGCGGCTGGTCCTGGCACAGCGCTGGATGGAGCGGCTCAAGACTGTCGCT
GGGTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGGGCGGTGGGTCAGGAGGTGGATCC
SEQ ID NO:126;

FLT4C.seq

TABLE 2-continued

DNA sequences

GGATCCGGAGGTGGCACCCAGGACTGCTCCTTCCAACACAGCCCCATCTC
CTCCGACTTCGCTGTCAAAATCCGTGAGCTGTCTGACTACCTGCTTCAAG
ATTACCCAGTCACCGTGGCCTCCAACCTGCAGGACGAGGAGCTCTGCGGG
GGCCTCTGGCGGCTGGTCCTGGCACAGCGCTGGATGGAGCGGCTCAAGAC
TGTCGCTGGGTCCAAGATGCAAGGCTTGCTGGAGCGCGTGAACACGGAGA
TACACTTTGTCACCAAATGTGCCTTTCAGCCCCCCCCCAGCTGTCTTCGC
TTCGTCCAGACCAACATCTCCCGCCTCCTGCAGGAGACCTCCGAGCAGCT
GGTGGCGCTGAAGCCCTGGATCACTCGCCAGAACTTCTCCCGGTGCCTGG
AGCTGCAGTGTCAGCCCGACTCCTCAACCCTGTAAGCTT SEQ ID NO:127;

FLT11N.seq

CCATGGCCACCCAGGACTGCTCCTTCCAACACAGCCCCATCTCCTCCGAC
TTCGCTGTCAAAATCCGTGAGCTGTCTGACTACCTGCTTCAAGATTACCC
AGTCACCGTGGCCTCCAACCTGCAGGACGAGGAGCTCTGCGGGGGCCTCT
GGCGGCTGGTCCTGGCACAGCGCTGGATGGAGCGGCTCAAGACTGTCGCT
GGGTCCAAGATGCAAGGCTTGCTGGAGCGCGTGAACACGGAGATACACTT
TGTCACCAAATGTGCCTTTCAGCCCCCCCCCAGCTGTCTTCGCTTCGTCC
AGACCAACATCTCCCGCCTCCTGCAGGAGACCTCCGAGCAGCTGGTGGCG
CTGAAGCCCTGGATCACTCGCCAGAACTTCTCCCGGTGCCTGGAGCTGCA
GTGTCAGCCCGACTCCTCAACCCTGGGCGGTGGGTCAGGAGGTGGGTCAG
GAGGTGGATCC SEQ ID NO:128;

FLT10C.seq

GGATCCGGAGGTGGCTCAGGGGGAGGTAGTGGTACCCAGGACTGCTCCTT
CCAACACAGCCCCATCTCCTCCGACTTCGCTGTCAAAATCCGTGAGCTGT
CTGACTACCTGCTTCAAGATTACCCAGTCACCGTGGCCTCCAACCTGCAG
GACGAGGAGCTCTGCGGGGGCCTCTGGCGGCTGGTCCTGGCACAGCGCTG
GATGGAGCGGCTCAAGACTGTCGCTGGGTCCAAGATGCAAGGCTTGCTGG
AGCGCGTGAACACGGAGATACACTTTGTCACCAAATGTGCCTTTCAGCCC
CCCCCCAGCTGTCTTCGCTTCGTCCAGACCAACATCTCCCGCCTCCTGCA
GGAGACCTCCGAGCAGCTGGTGGCGCTGAAGCCCTGGATCACTCGCCAGA
ACTTCTCCCGGTGCCTGGAGCTGCAGTGTCAGCCCGACTCCTCAACCCTG
TAAGCTT SEQ ID NO:129;

pMON32365.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGATCCGGAGGTACCCAGGACTGCTCCTTCCAACACAGCCC
CATCTCCTCCGACTTCGCTGTCAAAATCCGTGAGCTGTCTGACTACCTGC
TTCAAGATTACCCAGTCACCGTGGCCTCCAACCTGCAG SEQ ID NO:130;

pMON32366.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGATCCGGAGGTGGCACCCAGGACTGCTCCTTCCAACACAG
CCCCATCTCCTCCGACTTCGCTGTCAAAATCCGTGAGCTGTCTGACTACC
TGCTTCAAGATTACCCAGTCACCGTGGCCTCCAACCTGCAG SEQ ID NO:131;

pMON32367.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGGTCAGGAGGTGGATCCGGAGGTACCCAGGACTGCTCCTT
CCAACACAGCCCCATCTCCTCCGACTTCGCTGTCAAAATCCGTGAGCTGT
CTGACTACCTGCTTCAAGATTACCCAGTCACCGTGGCCTCCAACCTGCAG
SEQ ID NO:132;

pMON32368.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC

TABLE 2-continued

DNA sequences

TGGAGCGCGTGAACACGGAGATACACTTTGTCACCAAATGTGCCTTTCAG
CCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGATCCGGAGGTGGCTCAGGGGGAGGTAGTGGTACCCAGGA
CTGCTCCTTCCAACACAGCCCCATCTCCTCCGACTTCGCTGTCAAAATCC
GTGAGCTGTCTGACTACCTGCTTCAAGATTACCCAGTCACCGTGGCCTCC
AACCTGCAG SEQ ID NO:133;

pMON32369.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCAGCTGTCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGGTCAGGAGGTGGGTCAGGAGGTGGATCCGGAGGTGGCAC
CCAGGACTGCTCCTTCCAACACAGCCCCATCTCCTCCGACTTCGCTGTCA
AAATCCGTGAGCTGTCTGACTACCTGCTTCAAGATTACCCAGTCACCGTG
GCCTCCAACCTGCAG SEQ ID NO:134;

pMON32370.seq

GCCGACGAGGAGCTCTGCGGGGGCCTCTGGCGGCTGGTCCTGGCACAGCG
CTGGATGGAGCGGCTCAAGACTGTCGCTGGGTCCAAGATGCAAGGCTTGC
TGGAGCGCGTGAACACGGAGATACACTTTGTCACCAAATGTGCCTTTCAG
CCCCCCCCAGCTGCCTTCGCTTCGTCCAGACCAACATCTCCCGCCTCCT
GCAGGAGACCTCCGAGCAGCTGGTGGCGCTGAAGCCCTGGATCACTCGCC
AGAACTTCTCCCGGTGCCTGGAGCTGCAGTGTCAGCCCGACTCCTCAACC
CTGGGCGGTGGGTCAGGAGGTGGGTCAGGAGGTGGATCCGGAGGTGGCTC
AGGGGGAGGTAGTGGTACCCAGGACTGCTCCTTCCAACACAGCCCCATCT
CCTCCGACTTCGCTGTCAAAATCCGTGAGCTGTCTGACTACCTGCTTCAA
GATTACCCAGTCACCGTGGCCTCCAACCTGCAG SEQ ID NO:135;

pMON35712.seq

GCCGATTACCCAGTCACCGTGGCCTCCAACCTGCAGGACGAGGAGCTCTGCGGGG
GCCTCTGGCGGCTGGTCCTGGCACAGCGCTGGATGGAGCGGCTCAAGACTGTCGC
TGGGTCCAAGATGCAAGGCTTGCTGGAGCGCGTGAACACGGAGATACACTTTGTC
ACCAAATGTGCCTTTCAGCCCCCCCCCAGCTGTCTTCGCTTCGTCCAGACCAACA
TCTCCCGCCTCCTGCAGGAGACCTCCGAGCAGCTGGTGGCGCTGAAGCCCTGGAT
CACTCGCCAGAACTTCTCCCGGTGCCTGGAGCTGCAGTGTCAGCCCGACTCCTCA
ACCCTGGGCGGTGGGTCAGGAGGTGGGTCAGGAGGTGGATCCGGAGGTGGCACCC
AGGACTGCTCCTTCCAACACAGCCCCATCTCCTCCGACTTCGCTGTCAAAATCCG
TGAGCTGTCTGACTACCTGCTTCAA SEQ ID NO:136;

pMON35713.seq

GCCGCCTCCAACCTGCAGGACGAGGAGCTCTGCGGGGGCCTCTGGCGGCTGGTCC
TGGCACAGCGCTGGATGGAGCGGCTCAAGACTGTCGCTGGGTCCAAGATGCAAGG
CTTGCTGGAGCGCGTGAACACGGAGATACACTTTGTCACCAAATGTGCCTTTCAG
CCCCCCCCAGCTGTCTTCGCTTCGTCCAGACCAACATCTCCCGCCTCCTGCAGG
AGACCTCCGAGCAGCTGGTGGCGCTGAAGCCCTGGATCACTCGCCAGAACTTCTC
CCGGTGCCTGGAGCTGCAGTGTCAGCCCGACTCCTCAACCCTGGGCGGTGGGTCA
GGAGGTGGGTCAGGAGGTGGATCCGGAGGTGGCACCCAGGACTGCTCCTTCCAAC
ACAGCCCCATCTCCTCCGACTTCGCTGTCAAAATCCGTGAGCTGTCTGACTACCT
GCTTCAAGATTACCCAGTCACCGTG SEQ ID NO:137;

pMON35714.seq

GCCGTCGCTGGGTCCAAGATGCAAGGCTTGCTGGAGCGCGTGAACACGGAGATAC
ACTTTGTCACCAAATGTGCCTTTCAGCCCCCCCCCAGCTGTCTTCGCTTCGTCCA
GACCAACATCTCCCGCCTCCTGCAGGAGACCTCCGAGCAGCTGGTGGCGCTGAAG
CCCTGGATCACTCGCCAGAACTTCTCCCGGTGCCTGGAGCTGCAGTGTCAGCCCG
ACTCCTCAACCCTGGGCGGTGGGTCAGGAGGTGGGTCAGGAGGTGGATCCGGAGG
TGGCACCCAGGACTGCTCCTTCCAACACAGCCCCATCTCCTCCGACTTCGCTGTC
AAAATCCGTGAGCTGTCTGACTACCTGCTTCAAGATTACCCAGTCACCGTGGCCT
CCAACCTGCAGGACGAGGAGCTCTGCGGGGGCCTCTGGCGGCTGGTCCTGGCACA
GCGCTGGATGGAGCGGCTCAAGACT SEQ ID NO:138;

pMON35715.seq

GCCTCCAAGATGCAAGGCTTGCTGGAGCGCGTGAACACGGAGATACACTTTGTCA
CCAAATGTGCCTTTCAGCCCCCCCCCAGCTGTCTTCGCTTCGTCCAGACCAACAT
CTCCCGCCTCCTGCAGGAGACCTCCGAGCAGCTGGTGGCGCTGAAGCCCTGGATC
ACTCGCCAGAACTTCTCCCGGTGCCTGGAGCTGCAGTGTCAGCCCGACTCCTCAA

TABLE 2-continued

DNA sequences

CCCTGGGCGGTGGGTCAGGAGGTGGGTCAGGAGGTGGATCCGGAGGTGGCACCCA
GGACTGCTCCTTCCAACACAGCCCCATCTCCTCCGACTTCGCTGTCAAAATCCGT
GAGCTGTCTGACTACCTGCTTCAAGATTACCCAGTCACCGTGGCCTCCAACCTGC
AGGACGAGGAGCTCTGCGGGGGCCTCTGGCGGCTGGTCCTGGCACAGCGCTGGAT
GGAGCGGCTCAAGACTGTCGCTGGG SEQ ID NO:139;

pMON35716.seq

GCCCCCCCCAGCTGTCTTCGCTTCGTCCAGACCAACATCTCCCGCCTCCTGCAGG
AGACCTCCGAGCAGCTGGTGGCGCTGAAGCCCTGGATCACTCGCCAGAACTTCTC
CCGGTGCCTGGAGCTGCAGTGTCAGCCCGACTCCTCAACCCTGGGCGGTGGGTCA
GGAGGTGGGTCAGGAGGTGGATCCGGAGGTGGCACCCAGGACTGCTCCTTCCAAC
ACAGCCCCATCTCCTCCGACTTCGCTGTCAAAATCCGTGAGCTGTCTGACTACCT
GCTTCAAGATTACCCAGTCACCGTGGCCTCCAACCTGCAGGACGAGGAGCTCTGC
GGGGGCCTCTGGCGGCTGGTCCTGGCACAGCGCTGGATGGAGCGGCTCAAGACTG
TCGCTGGGTCCAAGATGCAAGGCTTGCTGGAGCGCGTGAACACGGAGATACACTT
TGTCACCAAATGTGCCTTTCAGCCC SEQ ID NO:140;

pMON 35717.seq

GCCCGCTTCGTCCAGACCAACATCTCCCGCCTCCTGCAGGAGACCTCCGAGCAGC
TGGTGGCGCTGAAGCCCTGGATCACTCGCCAGAACTTCTCCCGGTGCCTGGAGCT
GCAGTGTCAGCCCGACTCCTCAACCCTGGGCGGTGGGTCAGGAGGTGGGTCAGGA
GGTGGATCCGGAGGTGGCACCCAGGACTGCTCCTTCCAACACAGCCCCATCTCCT
CCGACTTCGCTGTCAAAATCCGTGAGCTGTCTGACTACCTGCTTCAAGATTACCC
AGTCACCGTGGCCTCCAACCTGCAGGACGAGGAGCTCTGCGGGGGCCTCTGGCGG
CTGGTCCTGGCACAGCGCTGGATGGAGCGGCTCAAGACTGTCGCTGGGTCCAAGA
TGCAAGGCTTGCTGGAGCGCGTGAACACGGAGATACACTTTGTCACCAAATGTGC
CTTTCAGCCCCCCCCCAGCTGTCTT SEQ ID NO:142;

pMON 35718.seq

GCCACCAACATCTCCCGCCTCCTGCAGGAGACCTCCGAGCAGCTGGTGGCGCTGA
AGCCCTGGATCACTCGCCAGAACTTCTCCCGGTGCCTGGAGCTGCAGTGTCAGCC
CGACTCCTCAACCCTGGGCGGTGGGTCAGGAGGTGGGTCAGGAGGTGGATCCGGA
GGTGGCACCCAGGACTGCTCCTTCCAACACAGCCCCATCTCCTCCGACTTCGCTG
TCAAAATCCGTGAGCTGTCTGACTACCTGCTTCAAGATTACCCAGTCACCGTGGC
CTCCAACCTGCAGGACGAGGAGCTCTGCGGGGGCCTCTGGCGGCTGGTCCTGGCA
CAGCGCTGGATGGAGCGGCTCAAGACTGTCGCTGGGTCCAAGATGCAAGGCTTGC
TGGAGCGCGTGAACACGGAGATACACTTTGTCACCAAATGTGCCTTTCAGCCCCC
CCCCAGCTGTCTTCGCTTCGTCCAG SEQ ID NO:143;

TABLE 3

PROTEIN SEQUENCES pMON30237 .pep

AlaThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyAlaLeuTrpArgLeuValLeuAlaGlnArgTrpMetGluArg
LeuLysThrValAlaGlySerLysMetGlnGlyLeuLeuGluLeuValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnPro SEQ ID NO:1;

pMON30238 .pep

AlaThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnProAspSerSerThrLeu
SEQ ID NO:2;

pMON30239 .pep

AlaThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnGluThrSerGluGlnLeuValAlaLeuLysPro

TABLE 3-continued

PROTEIN SEQUENCES

TrpIleThrArgGlnAsnPheSerArgCysLeuGluLeuGlnCysGlnProAspSerSer
ThrLeu SEQ ID NO:3;

pMON32329 .pep

GlyThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnPro SEQ ID NO:4;

pMON32330 .pep

GlyThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnProAspSerSerThrLeu
SEQ ID NO:5;

pMON32341 .pep

AlaThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnPro SEQ ID NO:6;

pMON32342 .pep

AlaThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeuArgPheValGlnThr
AsnIleSerArgLeuLeuGlnGluThrSerGluGlnLeuValAlaLeuLysProTrpIle
ThrArgGlnAsnPheSerArgCysLeuGluLeuGlnCysGlnProAspSerSerThrLeu
SEQ ID NO:7;

pMON32320 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuSerGlyGlyAsnGlySerGlyGlyAsnGlySerGlyGlyAsnGlyThrGlnAspCys
SerPheGlnHisSerProIleSerSerAspPheAlaValLysIleArgGluLeuSerAsp
TyrLeuLeuGlnAspTyrProValThrValAlaSerAsnLeuGln SEQ ID NO:8;

pMON32321 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuSerGlyGlyAsnGlySerGlyGlyAsnGlyThrGlnAspCysSerPheGlnHisSer
ProIleSerSerAspPheAlaValLysIleArgGluLeuSerAspTyrLeuLeuGlnAsp
TyrProValThrValAlaSerAsnLeuGln SEQ ID NO:9;

pMON32322 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuSerGlyGlyAsnGlyThrGlnAspCysSerPheGlnHisSerProIleSerSerAsp
PheAlaValLysIleArgGluLeuSerAspTyrLeuLeuGlnAspTyrProValThrVal
AlaSerAsnLeuGln SEQ ID NO:10;

TABLE 3-continued

PROTEIN SEQUENCES pMON32323 .pep

AlaSerLysMetGlnGlyLeuLeuGluArgValAsnThrGluIleHisPheValThrLys
CysAlaPheGlnProProProSerCysLeuArgPheValGlnThrAsnIleSerArgLeu
LeuGlnGluThrSerGluGlnLeuValAlaLeuLysProTrpIleThrArgGlnAsnPhe
SerArgCysLeuGluLeuGlnCysGlnProAspSerSerThrLeuSerGlyGlyAsnGly
SerGlyGlyAsnGlySerGlyGlyAsnGlyThrGlnAspCysSerPheGlnHisSerPro
IleSerSerAspPheAlaValLysIleArgGluLeuSerAspTyrLeuLeuGlnAspTyr
ProValThrValAlaSerAsnLeuGlnAspGluGluLeuCysGlyGlyLeuTrpArgLeu
ValLeuAlaGlnArgTrpMetGluArgLeuLysThrValAlaGly SEQ ID NO:11;

pMON32324 .pep

AlaSerLysMetGlnGlyLeuLeuGluArgValAsnThrGluIleHisPheValThrLys
CysAlaPheGlnProProProSerCysLeuArgPheValGlnThrAsnIleSerArgLeu
LeuGlnGluThrSerGluGlnLeuValAlaLeuLysProTrpIleThrArgGlnAsnPhe
SerArgCysLeuGluLeuGlnCysGlnProAspSerSerThrLeuSerGlyGlyAsnGly
SerGlyGlyAsnGlyThrGlnAspCysSerPheGlnHisSerProIleSerSerAspPhe
AlaValLysIleArgGluLeuSerAspTyrLeuLeuGlnAspTyrProValThrValAla
SerAsnLeuGlnAspGluGluLeuCysGlyGlyLeuTrpArgLeuValLeuAlaGlnArg
TrpMetGluArgLeuLysThrValAlaGly SEQ ID NO:12;

pMON32325 .pep

AlaSerLysMetGlnGlyLeuLeuGluArgValAsnThrGluIleHisPheValThrLys
CysAlaPheGlnProProProSerCysLeuArgPheValGlnThrAsnIleSerArgLeu
LeuGlnGluThrSerGluGlnLeuValAlaLeuLysProTrpIleThrArgGlnAsnPhe
SerArgCysLeuGluLeuGlnCysGlnProAspSerSerThrLeuSerGlyGlyAsnGly
ThrGlnAspCysSerPheGlnHisSerProIleSerSerAspPheAlaValLysIleArg
GluLeuSerAspTyrLeuLeuGlnAspTyrProValThrValAlaSerAsnLeuGlnAsp
GluGluLeuCysGlyGlyLeuTrpArgLeuValLeuAlaGlnArgTrpMetGluArgLeu
LysThrValAlaGly SEQ ID NO:13;

pMON32326 .pep

AlaProProSerCysLeuArgPheValGlnThrAsnIleSerArgLeuLeuGlnGluThr
SerGluGlnLeuValAlaLeuLysProTrpIleThrArgGlnAsnPheSerArgCysLeu
GluLeuGlnCysGlnProAspSerSerThrLeuSerGlyGlyAsnGlySerGlyGlyAsn
GlySerGlyGlyAsnGlyThrGlnAspCysSerPheGlnHisSerProIleSerSerAsp
PheAlaValLysIleArgGluLeuSerAspTyrLeuLeuGlnAspTyrProValThrVal
AlaSerAsnLeuGlnAspGluGluLeuCysGlyGlyLeuTrpArgLeuValLeuAlaGln
ArgTrpMetGluArgLeuLysThrValAlaGlySerLysMetGlnGlyLeuLeuGluArg
ValAsnThrGluIleHisPheValThrLysCysAlaPheGlnPro SEQ ID NO:14;

pMON32327 .pep

AlaProProSerCysLeuArgPheValGlnThrAsnIleSerArgLeuLeuGlnGluThr
SerGluGlnLeuValAlaLeuLysProTrpIleThrArgGlnAsnPheSerArgCysLeu
GluLeuGlnCysGlnProAspSerSerThrLeuSerGlyGlyAsnGlySerGlyGlyAsn
GlyThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnPro SEQ ID NO:15;

pMON32328 .pep

AlaProProSerCysLeuArgPheValGlnThrAsnIleSerArgLeuLeuGlnGluThr
SerGluGlnLeuValAlaLeuLysProTrpIleThrArgGlnAsnPheSerArgCysLeu
GluLeuGlnCysGlnProAspSerSerThrLeuSerGlyGlyAsnGlyThrGlnAspCys
SerPheGlnHisSerProIleSerSerAspPheAlaValLysIleArgGluLeuSerAsp
TyrLeuLeuGlnAspTyrProValThrValAlaSerAsnLeuGlnAspGluGluLeuCys
GlyGlyLeuTrpArgLeuValLeuAlaGlnArgTrpMetGluArgLeuLysThrValAla
GlySerLysMetGlnGlyLeuLeuGluArgValAsnThrGluIleHisPheValThrLys
CysAlaPheGlnPro SEQ ID NO:16;

pMON32348 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuSerGlyGlySerGlySerGlyGlySerGlySerGlyGlySerGlyThrGlnAspCys
SerPheGlnHisSerProIleSerSerAspPheAlaValLysIleArgGluLeuSerAsp
TyrLeuLeuGlnAspTyrProValThrValAlaSerAsnLeuGln SEQ ID NO:17;

TABLE 3-continued

PROTEIN SEQUENCES pMON32350 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuSerGlyGlySerGlySerGlySerGlyThrGlnAspCysSerPheGlnHisSer
ProIleSerSerAspPheAlaValLysIleArgGluLeuSerAspTyrLeuLeuGlnAsp
TyrProValThrValAlaSerAsnLeuGln SEQ ID NO:18;

FLT3N .pep

MetAlaThrGlnAspCysSerPheGlnHisSerProIleSerSerAspPheAlaValLys
IleArgGluLeuSerAspTyrLeuLeuGlnAspTyrProValThrValAlaSerAsnLeu
GlnAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySer SEQ ID NO:19;

FLT3C .pep

GlySerGlyGlyThrGlnAspCysSerPheGlnHisSerProIleSerSerAspPheAla
ValLysIleArgGluLeuSerAspTyrLeuLeuGlnAspTyrProValThrValAlaSer
AsnLeuGlnAspGluGluLeuCysGlyGlyLeuTrpArgLeuValLeuAlaGlnArgTrp
MetGluArgLeuLysThrValAlaGlySerLysMetGlnGlyLeuLeuGluArgValAsn
ThrGluIleHisPheValThrLysCysAlaPheGlnProProProSerCysLeuArgPhe
ValGlnThrAsnIleSerArgLeuLeuGlnGluThrSerGluGlnLeuValAlaLeuLys
ProTrpIleThrArgGlnAsnPheSerArgCysLeuGluLeuGlnCysGlnProAspSer
SerThrLeu SEQ ID NO:20;

FLT7N .pep

MetAlaThrGlnAspCysSerPheGlnHisSerProIleSerSerAspPheAlaValLys
IleArgGluLeuSerAspTyrLeuLeuGlnAspTyrProValThrValAlaSerAsnLeu
GlnAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySer SEQ ID NO:21;

FLT4C .pep

GlySerGlyGlyGlyThrGlnAspCysSerPheGlnHisSerProIleSerSerAspPhe
AlaValLysIleArgGluLeuSerAspTyrLeuLeuGlnAspTyrProValThrValAla
SerAsnLeuGlnAspGluGluLeuCysGlyGlyLeuTrpArgLeuValLeuAlaGlnArg
TrpMetGluArgLeuLysThrValAlaGlySerLysMetGlnGlyLeuLeuGluArgVal
AsnThrGluIleHisPheValThrLysCysAlaPheGlnProProProSerCysLeuArg
PheValGlnThrAsnIleSerArgLeuLeuGlnGluThrSerGluGlnLeuValAlaLeu
LysProTrpIleThrArgGlnAsnPheSerArgCysLeuGluLeuGlnCysGlnProAsp
SerSerThrLeu SEQ ID NO:22;

FLT11N .pep

MetAlaThrGlnAspCysSerPheGlnHisSerProIleSerSerAspPheAlaValLys
IleArgGluLeuSerAspTyrLeuLeuGlnAspTyrProValThrValAlaSerAsnLeu
GlnAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySerGlyGlyGlySer SEQ ID NO:23;

FLT10C .pep

GlySerGlyGlyGlySerGlyGlyGlySerGlyThrGlnAspCysSerPheGlnHisSer
ProIleSerSerAspPheAlaValLysIleArgGluLeuSerAspTyrLeuLeuGlnAsp
TyrProValThrValAlaSerAsnLeuGlnAspGluGluLeuCysGlyGlyLeuTrpArg
LeuValLeuAlaGlnArgTrpMetGluArgLeuLysThrValAlaGlySerLysMetGln
GlyLeuLeuGluArgValAsnThrGluIleHisPheValThrLysCysAlaPheGlnPro
ProProSerCysLeuArgPheValGlnThrAsnIleSerArgLeuLeuGlnGluThrSer
GluGlnLeuValAlaLeuLysProTrpIleThrArgGlnAsnPheSerArgCysLeuGlu
LeuGlnCysGlnProAspSerSerThrLeu SEQ ID NO:24;

TABLE 3-continued

| PROTEIN SEQUENCES |
|---| pMON32365 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyThrGlnAspCysSerPheGlnHisSerProIleSerSer
AspPheAlaValLysIleArgGluLeuSerAspTyrLeuLeuGlnAspTyrProValThr
ValAlaSerAsnLeuGln SEQ ID NO:25;

pMON32366 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlyThrGlnAspCysSerPheGlnHisSerProIleSer
SerAspPheAlaValLysIleArgGluLeuSerAspTyrLeuLeuGlnAspTyrProVal
ThrValAlaSerAsnLeuGln SEQ ID NO:26;

pMON32367 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySerGlyGlyThrGlnAspCysSerPheGlnHisSer
ProIleSerSerAspPheAlaValLysIleArgGluLeuSerAspTyrLeuLeuGlnAsp
TyrProValThrValAlaSerAsnLeuGln SEQ ID NO:27;

pMON32368 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySerGlyGlyGlySerGlyThrGlnAspCysSerPhe
GlnHisSerProIleSerSerAspPheAlaValLysIleArgGluLeuSerAspTyrLeu
LeuGlnAspTyrProValThrValAlaSerAsnLeuGln SEQ ID NO:28;

pMON32369 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySerGlyGlyGlySerGlyGlyGlyThrGlnAspCys
SerPheGlnHisSerProIleSerSerAspPheAlaValLysIleArgGluLeuSerAsp
TyrLeuLeuGlnAspTyrProValThrValAlaSerAsnLeuGln SEQ ID NO:29;

pMON32370 .pep

AlaAspGluGluLeuCysGlyGlyLeuTrpArgLeuValLeuAlaGlnArgTrpMetGlu
ArgLeuLysThrValAlaGlySerLysMetGlnGlyLeuLeuGluArgValAsnThrGlu
IleHisPheValThrLysCysAlaPheGlnProProProSerCysLeuArgPheValGln
ThrAsnIleSerArgLeuLeuGlnGluThrSerGluGlnLeuValAlaLeuLysProTrp
IleThrArgGlnAsnPheSerArgCysLeuGluLeuGlnCysGlnProAspSerSerThr
LeuGlyGlyGlySerGlyGlyGlySerGlyGlyGlySerGlyGlyGlySerGlyGlyGly
SerGlyThrGlnAspCysSerPheGlnHisSerProIleSerSerAspPheAlaValLys
IleArgGluLeuSerAspTyrLeuLeuGlnAspTyrProValThrValAlaSerAsnLeu
Gln SEQ ID NO:30;

pMON35712 .pep

AlaAspTyrProValThrValAlaSerAsnLeuGlnAspGluGluLeuCysGlyGlyLeu
TrpArgLeuValLeuAlaGlnArgTrpMetGluArgLeuLysThrValAlaGlySerLys
MetGlnGlyLeuLeuGluArgValAsnThrGluIleHisPheValThrLysCysAlaPhe
GlnProProProSerCysLeuArgPheValGlnThrAsnIleSerArgLeuLeuGlnGlu
ThrSerGluGlnLeuValAlaLeuLysProTrpIleThrArgGlnAsnPheSerArgCys
LeuGluLeuGlnCysGlnProAspSerSerThrLeuGlyGlyGlySerGlyGlyGlySer
GlyGlyGlySerGlyGlyGlyThrGlnAspCysSerPheGlnHisSerProIleSerSer

TABLE 3-continued

PROTEIN SEQUENCES

AspPheAlaValLysIleArgGluLeuSerAspTyrLeuLeuGln SEQ ID NO:31;

pMON35713 .pep

AlaAlaSerAsnLeuGlnAspGluGluLeuCysGlyGlyLeuTrpArgLeuValLeuAla
GlnArgTrpMetGluArgLeuLysThrValAlaGlySerLysMetGlnGlyLeuLeuGlu
ArgValAsnThrGluIleHisPheValThrLysCysAlaPheGlnProProProSerCys
LeuArgPheValGlnThrAsnIleSerArgLeuLeuGlnGluThrSerGluGlnLeuVal
AlaLeuLysProTrpIleThrArgGlnAsnPheSerArgCysLeuGluLeuGlnCysGln
ProAspSerSerThrLeuGlyGlyGlySerGlyGlyGlySerGlyGlyGlySerGlyGly
GlyThrGlnAspCysSerPheGlnHisSerProIleSerSerAspPheAlaValLysIle
ArgGluLeuSerAspTyrLeuLeuGlnAspTyrProValThrVal SEQ ID NO:32;

pMON35714 .pep

AlaValAlaGlySerLysMetGlnGlyLeuLeuGluArgValAsnThrGluIleHisPhe
ValThrLysCysAlaPheGlnProProProSerCysLeuArgPheValGlnThrAsnIle
SerArgLeuLeuGlnGluThrSerGluGlnLeuValAlaLeuLysProTrpIleThrArg
GlnAsnPheSerArgCysLeuGluLeuGlnCysGlnProAspSerSerThrLeuGlyGly
GlySerGlyGlyGlySerGlyGlyGlySerGlyGlyGlyThrGlnAspCysSerPheGln
HisSerProIleSerSerAspPheAlaValLysIleArgGluLeuSerAspTyrLeuLeu
GlnAspTyrProValThrValAlaSerAsnLeuGlnAspGluGluLeuCysGlyGlyLeu
TrpArgLeuValLeuAlaGlnArgTrpMetGluArgLeuLysThr SEQ ID NO:33;

pMON35715 .pep

AlaSerLysMetGlnGlyLeuLeuGluArgValAsnThrGluIleHisPheValThrLys
CysAlaPheGlnProProProSerCysLeuArgPheValGlnThrAsnIleSerArgLeu
LeuGlnGluThrSerGluGlnLeuValAlaLeuLysProTrpIleThrArgGlnAsnPhe
SerArgCysLeuGluLeuGlnCysGlnProAspSerSerThrLeuGlyGlyGlySerGly
GlyGlySerGlyGlyGlySerGlyGlyGlyThrGlnAspCysSerPheGlnHisSerPro
IleSerSerAspPheAlaValLysIleArgGluLeuSerAspTyrLeuLeuGlnAspTyr
ProValThrValAlaSerAsnLeuGlnAspGluGluLeuCysGlyGlyLeuTrpArgLeu
ValLeuAlaGlnArgTrpMetGluArgLeuLysThrValAlaGly SEQ ID NO:34;

pMON35716 .pep

AlaProProSerCysLeuArgPheValGlnThrAsnIleSerArgLeuLeuGlnGluThr
SerGluGlnLeuValAlaLeuLysProTrpIleThrArgGlnAsnPheSerArgCysLeu
GluLeuGlnCysGlnProAspSerSerThrLeuGlyGlyGlySerGlyGlyGlySerGly
GlyGlySerGlyGlyGlyThrGlnAspCysSerPheGlnHisSerProIleSerSerAsp
PheAlaValLysIleArgGluLeuSerAspTyrLeuLeuGlnAspTyrProValThrVal
AlaSerAsnLeuGlnAspGluGluLeuCysGlyGlyLeuTrpArgLeuValLeuAlaGln
ArgTrpMetGluArgLeuLysThrValAlaGlySerLysMetGlnGlyLeuLeuGluArg
ValAsnThrGluIleHisPheValThrLysCysAlaPheGlnPro SEQ ID NO:35;

pMON35717 .pep

AlaArgPheValGlnThrAsnIleSerArgLeuLeuGlnGluThrSerGluGlnLeuVal
AlaLeuLysProTrpIleThrArgGlnAsnPheSerArgCysLeuGluLeuGlnCysGln
ProAspSerSerThrLeuGlyGlyGlySerGlyGlyGlySerGlyGlyGlySerGlyGly
GlyThrGlnAspCysSerPheGlnHisSerProIleSerSerAspPheAlaValLysIle
ArgGluLeuSerAspTyrLeuLeuGlnAspTyrProValThrValAlaSerAsnLeuGln
AspGluGluLeuCysGlyGlyLeuTrpArgLeuValLeuAlaGlnArgTrpMetGluArg
LeuLysThrValAlaGlySerLysMetGlnGlyLeuLeuGluArgValAsnThrGluIle
HisPheValThrLysCysAlaPheGlnProProProSerCysLeu SEQ ID NO:36;

pMON35718 .pep

AlaThrAsnIleSerArgLeuLeuGlnGluThrSerGluGlnLeuValAlaLeuLysPro
TrpIleThrArgGlnAsnPheSerArgCysLeuGluLeuGlnCysGlnProAspSerSer
ThrLeuGlyGlyGlySerGlyGlyGlySerGlyGlyGlySerGlyGlyGlyThrGlnAsp
CysSerPheGlnHisSerProIleSerSerAspPheAlaValLysIleArgGluLeuSer
AspTyrLeuLeuGlnAspTyrProValThrValAlaSerAsnLeuGlnAspGluGluLeu
CysGlyGlyLeuTrpArgLeuValLeuAlaGlnArgTrpMetGluArgLeuLysThrVal
AlaGlySerLysMetGlnGlyLeuLeuGluArgValAsnThrGluIleHisPheValThr
LysCysAlaPheGlnProProProSerCysLeuArgPheValGln SEQ ID NO:37;

Materials and Methods

Recombinant DNA Methods

Unless noted otherwise, all specialty chemicals were obtained from Sigma Co., (St. Louis, Mo.). Restriction endonucleases and T4 DNA ligase were obtained from New England Biolabs (Beverly, Mass.) or Boehringer Mannheim (Indianapolis, Ind.).

Transformation of E. coli Strains

E. coli strains, such as DH5α™ (Life Technologies, Gaithersburg, Md.) and TG1 (Amersham Corp., Arlington Heights, Ill.) are used for transformation of ligation reactions and are the source of plasmid DNA for transfecting mammalian cells. E. coli strains, such as MON105 and JM101, can be used for expressing the flt3 receptor agonist of the present invention in the cytoplasm or periplasmic space.

MON105 ATCC#55204: F–, lamda–,IN(rrnD, rrE)1, rpoD+, rpoH358

DH5α™: F–, phi80dlacZdeltaM15, delta(lacZYA-argF) U169, deoR, recA1, endaI, hsdR17(rk–,mk+), phoA, supE441amda–,thi-1, gyrA96, relA1

TG1: delta(lac-pro), supE, thi-1, hsdD5/F' (traD36, proA+B+, laciq, lacZdeltaM15)

DH5α™ Subcloning efficiency cells are purchased as competent cells and are ready for transformation using the manufacturer's protocol, while both *E. coli* strains TG1 and MON105 are rendered competent to take up DNA using a CaCl$_2$ method. Typically, 20 to 50 mL of cells are grown in LB medium (1% Bacto-tryptone, 0.5% Bacto-yeast extract, 150 mM NaCl) to a density of approximately 1.0 optical density unit at 600 nanometers (OD600) as measured by a Baush & Lomb Spectronic spectrophotometer (Rochester, N.Y.). The cells are collected by centrifugation and resuspended in one-fifth culture volume of CaCl$_2$ solution (50 mM CaCl$_2$, 10 mM Tris-Cl, pH 7.4) and are held at 4° C. for 30 minutes. The cells are again collected by centrifugation and resuspended in one-tenth culture volume of CaCl$_2$ solution. Ligated DNA is added to 0.2mL of these cells, and the samples are held at 4° C. for 1 hour. The samples are shifted to 42° C. for two minutes and 1mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C. Single colonies are picked, grown in LB supplemented with appropriate antibiotic for 6–16 hours at 37° C. with shaking. Colonies are picked and inoculated into LB plus appropriate antibiotic (100 ug/mL ampicillin or 75 ug/mL spectinomycin) and are grown at 37° C. while shaking. Before harvesting the cultures, 1 ul of cells are analyzed by PCR for the presence of a flt3 receptor agonist gene. The PCR is carried out using a combination of primers that anneal to the flt3 receptor agonist gene and/or vector. After the PCR is complete, loading dye is added to the sample followed by electrophoresis as described earlier. A gene has been ligated to the vector when a PCR product of the expected size is observed.

Methods for Creation of Genes With new N-terminus/C-terminus

Method I. Creation of Genes With new N-terminus/C-terminus which Contain a Linker Region.

Genes with new N-terminus/C-terminus which contain a linker region separating the original C-terminus and N-terminus can be made essentially following the method described in L. S. Mullins, et al *J. Am. Chem. Soc.* 116, 5529–5533 (1994). Multiple steps of polymerase chain reaction (PCR) amplifications are used to rearrange the DNA sequence encoding the primary amino acid sequence of the protein. The steps are illustrated in FIG. 2.

In the first step, the primer set ("new start" and "linker start") is used to create and amplify, from the original gene sequence, the DNA fragment ("Fragment Start") that contains the sequence encoding the new N-terminal portion of the new protein followed by the linker that connects the C-terminal and N-terminal ends of the original protein. In the second step, the primer set ("new stop" and "linker stop") is used to create and amplify, from the original gene sequence, the DNA fragment ("Fragment Stop") that encodes the same linker as used above, followed by the new C-terminal portion of the new protein. The "new start" and "new stop" primers are designed to include the appropriate restriction enzyme recognition sites which allow cloning of the new gene into expression plasmids. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and one ug of template DNA; and 1×PCR buffer, 200 uM dGTP, 200 uM dATP, 200 uM dTTP, 200 uM dCTP, 2.5 units AmpliTaq DNA polymerase and 2 mM MgCl$_2$. PCR reactions are performed in a Model 480 DNA thermal cycler (Perkin Elmer Corporation, Norwalk, Conn.).

"Fragment Start" and "Fragment Stop", which have complementary sequence in the linker region and the coding sequence for the two amino acids on both sides of the linker, are joined together in a third PCR step to make the full-length gene encoding the new protein. The DNA fragments "Fragment Start" and "Fragment Stop" are resolved on a 1% TAE gel, stained with ethidium bromide and isolated using a Qiaex Gel Extraction kit (Qiagen). These fragments are combined in equimolar quantities, heated at 70° C. for ten minutes and slow cooled to allow annealing through their shared sequence in "linker start" and "linker stop". In the third PCR step, primers "new start" and "new stop" are added to the annealed fragments to create and amplify the full-length new N-terminus/C-terminus gene. Typical PCR conditions are one cycle 95° C. melting for two minutes; 25 cycles 94° C. denaturation for one minute, 60° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and approximately 0.5 ug of DNA; and 1×PCR buffer, 200 uM dGTP, 200 uM DATP, 200 uM dTTP, 200 uM dCTP, 2.5 units AmpliTaq DNA polymerase and 2 mM MgCl$_2$. PCR reactions are purified using a Wizard PCR Preps kit (Promega).

Method II. Creation of Genes With new N-terminus/C-terminus Without a Linker Region.

New N-terminus/C-terminus genes without a linker joining the original N-terminus and C-terminus can be made using two steps of PCR amplification and a blunt end ligation. The steps are illustrated in FIG. 3. In the first step, the primer set ("new start" and "P-bl start") is used to create and amplify, from the original gene sequence, the DNA fragment ("Fragment Start") that contains the sequence encoding the new N-terminal portion of the new protein. In the second step, the primer set ("new stop" and "P-bl stop") is used to create and amplify, from the original gene sequence, the DNA fragment ("Fragment Stop") that contains the sequence encoding the new C-terminal portion of the new protein. The "new start" and "new stop" primers are designed to include appropriate restriction sites which allow cloning of the new gene into expression vectors. Typical PCR conditions are one cycle 95° C. melting for two minutes; 25 cycles 94° C. denaturation for one minute, 50° C. annealing for 45 seconds and 72° C. extension for 45 seconds. Deep Vent polymerase (New England Biolabs) is used to reduce the occurrence of overhangs in conditions recommended by the manufacturer. The "P-bl start" and "P-bl stop" primers are phosphorylated at the end to aid in the subsequent blunt end ligation of "Fragment Start" and "Fragment Stop" to each other. A 100 ul reaction contained 150 pmole of each primer and one ug of template DNA; and 1×Vent buffer (New England Biolabs), 300 uM dGTP, 300 uM DATP, 300 uM dTTP, 300 uM dCTP, and 1 unit Deep Vent polymerase. PCR reactions are performed in a Model 480 DNA thermal cycler (Perkin Elmer Corporation, Norwalk, Conn.). PCR reaction products are purified using a Wizard PCR Preps kit (Promega).

The primers are designed to include appropriate restriction enzyme recognition sites which allow for the cloning of the new gene into expression vectors. Typically "Fragment Start" is designed to create a NcoI restriction site , and "Fragment Stop" is designed to create a HindIII restriction site. Restriction digest reactions are purified using a Magic DNA Clean-up System kit (Promega). Fragments Start and Stop are resolved on a 1% TAE gel, stained with ethidium bromide and isolated using a Qiaex Gel Extraction kit (Qiagen). These fragments are combined with and annealed to the ends of the ~3800 base pair NcoI/HindIII vector fragment of pMON3934 by heating at 50° C. for ten minutes and allowed to slow cool. The three fragments are ligated together using T4 DNA ligase (Boehringer Mannheim). The result is a plasmid containing the full-length new N-terminus/C-terminus gene. A portion of the ligation reaction is used to transform E. coli strain DH5α cells (Life Technologies, Gaithersburg, Md.). Plasmid DNA is purified and sequence confirmed as below.

Method III. Creation of new N-terminus/C-terminus Genes by Tandem-duplication Method New N-terminus/C-terminus genes can be made based on the method described in R. A. Horlick, et al *Protein Eng.* 5:427–431 (1992). Polymerase chain reaction (PCR) amplification of the new N-terminus/C-terminus genes is performed using a tandemly duplicated template DNA. The steps are illustrated in FIG. 4.

The tandemly-duplicated template DNA is created by cloning and contains two copies of the gene separated by DNA sequence encoding a linker connecting the original C- and N-terminal ends of the two copies of the gene. Specific primer sets are used to create and amplify a full-length new N terminus/C-terminus gene from the tandemly-duplicated template DNA. These primers are designed to include appropriate restriction sites which allow for the cloning of the new gene into expression vectors. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer Gene-Amp PCR Core Reagents kit (Perkin Elmer Corporation, Norwalk, Conn.) is used. A 100 ul reaction contains 100 pmole of each primer and one ug of template DNA; and 1×PCR buffer, 200 uM dGTP, 200 uM DATP, 200 uM dTTP, 200 uM dCTP, 2.5 units AmpliTaq DNA polymerase and 2 mM $MgCl_2$. PCR reactions are performed in a Model. 480 DNA thermal cycler (Perkin Elmer Corporation, Norwalk, Conn.). PCR reactions are purified using a Wizard PCR Preps kit (Promega).

DNA Isolation and Characterization

Plasmid DNA can be isolated by a number of different methods and using commercially available kits known to those skilled in the art. A few such methods are shown herein. Plasmid DNA is isolated using the Promega Wizard™ Miniprep kit (Madison, Wis.), the Qiagen QIAwell Plasmid isolation kits (Chatsworth, Calif.) or Qiagen Plasmid Midi kit. These kits follow the same general procedure for plasmid DNA isolation. Briefly, cells are pelleted by centrifugation (5000×g), plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted with TE. After screening for the colonies with the plasmid of interest, the E. coli cells are inoculated into 50–100 mLs of LB plus appropriate antibiotic for overnight growth at 37° C. in an air incubator while shaking. The purified plasmid DNA is used for DNA sequencing, further restriction enzyme digestion, additional subcloning of DNA fragments and transfection into mammalian, E. coli or other cells.

Sequence Confirmation

Purified plasmid DNA is resuspended in $dH_2O$ and quantitated by measuring the absorbance at 260/280 nm in a Bausch and Lomb Spectronic 601 UV spectrometer. DNA samples are sequenced using ABI PRISIM™ DyeDeoxy™ terminator sequencing chemistry (Applied Biosystems Division of Perkin Elmer Corporation, Lincoln City, Calif.) kits (Part Number 401388 or 402078) according to the manufacturers suggested protocol usually modified by the addition of 5% DMSO to the sequencing mixture. Sequencing reactions are performed in a Model 480 DNA thermal cycler (Perkin Elmer Corporation, Norwalk, Conn.) following the recommended amplification conditions. Samples are purified to remove excess dye terminators with Centri-Sep™ spin columns (Princeton Separations, Adelphia, N.J.) and lyophilized. Fluorescent dye labeled sequencing reactions are resuspended in deionized formamide, and sequenced on denaturing 4.75% polyacrylamide-8M urea gels using an ABI Model 373A automated DNA sequencer. Overlapping DNA sequence fragments are analyzed and assembled into master DNA contigs using Sequencher DNA analysis software (Gene Codes Corporation, Ann Arbor, Mich.).

ExDression of flt3 Receptor Agonists in Mammalian Cells

Mammalian Cell Transfection/Production of Conditioned Media

The BHK-21 cell line can be obtained from the ATCC (Rockville, Md.). The cells are cultured in Dulbecco's modified Eagle media (DMEM/high-glucose), supplemented to 2mM (mM) L-glutamine and 10% fetal bovine serum (FBS). This formulation is designated BHK growth media. Selective media is BHK growth media supplemented with 453 units/mL hygromycin B (Calbiochem, San Diego, Calif.). The BHK-21 cell line was previously stably transfected with the HSV transactivating protein VP16, which transactivates the IE110 promoter found on the plasmid pMON3359 (See Hippenmeyer et al., *Bio/Technology*, pp.1037–1041, 1993). The VP16 protein drives expression of genes inserted behind the IE110 promoter. BHK-21 cells expressing the transactivating protein VP16 are designated BHK-VP16. The plasmid pMON1118 (See Highkin et al., *Poultry Sci.*, 70: 970–981, 1991) expresses the hygromycin resistance gene from the SV40 promoter. A similar plasmid is available from ATCC, pSV2-hph.

BHK-VP16 cells are seeded into a 60 millimeter (mm) tissue culture dish at $3 \times 10^5$ cells per dish 24 hours prior to transfection. Cells are transfected for 16 hours in 3 mL of "OPTIMEM"™ (Gibco-BRL, Gaithersburg, Md.) containing 10 ug of plasmid DNA containing the gene of interest, 3 ug hygromycin resistance plasmid, pMON1118, and 80 ug of Gibco-BRL "LIPOFECTAMINE"™ per dish. The media is subsequently aspirated and replaced with 3 mL of growth media. At 48 hours post-transfection, media from each dish is collected and assayed for activity (transient conditioned media). The cells are removed from the dish by trypsin-EDTA, diluted 1:10 and transferred to 100 mm tissue culture dishes containing 10 mL of selective media. After approximately 7 days in selective media, resistant cells grow into colonies several millimeters in diameter. The colonies are removed from the dish with filter paper (cut to approximately the same size as the colonies and soaked in trypsin/EDTA) and transferred to individual wells of a 24 well plate containing 1 mL of selective media. After the clones are grown to confluence, the conditioned media is re-assayed, and positive clones are expanded into growth media.

Expression of flt3 Receptor Agonists in *E. coli*

*E. coli* strain MON105 or JM101 harboring the plasmid of interest are grown at 37° C. in M9 plus casamino acids medium with shaking in a air incubator Model G25 from New Brunswick Scientific (Edison, N.J.). Growth is monitored at OD600 until it reaches a value of 1, at which time nalidixic acid (10 milligrams/mL) in 0.1 N NaOH is added to a final concentration of 50 $\mu$g/mL. The cultures are then shaken at 37° C. for three to four additional hours. A high degree of aeration is maintained throughout culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al. Molecular Cloning: A Laboratory Manual, 1982). The culture is centrifuged (5000×g) to pellet the cells.

Additional strategies for achieving high-level expression of genes in *E. coli* can be found in Savvas, C. M. (*Microbiological Reviews* 60;512–538, 1996).

Inclusion Body Preparation, Extraction, Refolding, Dialysis, DEAE Chromatography, and Characterization of the flt3 Receptor Agonists Which Accumulate as Inclusion Bodies in *E. coli*

Isolation of Inclusion Bodies:

The cell pellet from a 330 mL *E. coli* culture is resuspended in 15 mL of sonication buffer (10 mM 2-amino-2-(hydroxymethyl) 1,3-propanediol hydrochloride (Tris-HCl), pH 8.0+1 mM ethylenediaminetetraacetic acid (EDTA)). These resuspended cells are sonicated using the microtip probe of a Sonicator Cell Disruptor (Model W-375, Heat Systems-Ultrasonics, Inc., Farmingdale, N.Y.). Three rounds of sonication in sonication buffer followed by centrifugation are employed to disrupt the cells and wash the inclusion bodies (IB). The first round of sonication is a 3 minute burst followed by a 1 minute burst, and the final two rounds of sonication are for 1 minute each.

Extraction and refolding of proteins from inclusion body pellets:

Following the final centrifugation step, the IB pellet is resuspended in 10 mL of 50 mM Tris-HCl, pH 9.5, 8 M urea and 5 mM dithiothreitol (DTT) and stirred at room temperature for approximately 45 minutes to allow for denaturation of the expressed protein.

The extraction solution is transferred to a beaker containing 70 mL of 5mM Tris-HCl, pH 9.5 and 2.3 M urea and gently stirred while exposed to air at 4° C. for 18 to 48 hours to allow the proteins to refold. Refolding is monitored by analysis on a Vydac (Hesperia, Ca.) C18 reversed phase high pressure liquid chromatography (RP-HPLC) column (0.46× 25 cm). A linear gradient of 40% to 65% acetonitrile, containing 0.1% trifluoroacetic acid (TFA), is employed to monitor the refold. This gradient is developed over 30 minutes at a flow rate of 1.5 mL per minute. Denatured proteins generally elute later in the gradient than the refolded proteins.

Purification:

Following the refold, contaminating *E. coli* proteins are removed by acid precipitation. The pH of the refold solution is titrated to between pH 5.0 and pH 5.2 using 15% (v/v) acetic acid (HOAc). This solution is stirred at 4° C. for 2 hours and then centrifuged for 20 minutes at 12,000×g to pellet any insoluble protein.

The supernatant from the acid precipitation step is dialyzed using a Spectra/Por 3 membrane with a molecular weight cut off (MWCO) of 3,500 daltons. The dialysis is against 2 changes of 4 liters (a 50-fold excess) of 10 mM Tris-HCl, pH 8.0 for a total of 18 hours. Dialysis lowers the sample conductivity and removes urea prior to DEAE chromatography. The sample is then centrifuged (20 minutes at 12,000×g) to pellet any insoluble protein following dialysis.

A Bio-Rad Bio-Scale DEAE2 column (7×52 mm) is used for ion exchange chromatography. The column is equilibrated in a buffer containing 10 mM Tris-HCl, pH 8.0. The protein is eluted using a 0-to-500 mM sodium chloride (NaCl) gradient, in equilibration buffer, over 45 column volumes. A flow rate of 1 mL per minute is used throughout the run. Column fractions (2 mL per fraction) are collected across the gradient and analyzed by RP HPLC on a Vydac (Hesperia, Ca.) C18 column (0.46×25 cm). A linear gradient of 40% to 65% acetonitrile, containing 0.1% trifluoroacetic acid (TFA), is employed. This gradient is developed over 30 minutes at a flow rate of 1.5 mL per minute. Pooled fractions are then dialyzed against 2 changes of 4 liters (50-to-500-fold excess) of 10 mM ammonium acetate ($NH_4Ac$), pH 4.0 for a total of 18 hours. Dialysis is performed using a Spectra/Por 3 membrane with a MWCO of 3,500 daltons. Finally, the sample is sterile filtered using a 0.22 $\mu$m syringe filter (uStar LB syringe filter, Costar, Cambridge, Mass.), and stored at 4° C.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

Protein Characterization:

The purified protein is analyzed by RP-HPLC, electrospray mass spectrometry, and SDS-PAGE. The protein quantitation is done by amino acid composition, RP-HPLC, and Bradford protein determination. In some cases tryptic peptide mapping is performed in conjunction with electrospray mass spectrometry to confirm the identity of the protein.

Methylcellulose Assay

This assay reflects the ability of colony stimulating factors to stimulate normal bone marrow cells to produce different types of hematopoietic colonies in vitro (Bradley et al.,*Aust. Exp Biol. Sci.* 44:287–300, 1966), Pluznik et al., *J. Cell Comp. Physio* 66:319–324, 1965).

Methods Approximately 30 mL of fresh, normal, healthy bone marrow aspirate are obtained from individuals following informed consent. Under sterile conditions samples are diluted 1:5 with a 1×PBS (#14040.059 Life Technologies, Gaithersburg, MD.) solution in a 50 mL conical tube (#25339-50 Corning, Corning Md.). Ficoll (Histopaque 1077 Sigma H-8889) is layered under the diluted sample and centrifuged, 300×g for 30 min. The mononuclear cell band is removed and washed two times in 1×PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen. Cultures are set up in triplicate with a final volume of 1.0 mL in a 35×10 mm petri dish (Nunc#174926). Culture medium is purchased from Terry Fox Labs. (HCC-4230 medium (Terry Fox Labs, Vancouver, B.C., Canada) and erythropoietin (Amgen, Thousand Oaks, Calif.) is added to the culture media. 3,000–10,000 CD34+ cells are added per dish. FLT3 receptor agonist proteins, in conditioned media from transfected mammalian cells or purified from conditioned media from transfected mammalian cells or E. coli, are added to give final concentrations ranging from 0.001 nM to 10 nM. Cultures are resuspended using a 3cc syringe and 1.0 mL is dispensed per dish. Control (baseline response) cultures received no colony stimulating factors. Positive control cultures received conditioned media (PHA stimulated human cells: Terry Fox Lab. H2400). Cultures are incubated at 37° C., 5% $CO_2$ in humidified air.

Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., PNAS USA 89:4109–113, 1992; Mayani et al., Blood 81:3252–3258, 1993). In contrast to bone marrow, cord blood is more readily available on a regular basis. There is also a potential to reduce assay variability by pooling cells obtained fresh from several donors, or to create a bank of cryopreserved cells for this purpose.

Methods

Mononuclear cells (MNC) are isolated from cord blood within 24 hr. of collection, using a standard density gradient (1.077 g/mL Histopaque). Cord blood MNC have been further enriched for stem cells and progenitors by several procedures, including immunomagnetic selection for CD14–, CD34+ cells; panning for SBA–, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pM to 1204 pM) are prepared with 1×104 cells in 1ml of 0.9% methylcellulose containing medium without additional growth factors (Methocult H4230 from Stem Cell Technologies, Vancouver, BC.). In some experiments, Methocult H4330 containing erythropoietin (FLT3) was used instead of Methocult H4230, or Stem Cell Factor (SCF), 50 ng/mL (Biosource International, Camarillo, Calif.) was added. After culturing for 7–9 days, colonies containing >30 cells are counted.

MUTZ-2 Cell Proliferation Assay

A cell line such as MUTZ-2, which is a human myeloid leukemia cell line (German Collection of Microorganisms and Cell Cultures, DSM ACC 271), can be used to determine the cell proliferative activity of flt3 receptor agonists. MUTZ-2 cultures are maintained with recombinant native flt3 ligand (20–100 ng/mL) in the growth medium. Eighteen hours prior to assay set-up, MUTZ-2 cells are washed in IMDM medium (Gibco) three times and are resuspended in IMDM medium alone at a concentration of 0.5–0.7×10E6 cells/mL and incubated at 37° C. and 5%$CO_2$ to starve the cells of flt3 ligand. The day of the assay, standards and flt3 receptor agonists are diluted to two fold above desired final concentration in assay media in sterile tissue culture treated 96 well plates. Flt3 receptor agonists and standards are tested in triplicate. 50 $\mu$l of assay media is loaded into all wells except row A. 75 $\mu$l of the flt3 receptor agonists or standards are added to row A and 25 $\mu$l taken from that row and serial dilutions (1:3) performed on the rest of the plate (rows B through G). Row H remains as a media only control. The starved MUTZ-2 cells are washed two times in IMDM medium and resuspended in 50 $\mu$l assay media. 50 $\mu$l of cells are added to each well resulting in a final concentration of 0.25×10E6cells/mL. Assay plates containing cells are incubated at 37° C. and 5%$CO_2$ for 44hrs. Each well is then pulsed with 1 $\mu$Ci/well of tritiated thymidine in a volume of 20 $\mu$l for four hours. Plates are then harvested and counted.

Transfected Cell Lines:

Cell lines, such as BHK or the murine pro B cell line Baf/3, can be transfected with a colony stimulating factor receptor, such as the human flt3 receptor which the cell line does not have. These transfected cell lines can be used to determine the activity of the ligand of which the receptor has been transfected.

EXAMPLE 1

Isolation of cDNA Encoding flt3 Ligand

Three flt3 ligand clones were amplified from human bone morrow poly A+ RNA (Clontech) using NCOFLT, HIND160, and HIND165 PCR primers (according to the manufacturer's suggested conditions). These amplified PCR products were gel purified and cloned into the BHK expression vector pMON5723 generating pMON30237 (NCOFLT+HIND160), pMON30238 (NCOFLT+HIND165), and a deletion clone pMON30239 (NCOFLT+HIND165). The deletion in pMON30239 is of amino acid residues 89 through 106 (the numbering of the residues is based on the sequence of native flt3 ligand as shown in FIGS. 5a and 5b).

EXAMPLE 2

Sequence rearranged flt3 ligand were constructed using several methods and linker types. The first set of constructs containing the linker peptide (SerGlyGlyAsnGly(SEQ ID NO:46)X (where X=1, 2, or 3) with the breakpoints 39/40, 65/66, and 89/90 were made using a two step PCR process described by Mullins et al. in which the front half and the back half of each final sequence rearranged molecule is made separately in the first PCR step, then the paired products of the first reaction step are combined in a second PCR step and extended in the absence of exogenous primers.

For example, to make the three 89/90 breakpoint precursor molecules with the SerGlyGlyAsnGly SEQ ID NO:46, SerGlyGlyAsnGlySerGlyGlyAsnGly SEQ ID NO: 47, and SerGlyGlyAsnGlySerGlyGlyAsnGlySerGlyGlyAsnGly SEQ ID NO:48 amino acid linkers (pMON32326, pMON32327 and pMON32328 respectively), six initial PCR products were generated. The following primer pairs were used in the first step PCR reaction: a) 89For/L5B; b) 89For/L10B; c) 89For/L15B; d) 89Rev/L5A; e) 89Rev/L10A; and f) 89Rev/L15A. The identical approach was used to make pMON32321 (39/40 breakpoint, primer pairs 39For/L10B and 39Rev/L10A) and pMON32325 (65/66 breakpoint, primer pairs 65For/L5B and 65Rev/L5A) precursors. Except as noted below, all subsequent PCR reactions utilized the components of the PCR Optimizer Kit (Invitrogen) and amplification conditions according to the manufacturers suggested protocol. Reactions were set up as follows: 50 pmole of each primer, 10 ul of 5×Buffer B [300 mM Tris-HCl (pH 8.5), 10 mM $MgCl_2$, 75 mM (NH4) 2SO4], 5 U Taq polymerase, and 100 ng of heat denatured DNA (in this example pMON30238) template were combined, and brought to 45 ul final volume with $dH_2O$. Reactions were pre-incubated for 1–5 minute at 80° C., then 5 ul of 10 mM dNTP added to each reaction, and heat denatured for 2 minutes at 94° C. prior to amplification in a Perkin Elmer model 480 DNA thermal cycler. Seven DNA amplification cycles were done under the following conditions: heat denature for one minute at 94° C., two minutes annealing at 65° C., followed by a three minute extension at 72° C. Twenty three additional cycles consisting of a one minute heat denaturation at 94° C. followed by a four minute annealing/extension at 72° C. were done, followed by a final 7 minute extension cycle at 72° C. With the exception of pMON32328, the PCR amplification products were run out on a 1.2% TAE agarose gel, and the appropriate size bands (the major amplification product) were excised and purified using Geneclean II (Bio 101). Samples were resuspended in 10 ul $dH_2O$. The amplification products for pMON32328 were purified directly using a Wizard PCR Clean UP kit (Promega), and DNA eluted in 50 ul $dH_2O$.

The method to construct the precursors of pMON32322 (39/40 breakpoint, primer pairs 39For/L5B and 39Rev/L5A) was modified by increasing the amount of template to 1 ug, and by changing the PCR amplification conditions as follows: six cycles of 94° C., 1 minute, 65° C. for 2 minute, and 72° C. for 2½ minutes, followed by 15 cycles of 94° C. for 1 minute, 70° C. for 2 minutes, and 72° C. for 2 minutes, followed by a single 72° C. extension cycle for seven minutes.

The second PCR step utilized the gel-purified precursors from the first PCR step as a combination of primer/template as follows: 5 ul each of each precursor molecule (i.e. for pMON32328 the PCR products from primer pairs 89For/L5B and 89Rev/L5A), 10 ul of 5×Buffer B, 5 U of Taq polymerase, and 24 ul $dH_2O$. The reactions were heated for five minutes at 80° C., 5 ul of 10 mM DNTP was added, and the reactions heat denatured for 94° C. for two minutes. DNA amplification conditions were as follows: 15 cycles of 94° C. for one minute, 69° C. for two minutes, followed then by a three minute extension at 72° C. To allow for complete extension, the last cycle was followed by a single extension step at 72° C. for seven minutes. The 80 deg incubation time was reduced to two minutes and the number of cycles was decreased to ten cycles for pMON32325 (PCR products 65For/L5B and 65Rev/L5A). PCR reaction products of the appropriate size were gel purified on a 1.2% TAE agarose gel using Geneclean II. For pMON32322 (39For/L5B and 39Rev/L5A) the annealing temperature was reduced to 68° C., and the extension time reduced to two minutes. In addition, the PCR product was purified using a Wizard PCR Clean Up kit (Promega) according to the suppliers suggested protocol. The second PCR step was modified for pMON32326 (PCR products of 89For/L15B and 89Rev/L15A) as follows. Three sets of PCR reactions were set up identically as above, except for the sample buffer type (either 5X buffer B, D, or J—PCR Optimizer Kit). Composition of buffers D and J differ from buffer B only by pH or [$MgCl_2$]. The [$MgCl_2$] for buffer D is 3.5 mM, whereas the pH of buffer J is 9.5. The protocol was modified by increasing the number of PCR cycles 20, and 15 ul aliquots were withdrawn at the end of cycles 10, 15 and 20. Five uls of each aliquot timepoint were analyzed for the presence of amplified material on a 1.2% TBE agarose gel. The remainder of the buffer B, D, and J PCR reaction mixtures were pooled and subsequently purified using the Wizard PCR Clean Up Kit protocol. The DNA was eluted in 50 ul $dH_2O$.

The purified samples from the second step PCR reaction were digested with NcoI/HindIII using one of two standardized digestion conditions. For Geneclean II purified samples, 10 ul of DNA were digested in a 20 ul reaction with 7.5 U each of NcoI/HindIII for two hours at 37° C., and gel purified on a 1.1% TAE agarose gel again with Geneclean II. Ligation-ready samples were resuspended in 10 ul $dH_2O$. For pMON32322, 20 ul of sample was digested in a 50 ul reaction volume with 20U each of NcoI and HindIII for 3 hour at 37° C. 0.1 volume 3M NaOAc (pH 5.5) and 2.5 volume of EtOH were added, mixed, and stored at −20° C. overnight. The DNA was recovered by pelleting for 20 minutes at 13,000 rpm @ 4° C. in a Sigma Mk 202 microfuge. The DNA pellet was rinsed with chilled 70% EtOH, lyophilized, and resuspended in 10 ul $dH_2O$.

EXAMPLE 3

An alternate approach was used to construct pMON32320 (39/40 breakpoint, fifteen amino acid linker), pMON32323 (65/66 breakpoint, fifteen AA linker), and pMON32324 (65/66 breakpoint, ten amino acid linker). New primers (L15C, L15D, L15E) were designed to incorporate BamHI restriction site in the primer that was inframe to allow cloning into the BamHI site and maintain the proper reading frame. PCR reaction conditions for the first step were performed identically to that described for pMON32322, except that the following set of primer pairs were used: 65For/L15D and 65Rev/L15E (pMON32324); 39For/L15D and 39Rev/L15C (pMON32320); and 65For/L15D and 65Rev/L15C (pMON32323). The PCR reaction products were purified using a Wizard PCR Clean Up kit as described, and eluted in 50 ul dH2O. Samples were digested with either NcoI/BamHI (39For/L15D and 65For/L15D) or BamHI/HindIII (39Rev/L15C, 65Rev/L15C, and 65Rev/L15E). Restriction digests were performed as follows: 10 ul of purified PCR reaction products, 3 ul of 10×universal restriction buffer, 15 U of either NcoI or HindIII, 15 U of BamHI, in a final reaction volume of 30 ul. Reactions were incubated for 90 minutes at 37° C., and the PCR products gel purified on a 1.1% TAE agarose gel using Geneclean II. Ligation-ready DNA was resuspended in 10 ul $dH_2O$.

Inserts were ligated to NcoI/HindIII digested pMON3977 (BHK mammalian expression vector) that had been treated with shrimp alkaline phosphatase (SAP) either in a three way (pMON32320, pMON32323, or pMON32324) or a two way (pMON32321, pMON32322, pMON32325, pMON32326, pMON32327 and pMON32328) ligation reaction as follows: 2.5 ul of insert (2 ul of each primer pair amplicon for pMON32320, pMON32323, and pMON32324) was added to 50 ng of vector in a ten ul reaction using standard ligation conditions. Two ul of each reaction was transformed with 100 ul of chemically competent DH5α cells (Gibco/BRL) following the manufacturers suggested protocol. Twenty five ul and 200 ul aliquots were plated out on LB plates containing 50 ug/mL ampicillin and incubated overnight. Isolated colonies were picked and DNA prepared from 50 mL overnight cultures using Qiagen DNA midiprep kits. DNA was quantitated by absorbance at A260/A280, and verified for correct insert size by agarose gel electrophoresis following digestion of 1 ug template with NcoI/HindIII restriction endonucleases. Samples containing inserts of the predicted size were sequenced in both orientations using vector-specific primers using an automated fluorescent DNA sequencer model 373A (Perkin Elmer ABI). Sequencing reactions were done in 20 ul reaction volumes using a Perkin Elmer model 480 DNA thermal cycler as follows: one ug of template, 3.2 pmole primer, 1 ul DMSO, 9.5 ul Taq terminator dyedeoxy premix ( Perkin Elmer ABI) were combined, and subjected to 25 cycles of sequencing amplification as follows: 30 seconds at 94° C., 15 second annealing at 50° C., followed by a four minute extension cycle at 60° C. Samples were purified using Centri-Sep spin columns (Princeton Separations) following the manufacturers suggested protocol, lyophilized, and submitted for sequence analysis. Samples containing the predicted amino acid sequence were selected for analysis and assigned p MON numbers.

EXAMPLE 4

A similar approach used to construct pMON32320, pMON32323, and pMON32324 was utilized to introduce the second linker type (SerGlyGlySerGly)X where x=2 or 3, into two sequence rearranged flt3 receptor agonists containing the 39/40 breakpoint (pMON32348 and 32350). The primer pairs were as follows: for pMON32348 the combinations of 339For2/339Rev3 and 339Rev2/339-10For3 and for pMON32350 the combinations of 339For2/339Rev3 and 339Rev2/339-15For3 were used to create three PCR amplification products. Each PCR amplification was set up as follows: to 100 ng of heat denatured pMON32320, 50 pmole of each primer pair, 10 ul of 5×Buffer B, 5 U of Taq polymerase and $dH_2O$ was added to a final volume of 45 ul. Reactions were pre-incubated as described before. Fifteen amplification cycles were done under the following conditions: heat denature at 94° C., one minute, followed by a two minute annealing step at 70° C., and a three minute extension at 72° C. After the last cycle, a single 72 deg extension step of 7 minutes was done. The PCR amplification products of primer pairs 339For2/339Rev3, 339Rev2/339-10For3, and 339Rev2/339-15For2 were purified using a Wizard PCR Clean Up kit (Promega), and eluted in 50 ul $dH_2O$. NcoI/BamHI digests for the 339For2/339Rev3 primer pair as follows: 8 ul of DNA template was mixed with 2 ul universal restriction buffer and 10 U each of NcoI and BamHI in a 20 ul reaction volume, and incubated for 90 minutes at 37° C. The digestion products was purified using the Geneclean II direct purification protocol, and ligation ready DNA resuspended in 10 ul $dH_2O$. The restriction digests and subsequent purification for the 339Rev2/339-10For3 and 339Rev2/339-15For2 amplification products were done identically as described for the 339For2/339Rev3 amplicon, except that 10 U of HindIII was substituted for NcoI. Standard ligations were done by adding to 50 ng NcoI/HindIII/SAP-treated, gel purified pMON3977, 0.5 ul 339For2/Rev3 amplicon, 1 ul of either 339Rev2/339-10For3 (pMON32348) or 339Rev2/339-15For3 (pMON32350) amplicons, 5U T4 DNA ligase, and 1 ul 10 X ligase buffer in a 10 ul reaction volume for 60 minutes at ambient temperature. Subsequent steps leading to final DNA sequence confirmation were done as described above.

EXAMPLE 5

A third type of linker, with a variable (GlyGlyGlySer (SEQ ID NO:46)X repeat motif, was incorporated into another set of sequence rearranged flt3 receptor agonists from modularly constructed templates. These linker lengths were;

6 AA linker (GlyGlyGlySerGlyGly SEQ ID NO:51),

7 AA linker (GlyGlyGlySerGlyGlyGly SEQ ID NO:52),

10 AA linker (GlyGlyGlySerGlyGlyGlySerGlyGly SEQ ID NO:53)

13 AA linker (GlyGlyGlySerGlyGlyGlySerGlyGlyGlySerGly SEQ ID NO:54),

15 AA linker (GlyGlyGlySerGlyGlyGlySerGlyGlyGlySerGlyGlyGly SEQ ID NO:55) ; and

21 AA linker (GlyGlyGlySerGlyGlyGlySerGlyGlyGlySerGlyGly GlySerGlyGly GlySerGly SEQ ID NO:56) amino acid residues. These modular templates, each comprising a dimer of hflt3 ligand separated by a BamHI-containing linker of unique length, were constructed as follows. Six intermediate PLASMID templates, FL3N, FL7N, FL11N, FL3C, FL4C, and FL10C, were constructed by PCR using paired primers and pMON30238 as template using cycling conditions similar to those employed for pMON32322. Per reaction, 50 pmole of each primer was added to 100 ng of heat-denatured template and the reactions assembled as described for pMON32322. Cycle conditions were as follows: seven cycles of 94° C., one minute; two minutes at 65° C., and 2.5 minutes at 72° C.; followed by ten cycles of one minute at 94° C., two minutes at 70° C., and 2.5 minutes at 72° C. A single seven minute extension at 72° C. completed the cycling reactions. The primer pairs used to construct each intermediate were; N-term/FLN3 (FL3N); N-term/FLN7 (FL7N); N-term/FLN11 (FL11N); C term/FLC3 (FL3C); C-term/FLC4 (FL4C); and C-term/FLC10 (FL10C). The PCR amplification products were purified with Wizard PCR Clean Up kits (Promega) and eluted in 50 ul $dH_2O$. Purified DNA for the first subset, FL3N, FL7N, and FL11N, were digested with NcoI/BamHI, gel purified as described previously, and ligated to NcoI/BamHI/Sap-treated pSE420 vector DNA (Invitrogen). Intermediate templates of the second subset, FL3C, FL4C, and FL10C, were constructed in an identical manner except HindIII was utilized instead of NcoI. Subsequent steps leading to final DNA sequence confirmation were done as described above.

EXAMPLE 6

To make the next six templates, the two subsets of intermediates in pSE420 were digested with either NcoI/BamHI (FL3N, FL7N, FL11N-subset 1) or BamHI/HindIII (FL3C, FL4C, FL10C-subset 2) and gel purified using Geneclean II as described previously. One intermediate amplicon from each subset were ligated to NcoI/HindIII/SAP-treated pMON3977 per reaction and transformed in DH5α cells as described previously using the following combinations to generate specific linker lengths: six AA linker (FL3N and FL3C), seven AA linker (FL3N and FL4C), ten AA linker (FL7N and FL3C), thirteen AA linker (FL3N and FL10C), fifteen AA linker (FL11N and FL4C), and 21 AA linker (FL11N and FL10C). DNA was prepared 50 mL overnight cultures from single colonies from each of the six combination as described above, analyzed for correct insert size by NcoI/HindIII restriction analysis, and used as template.

Primer pairs 39For/39Rev (39/40 breakpoint); 65For/65Rev (65/66 breakpoint) and 89For/89Rev (89/90 breakpoint) were used to PCR amplify each templates as described for pMON32322, except 75 pmole of each primer was used. Amplification conditions were modified as follows: six cycles of 94° C. for one minute, 2 minutes at 70° C., 2.5 minutes at 72° C.; followed by nine cycles of 94° C. for one minute, and three minutes at 72° C. After the last cycle, a final extension of six minutes at 72° C. allowed ample time for full extension of products.

Samples were purified using a Wizard PCR Clean Up kit as described, and double digested with NcoI/HindIII. These amplification products were purified again using a Wizard PCR Clean Up kit. In addition, all six different linker length molecules for the 39/40 breakpoint were cloned into NcoI/HindIII/SAP-treated pMON3977 as single proteins (pMON32365, pMON32366, pMON32367, pMON32368, pMON32369 and 32370). Subsequent steps leading to final DNA sequence confirmation were done as described above.

EXAMPLE 7

Additional sequence rearranged Flt3 ligands were constructed using the dimer template intermediates previously described. For sequence rearranged Flt3 ligands having the fifteen amino acid linker (GlyGlyGlySer)$_3$GlyGlyGly SEQ ID NO:55, the dimer intermediates Flt4C.seq and Flt11N.seq were used as the template in the PCR reaction. Five new breakpoints corresponding to Flt3 ligand amino acid residues 28/29, 34/35, 62/63, 94/95, and 98/99, were constructed using a PCR based approach using a PCR Optimizer kit (Invitrogen) and the following primer pairs; FL29For/FL29Rev, FL35For/FL35Rev, FL63For/FL63Rev, FL95For/FL95Rev, FL99For/FL99Rev. Amplification conditions were as follows: seven cycles of 94° C. for 1', 62° C. for 2', and 2.5' at 70° C.; twelve cycles of 94° C. for 1', 68° C. for 2',and 70° C. for 2.5'; followed by a final cycle of 7' at 72° C. PCR products corresponding to the predicted insert size were digested to completion with NcoI and HindIII, and gel purified as described previously using Gene Clean II (Bio 101) following the manufacturers suggested protocol. Samples were resuspended in 10 ul final volume with $dH_2O$. Inserts were cloned as single genes into the mammalian expression vector pMON3977 (NcoI/HindIII/SAP treated) and designated pMON35712, pMON35713, pMON35714, pMON35715, pMON35716, pMON35717, pMON35718 respectively.

Additional techniques for the construction of the variant genes, recombinant protein expression , protein purification, protein characterization, biological activity determination can be found in WO 94/12639, WO 94/12638, WO 95/20976, WO 95/21197, WO 95/20977, WO 95/21254 and WO 96/23888 which are hereby incorporated by reference in their entirety.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

What is claimed is:

1. A human flt-3 receptor agonist polypeptide, comprising a modified flt-3 ligand amino acid sequence selected from the group consisting of:
   (a) the sequence of SEQ ID NO: 144; and
   (b) a polypeptide comprising residues 1–132 of SEQ ID NO: 144;
wherein said modification comprises the linear rearrangement of the sequences of (a) or (b); wherein the N-terminus is joined to the C-terminus directly or through a linker capable of joining the N-terminus to the C-terminus and new C- and N-termini are created between the amino acid residue pairs of SEQ ID NO: 144 selected from the group consisting of:
   28–29, 29–30, 30–31, 31–32, 32–33, 34–35, 36–37, 37–38, 38–39, 40–41, 41–42, 42–43, 64–65, 65–66, 66–67, 86–87, 88–89, 89–90, 90–91, 91–92, 92–93, 93–94, 94–95, 95–96, 96–97, 97–98, 98–99, 99–100, 100–101, 101–102, and 102–103; and
   wherein optionally said flt-3 receptor agonist polypeptide is immediately preceded by (methionine$^{-1}$), (alanine$^{-1}$) or (methionine$^{-2}$, alanine$^{-1}$).

2. The flt-3 receptor agonist polypeptide, as recited in claim 1, wherein said linker is selected from the group consisting of;

GlyGlyGlySer SEQ ID NO:38;
GlyGlyGlySerGlyGlyGlySer SEQ ID NO:39;
GlyGlyGlySerGlyGlyGlySerGlyGlyGlySer SEQ ID NO:40;
SerGlyGlySerGlyGlySer SEQ ID NO:41;
GluPheGlyAsnMet SEQ ID NO:42;
GluPheGlyGlyAsriMet SEQ ID NO:43;
GluPheGlyGlyAsnGlyGlyAsnMet SEQ ID NO:443
GlyGlySerAspMetAlaGly SEQ ID NO:45;
SerGlyGlyAsnGly SEQ ID NO:46;
SerGlyGlyAsnGlySerGlyGlyAsnGly SEQ ID NO:47;
SerGlyGlyAsnGlySerGlyGlyAsnGlySerGlyGlyAsnGly SEQ ID NO:48;
SerGlyGlySerGlySerGlyGlySerGly SEQ ID NO:49;
SerGlyGlySerGlySerGlyGlySerGlySerGlyGlySerGly SEQ ID NO:50;
GlyGlyGlySerGlyGly SEQ ID NO:51;
GlyGlyGlySerGlyGlyGly SEQ ID NO:52;
GlyGlyGlySerGlyGlyGlySerGlyGly SEQ ID NO:53;
GlyGlyGlySerGlyGlyGlySerGlyGlyGlySerGly SEQ ID NO:54;
GlyGlyGlySerGlyGlyGlySerGlyGlyGlySerGlyGlyGly SEQ ID NO:55;
GlyGlyGlySerGlyGlyGlySerGlyGlyGlySerGlyGlyGlySerGly GlyGlySerGlyGly SEQ ID NO:56;

GlyGlyGlySerGlyGlyGlySerGlyGlyGlySerGlyGlyGlySerGly GlyGlySerGlyGlyGlySerGly SEQ ID NO:148;
ProProProTrpSerProArgProLeuGlyAlaThrAlaProThrAlaGly GlnProProLeu SEQ ID NO:149;
ProProProTrpSerProArgProLeuGlyAlaThrAlaProThr SEQ ID NO:150; and
ValGluThrValPheHisArgValSerGlnAspGlyLeuLeuThrSer SEQ ID NO:151.

3. The flt-3 receptor agonist polypeptide, as recited in claim 1, selected from the group consisting of;

AlaAspGluGluLeuCysGlyLeuTrpArgLeuValLeuAlaGlnArgTrpMETGlu ArgLeuLysThrValAlaGlySerLys- METGlnGlyLeuLeuGluArgValAsnThrGlu IleHisPheValThrLysCysAlaPheGlnProProProSerCysLeuArgpheValGln ThrAsnIleSerArgLeuLeuGln- GluThrSerGluGlnLeuValAlaLeuLysProTrp IleThrArgGlnAsnPheSerArgCysLeuGluLeuGlnCysGlnProAspSerSerThr LeuSerGlyGlyAsnGlySerGlyGlyAsnGlySerGlyGlyAsnGlyThrGlnAspCys SerPheGlnHisSerProIleSerSerAspPheAlaValLysIleArgGluLeuSerAsp TyrLeuLeuGlnAspTyrProValThrValAlaSerAsnLeuGln SEQ ID NO:8;

AlaAspGluGluLeuCysGlyLeuTrpArgLeuValLeuAlaGlnArgTrpMETGlu ArgLeuLysThrValAlaGlySerLys- METGlnGlyLeuLeuGluArgValAsnThrGlu IleHisPheValThrLysCysAlaPheGlnProProProSerCysLeuArgPheValGln ThrAsnIleSerArgLeuLeuGln- GluThrSerGluGlnLeuValAlaLeuLysProTrp IleThrArgGlnAsnPheSerArgCysLeuGluLeuGlnCysGlnProAspSerSerThr LeuSerGlyGlyAsnGlySerGlyGlyAsnGlyThrGlnAspCysSerPheGlnHisSer ProIleSerSerAspPheAlaValLysIleArgGluLeuSerAspTyrLeuLeuGlnAsp TyrProValThrValAlaSerAsnLeuGln SEQ ID NO:9;

AlaAspGluGluLeuCysGlyLeuTrpArgLeuValLeuAlaGlnArgTrpMETGlu ArgLeuLysThrValAlaGlySerLys- METGlnGlyLeuLeuGluArgValAsnThrGlu IleHisPheValThrLysCysAlaPheGlnProProProSerCysLeuArgpheValGln ThrAsnIleSerArgLeuLeuGln- GluThrSerGluGlnLeuValAlaLeuLysProTrp IleThrArgGlnAsnPheSerArgCysLeuGluLeuGlnCysGlnProAspSerSerThr LeuSerGlyGlyAsnGlyThrGlnAsp-
CysSerPheGlnHisSerProIleSerSerAsp PheAlaValL-
ysIleArgGluLeuSerAspTyr-
LeuLeuGlnAspTyrProValThrVal AlaSerAsnLeuGln
SEQ ID NO:10;

AlaSerLysMETGlnGlyLeuLeuGlu-
ArgValAsnThrGluIleHisPheValThrLys CysAl-
aPheGlnProProProSerCysLeuArg-
PheValGlnThrAsnIleSerArgLeu
LeuGlnGluThrSerGluGlnLeuValA-
laLeuLysProTrpIleThrArgGlnAsnPhe SerArgCysLeu-
GluLeuGlnCysGlnProAspSerSer-
ThrLeuSerGlyGlyAsnGly
SerGlyGlyAsnGlySerGlyGlyAsnG-
lyThrGlnAspCysSerPheGlnHisSerPro IleSerSerAsp-
PheAlaValLysIleArgG-
luLeuSerAspTyrLeuLeuGlnAspTyr
ProValThrValAlaSerAsnLeuGl-
nAspGluGluLeuCysGlyGlyLeuTrpArgLeu
ValLeuAlaGlnArgTrpMETGluAr-
gLeuLysThrValAlaGly SEQ ID NO:11;

AlaSerLysMETGlnGlyLeuLeuGlu-
ArgValAsnThrGluIleHisPheValThrLys CysAl-
aPheGlnProProProSerCysLeuArg-
PheValGlnThrAsnIleSerArgLeu
LeuGlnGluThrSerGluGlnLeuValA-
laLeuLysProTrpIleThrArgGlnAsnphe SerArgCysLeu-
GluLeuGlnCysGlnProAspSerSer-
ThrLeuSerGlyGlyAsnGly
SerGlyGlyAsnGlyThrGlnAsp-
CysSerPheGlnHisSerProIleSerSerAspphe AlaValL-
ysIleArgGluLeuSerAspTyr-
LeuLeuGlnAspTyrProValThrValAla
SerAsnLeuGlnAspGluGluLeuCysG-
lyGlyLeuTrpArgLeuValLeuAlaGlnArg TrpMETGlu-
ArgLeuLysThrValAlaGly SEQ ID NO:12

AlaSerLysMETGlnGlyLeuLeuGlu-
ArgValAsnThrGluIleHisPheValThrLys CysAl-
aPheGlnProProProSerCysLeuArg-
PheValGlnThrAsnIleSerArgLeu
LeuGlnGluThrSerGluGlnLeuValA-
laLeuLysProTrpIleThrArgGlnAsnPhe SerArgCysLeu-
GluLeuGlnCysGlnProAspSerSer-
ThrLeuSerGlyGlyAsnGly
ThrGlnAspCysSerPheGlnHisSer-
ProIleSerSerAspPheAlaValLysIleArg GluLeuSerAsp-
TyrLeuLeuGlnAspTyrProValThr-
ValAlaSerAsnLeuGlnAsp
GluGluLeuCysGlyGlyLeuTrpAr-
gLeuValLeuAlaGlnArgTrpMETGluArgLeu LysThrV-
alAlaGly SEQ ID NO:13;

AlaProProSerCysLeuArgPheVal-
GlnThrAsnIleSerArgLeuLeuGlnGluThr SerGluGln-
LeuValAlaLeuLysProTrpI-
leThrArgGlnAsnPheSerArgCysLeu
GluLeuGlnCysGlnProAspSerSer-
ThrLeuSerGlyGlyAsnGlySerGlyGlyAsn GlySerGlyG-
lyAsnGlyThrGlnAspCysSer-
PheGlnHisSerProIleSerSerAsp
PheAlaValLysIleArgG-
luLeuSerAspTyrLeuLeuGlnAspTyrProValThrVal Ala-
SerAsnLeuGlnAspGluGluLeuCysG-
lyGlyLeuTrpArgLeuValLeuAlaGln
ArgTrpMETGluArgLeuLysThrValA-
laGlySerLysMETGlnGlyLeuLeuGluArg ValAsnThr-
GluIleHisPheValThrLysCysAlaPheGlnPro SEQ ID
NO:14;

AlaProProSerCysLeuArgPheVal-
GlnThrAsnIleSerArgLeuLeuGlnGluThr SerGluGln-
LeuValAlaLeuLysProTrpI-
leThrArgGlnAsnPheSerArgCysLeu
GluLeuGlnCysGlnProAspSerSer-
ThrLeuSerGlyGlyAsnGlySerGlyGlyAsn GlyThrGl-
nAspCysSerPheGlnHisSer-
ProIleSerSerAspPheAlaValLysIle
ArgGluLeuSerAspTyrLeuLeuGl-
nAspTyrProValThrValAlaSerAsnLeuGln AspGluG-
luLeuCysGlyGlyLeuTrpArgLeu-
ValLeuAlaGlnArgTrpMETGluArg
LeuLysThrValAlaGlySerLysMET-
GlnGlyLeuLeuGluArgValAsnThrGluIle HisPheValTh-
rLysCysAlaPheGlnPro SEQ ID NO:15;

AlaProProSerCysLeuArgPheVal-
GlnThrAsnIleSerArgLeuLeuGlnGluThr SerGluGln-
LeuValAlaLeuLysProTrpI-
leThrArgGlnAsnPheSerArgCysLeu
GluLeuGlnCysGlnProAspSerSer-
ThrLeuSerGlyGlyAsnGlyThrGlnAspCys SerPheGln-
HisSerProIleSerSerAspPheAla-
ValLysIleArgGluLeuSerAsp
TyrLeuLeuGlnAspTyrProValThr-
ValAlaSerAsnLeuGlnAspGluGluLeuCys GlyG-
lyLeuTrpArgLeuValLeuAla-
GlnArgTrpMETGluArgLeuLysThrValAla
GlySerLysMETGlnGlyLeuLeuGlu-
ArgValAsnThrGluIleHisPheValThrLys CysAl-
aPheGlnPro SEQ ID NO:16;

AlaAspTyrProValThrValAlaSer-
AsnLeuGlnAspGluGluLeuCysGlyGlyLeu TrpArgLeu-
ValLeuAlaGlnArgTrpMetGluAr-
gLeuLysThrValAlaGlySerLys
MetGlnGlyLeuLeuGluArgV-
alAsnThrGluIleHisPheValThrLysCysAlaPhe GlnPro-
ProProSerCysLeuArgPheVal-
GlnThrAsnIleSerArgLeuLeuGlnGlu
ThrSerGluGlnLeuValAlaLeu-
LysProTrpIleThrArgGlnAsnPheSerArgCys LeuG-
luLeuGlnCysGlnProAspSerSer-
ThrLeuGlyGlyGlySerGlyGlyGlySer
GlyGlyGlySerGlyGlyGlyThrGl-
nAspCysSerPheGlnHisSerProIleSerSer AspPheAla-
ValLysIleArgGluLeuSerAspTyrLeuLeuGln SEQ ID
NO:31;

AlaAlaSerAsnLeuGlnAspGluG-
luLeuCysGlyGlyLeuTrpArgLeuValLeuAla
GlnArgTrpMetGluArgLeuLysThr-
ValAlaGlySerLysMetGlnGlyLeuLeuGlu Argv-
alAsnThrGluIleHisPheValThrLy-
sCysAlaPheGlnProProProSerCys
LeuArgPheValGlnThrAsnIleSer-
ArgLeuLeuGlnGluThrSerGluGlnLeuVal AlaLeu-
LysProTrpIleThrArgGlnAsnPhe-
SerArgCysLeuGluLeuGlnCysGln
ProAspSerSerThrLeuGlyGlyGly-
SerGlyGlyGlySerGlyGlyGlySerGlyGly GlyThrGl-
nAspCysSerPheGlnHisSer-
ProIleSerSerAspPheAlaValLysIle
ArgGluLeuSerAspTyrLeuLeuGlnAspTyrProValThrVal
SEQ ID NO:32;

AlaValAlaGlySerLysMetGlnG-
lyLeuLeuGluArgValAsnThrGluIleHisPhe ValThrLy-
sCysAlaPheGlnProProProSer-
CysLeuArgPheValGlnThrAsnIle
SerArgLeuLeuGlnGluThrSer-

GluGlnLeuValAlaLeuLysProTrpIleThrArg GlnAsn-
PheSerArgCysLeuGluLeuGlnCys-
GlnProAspSerSerThrLeuGlyGly
GlySerGlyGlyGlySerGlyGlyGly-
SerGlyGlyGlyThrGlnAspCysSerPheGln HisSer-
ProIleSerSerAspPheAlaValL-
ysIleArgGluLeuSerAspTyrLeuLeu
GlnAspTyrProValThrValAlaSer-
AsnLeuGlnAspGluGluLeuCysGlyGlyLeu TrpArgLeu-
ValLeuAlaGlnArgTrpMetGluArgLeuLysThr SEQ ID
NO:33;

AlaSerLysMetGlnGlyLeuLeuGlu-
ArgValAsnThrGluIleHisPheValThrLys CysAl-
aPheGlnProProProSerCysLeuArg-
PhevalGlnThrAsnIleSerArgLeu
LeuGlnGluThrSerGluGlnLeuValA-
laLeuLysProTrpIleThrArgGlnAsnPhe SerArgCysLeu-
GluLeuGlnCysGlnProAspSerSer-
ThrLeuGlyGlyGlySerGly
GlyGlySerGlyGlyGlySerGlyGlyG-
lyThrGlnAspCysSerPheGlnHisSerPro IleSerSerAsp-
PheAlaValLysIleArgG-
luLeuSerAspTyrLeuLeuGlnAspTyr
ProValThrValAlaSerAsnLeuGl-
nAspGluGluLeuCysGlyGlyLeuTrpArgLeu
ValLeuAlaGlnArgTrpMetGluAr-
gLeuLysThrValAlaGly SEQ ID NO:34;

AlaProProSerCysLeuArgPheVal-
GlnThrAsnIleSerArgLeuLeuGlnGluThr SerGluGln-
LeuValAlaLeuLysProTrpI-
leThrArgGlnAsnPheSerArgCysLeu
GluLeuGlnCysGlnProAspSerSer-
ThrLeuGlyGlyGlySerGlyGlyGlySerGly GlyGlySerG-
lyGlyGlyThrGlnAspCysSer-
PheGlnHisSerProIleSerSerAsp
PheAlaValLysIleArgG-
luLeuSerAspTyrLeuLeuGlnAspTyrProValThrVal Ala-
SerAsnLeuGlnAspGluGluLeuCysG-
lyGlyLeuTrpArgLeuValLeuAlaGln
ArgTrpMetGluArgLeuLysThrValA-
laGlySerLysMetGlnGlyLeuLeuGluArg ValAsnThr-
GluIleHisPheValThrLysCysAlaPheGlnPro SEQ ID
NO:35;

AlaArgPheValGlnThrAsnIleSer-
ArgLeuLeuGlnGluThrSerGluGlnLeuVal AlaLeu-
LysProTrpIleThrArgGlnAsnPhe-
SerArgCysLeuGluLeuGlnCysGln
ProAspSerSerThrLeuGlyGlyGly-
SerGlyClyGlySerGlyGlyGlySerGlyGly GlyThrGl-
nAspCysSerPheGlnHisSer-
ProIleSerSerAspPheAlaValLysIle
ArgGluLeuSerAspTyrLeuLeuGl-
nAspTyrProValThrValAlaSerAsnLeuGln AspGluG-
luLeuCysGlyGlyLeuTrpArgLeu-
ValLeuAlaGlnArgTrpMetGluArg
LeuLysThrValAlaGlySerLysMet-
GlnGlyLeuLeuGluArgValAsnThrGluIle HisPheValTh-
rLysCysAlaPheGlnProProProSerCysLeu SEQ ID
NO:36;

AlaThrAsnIleSerArgLeuLeuGln-
GluThrSerGluGlnLeuValAlaLeuLysPro TrpIleThrArg-
GlnAsnPheSerArgCysLeuG-
luLeuGlnCysGlnProAspSerSer
ThrLeuGlyGlyGlySerGlyGlyGly-
SerGlyGlyGlySerGlyGlyGlyThrGlnAsp CysSer-
PheGlnHisSerProIleSerSerAsp-
PheAlaValLysIleArgGluLeuSer
AspTyrLeuLeuGlnAspTyrProV-
alThrValAlaSerAsnLeuGlnAspGluGluLeu CysGlyG-
lyLeuTrpArgLeuValLeuAla-
GlnArgTrpMetGluArgLeuLysThrVal
AlaGlySerLysMetGlnGlyLeuLeu-
GluArgValAsnThrGluIleHisPheValThr LysCysAl-
aPheGlnProProProSerCysLeuArgPheValGln SEQ ID
NO:37.

4. A nucleic acid molecule, comprising a sequence encoding the flt-3 receptor agonist polypeptide of claim 1.

5. A nucleic acid molecule, comprising a sequence encoding the flt-3 receptor agonist polypeptide of claim 2.

6. A nucleic acid molecule, comprising a sequence encoding the flt-3 receptor agonist polypeptide of claim 3.

7. A nucleic acid molecule, comprising a sequence encoding the flt-3 receptor agonist polypeptide of claim 6, selected from the group consisting of:

GCCGACGAGGAGCTCTGCGGGGGC-
CTCTGGCGGCTGGTCCTGGCACAGCG CTG-
GATGGAGCGGCTCAAGACT-
GTCGCTGGGTCCAAGATGCAAGGCTTGC
TGGAGCGCGTGAACACGGAGATA-
CACTTTGTCACCAAATGTGCCTTTCAG
CCCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCTG-
GAGGTAACGGATCCGGTGGCAATGG-
GAGCGGCGGAAATGGAAC
CCAGGACTGCTCCTTCCAACACAGC-
CCCATCTCCTCCGACTTCGCTGTCA AAATC-
CGTGAGCTGTCTGACTACCTGCTTCAA-
GATTACCCAGTCACCGTG
GCCTCCAACCTGCAG SEQ ID NO:113;

GCCGACGAGGAGCTCTGCGGGGGC-
CTCTGGCGGCTGGTCCTGGCACAGCG CTG-
GATGGAGCGGCTCAAGACT-
GTCGCTGGGTCCAAGATGCAAGGCTTGC
TGGAGCGCGTGAACACGGAGATA-
CACTTTGTCACCAAATGTGCCTTTCAG
CCCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCAG-
GCGGTAACGGCAGTGGAGGTAATGGCAC-
CCAGGACTGCTCCTT
CCAACACAGCCCCATCTCCTCCGACT-
TCGCTGTCAAAATCCGTGAGCTGT CTGACTAC-
CTGCTTCAAGATTACCCAGTCACCGTG-
GCCTCCAACCTGCAG SEQ ID NO:114;

GCCGACGAGGAGCTCTGCGGGGGC-
CTCTGGCGGCTGGTCCTGGCACAGCG CTG-
GATGGAGCGGCTCAAGACT-
GCTCGTGGGTCCAAGATGCAAGGCTTGC
TGGAGCGCGTGAACACGGAGATA-
CACTTTGTCACCAAATGTGCCTTTCAG
CCCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCTG-
GCGGCAACGGCACCCAGGACTGCTCCT-

TCCAACACAGCCCCAT
CTCCTCCGACTTCGCTGTCAAAATCCGT-
GAGCTGTCTGACTACCTGCTTC AAGATTAC-
CCAGTCACCGTGGCCTCCAACCTGCAG SEQ ID
NO:115;
GCCTCCAAGATGCAAGGCTTGCTG-
GAGCGCGTGAACACGGAGATACACTT TGT-
CACCAAATGTGCCTTTCAGC-
CCCCCCCAGCTGTCTTCGCTTCGTCC
AGACCAACATCTCCCGCCTCCTGCAG-
GAGACCTCCGAGCAGCTGGTGGCG CTGAAGC-
CCTGGATCACTCGCCAGAACTTCTCCCG-
GTGCCTGGAGCTGCA
GTGTCAGCCCGACTCCTCAACCCT-
GTCTGGAGGTAACGGATCCGGTGGCA ATGG-
GAGCGGCGGAAATGGAACCCAGGACT-
GCTCCTTCCAACACAGCCCC
ATCTCCTCCGACTTCGCTGTCAAAATC-
CGTGAGCTGTCTGACTACCTGCT TCAAGAT-
TACCCAGTCACCGTGGCCTCCAACCTG-
CAGGACGAGGAGCTCT
GCGGGGCCTCTGGCGGCTGGTCCTG-
GCACAGCGCTGGATGGAGCGGCTC AAGACT-
GTCGCTGGG SEQ ID NO:116;
GCCTCCAAGATGCAAGGCTTGCTG-
GAGCGCGTGAACACGGAGATACACTT TGT-
CACCAAATGTGCCTTTCAGC-
CCCCCCCAGCTGTCTTCGCTTCGTCC
AGACCAACATCTCCCGCCTCCTGCAG-
GAGACCTCCGAGCAGCTGGTGGCG CTGAAGC-
CCTGGATCACTCGCCAGAACTTCTCCCG-
GTGCCTGGAGCTGCA
GTGTCAGCCCGACTCCTCAACCCT-
GTCTGGAGGTAACGGATCCGGAGGTA ATG-
GCACCCAGGACTGCTCCTTCCAACA-
CAGCCCCATCTCCTCCGACTTC
GCTGTCAAAATCCGTGAGCTGTCTGAC-
TACCTGCTTCAAGATTACCCAGT CACCGTGGC-
CTCCAACCTGCAGGACGAGGAGCTCT-
GCGGGGCCTCTGGC
GGCTGGTCCTGGCACAGCGCTGGATG-
GAGCGGCTCAAGACTGTCGCTGGG SEQ ID
NO:117;
GCCTCCAAGATGCAAGGCTTGCTG-
GAGCGCGTGAACACGGAGATACACTT TGT-
CACCAAATGTGCCTTTCAGC-
CCCCCCCAGCTGTCTTCGCTTCGTCC
AGACCAACATCTCCCGCCTCCTGCAG-
GAGACCTCCGAGCAGCTGGTGGCG CTGAAGC-
CCTGGATCACTCGCCAGAACTTCTCCCG-
GTGCCTGGAGCTGCA
GTGTCAGCCCGACTCCTCAACCCT-
GTCTGGCGGCAACGGCACGCAGGACT GCTC-
CTTCCAACACAGCCCCATCTCCTC-
CGACTTCGCTGTCAAAATCCGT
GAGCTGTCTGACTACCTGCTTCAAGAT-
TACCCAGTCACCGTGGCCTCCAA CCTGCAG-
GACGAGGAGCTCTGCGGGGGCCTCTG-
GCGGCTGGTCCTGGCAC
AGCGCTGGATGGAGCGGCTCAAGACT-
GTCGCTGGG SEQ ID NO:118;
GCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCTG-
GAGGTAACGGCAGTGGTGGCAATGG-
GAGCGGTGGAAATGGAAC
CCAGGACTGCTCCTTCCAACACAGC-
CCCATCTCCTCCGACTTCGCTGTCA AAATC-
CGTGAGCTGTCTGACTACCTGCTTCAA-
GATTACCCAGTCACCGTG
GCCTCCAACCTGCAGGACGAGGAGCTCT-
GCGGGGGCCTCTGGCGGCTGGT CCTGGCA-
CAGCGCTGGATGGAGCGGCTCAAGACT-
GTCGCTGGGTCCAAGA
TGCAAGGCTTGCTGGAGCGCGTGAA-
CACGGAGATACACTTTGTCACCAAA TGTGC-
CTTTCAGCCC SEQ ID NO:119;
GCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCAG-
GCGGTAACGGCAGTGGAGGTAATGGCAC-
CCAGGACTGCTCCTT
CCAACACAGCCCCATCTCCTCCGACT-
TCGCTGTCAAAATCCGTGAGCTGT CTGACTAC-
CTGCTTCAAGATTACCCAGTCACCGTG-
GCCTCCAACCTGCAG
GACGAGGAGCTCTGCGGGGGCCTCTG-
GCGGCTGGTCCTGGCACAGCGCTG
GATGGAGCGGCTCAAGACT-
GTCGCTGGGTCCAAGATGCAAGGCTTGCTGG
AGCGCGTGAACACGGAGATACACTTTGT-
CACCAAATGTGCCTTTCAGCCC SEQ ID NO:120;
GCCCCCCCAGCTGTCTTCGCTTCGTC-
CAGACCAACATCTCCCGCCTCCT GCAG-
GAGACCTCCGAGCAGCTGGTGGCGCT-
GAAGCCCTGGATCACTCGCC
AGAACTTCTCCCGGTGCCTGGAGCTG-
CAGTGTCAGCCCGACTCCTCAACC CTGTCTG-
GCGGCAACGGCACGCAGGACTGCTCCT-
TCCAACACAGCCCCAT
CTCCTCCGACTTCGCTGTCAAAATCCGT-
GAGCTGTCTGACTACCTGCTTC AAGATTAC-
CCAGTCACCGTGGCCTCCAACCTGCAG-
GACGAGGAGCTCTGC
GGGGGCCTCTGGCGGCTGGTCCTGGCA-
CAGCGCTGGATGGAGCGGCTCAA GACT-
GTCGCTGGGTCCAAGATGCAAGGCT-
TGCTGGAGCGCGTGAACACGG
AGATACACTTTGTCACCAAATGTGC-
CTTTCAGCCC SEQ ID NO:121;
GCCGATTACCCAGTCACCGTGGCCTC-
CAACCTGCAGGACGAGGAGCCTGCCGGGG
GCCTCTGGCGGCTGGTCCTGGCA-
CAGCGCTGGATGGAGCGGCTCAAGACTGTCGC
TGGGTCCAAGATGCAAGGCTTGCTG-
GAGCGCGTGAACACGGAGATACACTTTGTC
ACCAAATGTGCCTTTCAGC-
CCCCCCCAGCTGTCTTCGCTTCGTCCA-
GACCAACA TCTCCGCCTCCTGCAGGAGAC-
CTCCGAGCAGCTGGTGGCGCTGAAGCCCTG
GAT CACTCGCCAGAACTTCTCCCGGTGCCTG-
GAGCTGCAGTGTCAGCCCGACTCCTCA
ACCCTGGGCGGTGGGTCAGGAGGTGGGT-
CAGGAGGTGGATCCGGAGGTGGCACCC
AGGACTGCTCCTTCCAACACAGC-
CCCATCTCCTCCGACTTCGCTGTCAAAATCCG
TGAGCTGTCTGACTACCTGCTTCAA SEQ ID
NO:136;

GCCGCCTCCAACCTGCAGGACGAG-
GAGCTCTGCGGGGGCCTCTGGCGGCTGGTCC
TGGCACAGCGCTGGATGGAGCGGCTCAA-
GACTGTCGCTGGGTCCAAGATGCAAGG
CTTGCTGGAGCGCGTGAACACGGAGATA-
CACTTTGTCACCAAATGTGCCTTTCAG
CCCCCCCCAGCTGTCTTCGCTTCGTC-
CAGACCAACATCTCCCGCCTCCTGCAGG
AGACCTCCGAGCAGCTGGTGGCGCT-
GAAGCCCTGGATCACTCGCCAGAACTTCTC
CCGGTGCCTGGAGCTGCAGTGTCAGC-
CCGACTCCTCAACCCTGGGCGGTGGGTCA
GGAGGTGGGTCAGGAGGTGGATCCGGAG-
GTGGCACCCAGGACTGCTCCTTCCAAC
ACAGCCCCATCTCCTCCGACTTCGCTGT-
CAAAATCCGTGAGCTGTCTGACTACCT GCT-
TCAAGATTACCCAGTCACCGTG SEQ ID NO:137;

GCCGTCGCTGGGTCCAAGATGCAAGGCT-
TGCTGGAGCGCGTGAACACGGAGATAC
ACTTTGTCACCAAATGTGCCTTTCAGC-
CCCCCCCAGCTGTCTTCGCTTCGTCCA GAC-
CAACATCTCCCGCCTCCTGCAGGAGAC-
CTCCGAGCAGCTGGTGGCGCTGAAG
CCCTGGATCACTCGCCAGAACTTCTC-
CCGGTGCCTGGAGCTGCAGTGTCAGCCCG
ACTCCTCAACCCTGGGCGGTGGGTCAG-
GAGGTGGGTCAGGAGGTGGATCCGGAGG
TGGCACCCAGGACTGCTCCTTCCAACA-
CAGCCCCATCTCCTCCGACTTCGCTGTC
AAAATCCGTGAGCTGTCTGACTACCT-
GCTTCAAGATTACCCAGTCACCGTGGCCT
CCAACCTGCAGGACGAGGAGCTCT-
GCGGGGCCTCTGGCGGCTGGTCCTGGCACA
GCGCTGGATGGAGCGGCTCAAGACT SEQ ID NO:138;

GCCTCCAAGATGCAAGGCTTGCTG-
GAGCGCGTGAACACGGAGATACACTTTGTCA
CCAAATGTGCCTTTCAGC-
CcCCCCCCCAGCTGTCTTCGCTTCGTC-
CAGACCAACAT CTCCCGCCTCCTGCAG-
GAGACCTCCGAGCAGCTGGTGGCGCTGAA
GCCCTGGATC ACTCGCCAGAACTTCTCCCGGT-
GCCTGGAGCTGCAGTGTCAGCCCGACTC-
CTCAA CCCTGGGCGGTGGGTCAGGAG-
GTGGGTCAGGAGGTGGATCCGGAGGTGGCACCCA
GGACTGCTCCTTCCAACACAGC-
CCCATCTCCTCCGACTTCGCTGTCAAAATCCGT
GAGCTGTCTGACTACCTGCTTCAAGAT-
TACCCAGTCACCGTGGCCTCCAACCTGC
AGGACGAGGAGCTCTGCGGGGGCCTCTG-
GCGGCTGGTCCTGGCACAGCGCTGGAT
GGAGCGGCTCAAGACTGTCGCTGGG SEQ ID NO:139;

GCCCCCCCCAGCTGTCTTCGCTTCGTC-
CAGACCAACATCTCCCGCCTCCTGCAGG
AGACCTCCGAGCAGCTGGTGGCGCT-
GAAGCCCTGGATCACTCGCCAGAACTTCTC
CCGGTGCCTGGAGCTGCAGTGTCAGC-
CCGACTCCTCAACCCTGGGCGGTGGGTCA
GGAGGTGGGTCAGGAGGTGGATCCGGAG-
GTGGCACCCAGGACTGCTCCTTCCAAC
ACAGCCCCATCTCCTCCGACTTCGCTGT-
CAAAATCCGTGAGCTGTCTGACTACCT GCT-
TCAAGATTACCCAGTCACCGTGGCCTC-
CAACCTGCAGGACGAGGAGCTCTGC
GGGGGCCTCTGGCGGCTGGTCCTGGCA-
CAGCGCTGGATGGAGCGGCTCAAGACTG
TCGCTGGGTCCAAGATGCAAGGCT-
TGCTGGAGCGCGTGAACACGGAGATACACTT
TGTCACCAAATGTGCCTTTCAGCCC SEQ ID NO:140;

GCCCGCTTCGTCCAGACCAACATCTC-
CCGCCTCCTGCAGGAGACCTCCGAGCAGC
TGGTGGCGCTGAAGCCCTGGAT-
CACTCGCCAGAACTTCTCCCGGTGCCTG-
GAGCT GCAGTGTCAGCCCGACTCCTCAAC-
CCTGGGCGGTGGGTCAGGAGGTGGGTCAGGA
GGTGGATCCGGAGGTGGCACCCAGGACT-
GCTCCTTCCAACACAGCCCCATCTCCT
CCGACTTCGCTGTCAAAATCCGTGAGCT-
GTCTGACTACCTGCTTCAAGATTACCC AGT-
CACCGTGGCCTCCAACCTGCAGGACGAG-
GAGCTCTGCGGGGGCCTCTGGCGG
CTGGTCCTGGCACAGCGCTGGATG-
GAGCGGCTCAAGACTGTCGCTGGGTCCAAGA
rTGCAAGGCTTGCTGGAGCGCGTGAA-
CACGGAGATACACTTTGTCACCAAATGTGC
CTTTCAGCCCCCCCCCAGCTGTCTT SEQ ID NO:142;

GCCACCAACATCTCCCGCCTCCTGCAG-
GAGACCTCCGAGCAGCTGGTGGCGCTGA AGC-
CCTGGATCACTCGCCAGAACTTCTCCCG-
GTGCCTGGAGCTGCAGTGTCAGCC
CGACTCCTCAACCCTGGGCGGTGGGT-
CAGGAGGTGGGTCAGGAGGTGGATCCGGA
GGTGGCACCCAGGACTGCTCCTTCCAA-
CACAGCCCCATCTCCTCCGACTTCGCTG
TCAAAATCCGTGAGCTGTCTGACTACCT-
GCTTCAAGATTACCCAGTCACCGTGGC CTC-
CAACCTGCAGGACGAGGAGCTCT-
GCGGGGGCCTCTGGCGGCTGGTCCTGGCA
CAGCGCTGGATGGAGCGGCTCAAGACT-
GTCGCTGGGTCCAAGATGCAAGGCTTGC
TGGAGCGCGTGAACACGGAGATA-
CACTTTGTCACCAAATGTGCCTTTCAGCCCCC
CCCCAGCTGTCTTCGCTTCGTCCAG SEQ ID NO:143.

8. A method of producing a flt3 receptor agonist polypeptide comprising: growing under suitable nutrient conditions, a host cell transformed or transfected with a replicable vector comprising said nucleic acid molecule of claim 4, 5, 6 or 7 in a manner allowing expression of said flt3 receptor agonist polypeptide and recovering said flt3 receptor agonist polypeptide.

9. A composition comprising; a polypeptide of claim 1, 2, or 3 and a pharmaceutically acceptable carrier.

10. A composition comprising; a polypeptide of claim 1, 2, or 3 a factor selected from the group consisting of: a colony stimulating factor, a cytokine, a lymphokine, an interleukin, and a hematopoietic growth factor; and a pharmaceutically acceptable carrier.

11. The composition according to claim 10 wherein said factor is selected from the group consisting of: GM-CSF, G-CSF, c-mpl ligand, M-CSF, IL-1, IL4, IL-2, IL-3, IL-5, IL-6, IL-7, IL-8, L-9, IL-10, IL-11, IL-12, IL-13, IL-15, LIF, flt3 ligand, and EPO.

* * * * *

SEQUENCE LISTING

```
(1) GENERAL INFORMATION:

(iii) NUMBER OF SEQUENCES: 151

(2) INFORMATION FOR SEQ ID NO:1:

(i) SEQUENCE CHARACTERISTICS:
          (A) LENGTH: 135 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:1:

Ala Thr Gln Asp Cys Ser Phe Gln His Ser Pro Ile Ser Ser Asp Phe
 1               5                  10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Ala Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
```

```
                65                  70                  75                  80
His Phe Val Thr Lys Cys Ala Phe Gln Pro Pro Ser Cys Leu Arg
                    85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro
                130                 135

(2) INFORMATION FOR SEQ ID NO:2:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

Ala Thr Gln Asp Cys Ser Phe Gln His Ser Pro Ile Ser Ser Asp Phe
 1               5                  10                  15

Ala Val Lys Ile Arg Glu Leu Ser Asp Tyr Leu Leu Gln Asp Tyr Pro
                20                  25                  30

Val Thr Val Ala Ser Asn Leu Gln Asp Glu Glu Leu Cys Gly Gly Leu
                35                  40                  45

Trp Arg Leu Val Leu Ala Gln Arg Trp Met Glu Arg Leu Lys Thr Val
                50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Ser Cys Leu Arg
                    85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro Asp Ser Ser Thr Leu
                130                 135                 140

(2) INFORMATION FOR SEQ ID NO:3:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Ala Thr Gln Asp Cys Ser Phe Gln His Ser Pro Ile Ser Ser Asp Phe
 1               5                  10                  15

Ala Val Lys Ile Arg Glu Leu Ser Asp Tyr Leu Leu Gln Asp Tyr Pro
                20                  25                  30

Val Thr Val Ala Ser Asn Leu Gln Asp Glu Glu Leu Cys Gly Gly Leu
                35                  40                  45

Trp Arg Leu Val Leu Ala Gln Arg Trp Met Glu Arg Leu Lys Thr Val
                50                  55                  60
```

```
Ala Gly Ser Lys Met Gln Gly Leu Leu Glu Arg Val Asn Thr Glu Ile
 65                  70                  75                  80

His Phe Val Thr Lys Cys Ala Phe Gln Glu Thr Ser Glu Gln Leu Val
                 85                  90                  95

Ala Leu Lys Pro Trp Ile Thr Arg Gln Asn Phe Ser Arg Cys Leu Glu
            100                 105                 110

Leu Gln Cys Gln Pro Asp Ser Ser Thr Leu
        115                 120
```

(2) INFORMATION FOR SEQ ID NO:4:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

```
Gly Thr Gln Asp Cys Ser Phe Gln His Ser Pro Ile Ser Ser Asp Phe
 1                   5                  10                  15

Ala Val Lys Ile Arg Glu Leu Ser Asp Tyr Leu Leu Gln Asp Tyr Pro
                 20                  25                  30

Val Thr Val Ala Ser Asn Leu Gln Asp Glu Glu Leu Cys Gly Gly Leu
            35                  40                  45

Trp Arg Leu Val Leu Ala Gln Arg Trp Met Glu Arg Leu Lys Thr Val
        50                  55                  60

Ala Gly Ser Lys Met Gln Gly Leu Leu Glu Arg Val Asn Thr Glu Ile
 65                  70                  75                  80

His Phe Val Thr Lys Cys Ala Phe Gln Pro Pro Pro Ser Cys Leu Arg
                 85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
            115                 120                 125

Leu Glu Leu Gln Cys Gln Pro
        130                 135
```

(2) INFORMATION FOR SEQ ID NO:5:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Gly Thr Gln Asp Cys Ser Phe Gln His Ser Pro Ile Ser Ser Asp Phe
 1                   5                  10                  15

Ala Val Lys Ile Arg Glu Leu Ser Asp Tyr Leu Leu Gln Asp Tyr Pro
                 20                  25                  30

Val Thr Val Ala Ser Asn Leu Gln Asp Glu Glu Leu Cys Gly Gly Leu
            35                  40                  45

Trp Arg Leu Val Leu Ala Gln Arg Trp Met Glu Arg Leu Lys Thr Val
        50                  55                  60

Ala Gly Ser Lys Met Gln Gly Leu Leu Glu Arg Val Asn Thr Glu Ile
 65                  70                  75                  80
```

-continued

```
His Phe Val Thr Lys Cys Ala Phe Gln Pro Pro Ser Cys Leu Arg
                85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro Asp Ser Ser Thr Leu
130                 135                 140
```

(2) INFORMATION FOR SEQ ID NO:6:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
Ala Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
                20                  25                  30

Val Thr Val Ala Ser Asn Leu Gln Asp Glu Glu Leu Cys Gly Gly Leu
                35                  40                  45

Trp Arg Leu Val Leu Ala Gln Arg Trp Met Glu Arg Leu Lys Thr Val
        50                  55                  60

Ala Gly Ser Lys Met Gln Gly Leu Leu Glu Arg Val Asn Thr Glu Ile
65              70                  75                  80

His Phe Val Thr Lys Cys Ala Phe Gln Pro Pro Ser Cys Leu Arg
                85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro
130                 135
```

(2) INFORMATION FOR SEQ ID NO:7:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

```
Ala Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
                20                  25                  30

Val Thr Val Ala Ser Asn Leu Gln Asp Glu Glu Leu Cys Gly Gly Leu
                35                  40                  45

Trp Arg Leu Val Leu Ala Gln Arg Trp Met Glu Arg Leu Lys Thr Val
        50                  55                  60

Ala Gly Ser Lys Met Gln Gly Leu Leu Glu Arg Val Asn Thr Glu Ile
```

```
                 65                  70                  75                  80
His Phe Val Thr Lys Cys Ala Phe Gln Pro Pro Ser Cys Leu Arg
                        85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro Asp Ser Ser Thr Leu
        130                 135                 140
```

(2) INFORMATION FOR SEQ ID NO:8:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Ala Asp Glu Glu Leu Cys Gly Gly Leu Trp Arg Leu Val Leu Ala Gln
 1               5                  10                  15

Arg Trp Met Glu Arg Leu Lys Thr Val Ala Gly Ser Lys Met Gln Gly
                20                  25                  30

Leu Leu Glu Arg Val Asn Thr Glu Ile His Phe Val Thr Lys Cys Ala
            35                  40                  45

Phe Gln Pro Pro Pro Ser Cys Leu Arg Phe Val Gln Thr Asn Ile Ser
    50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

Asp Ser Ser Thr Leu Ser Gly Gly Asn Gly Ser Gly Gly Asn Gly Ser
                100                 105                 110

Gly Gly Asn Gly Thr Gln Asp Cys Ser Phe Gln His Ser Pro Ile Ser
        115                 120                 125

Ser Asp Phe Ala Val Lys Ile Arg Glu Leu Ser Asp Tyr Leu Leu Gln
        130                 135                 140

Asp Tyr Pro Val Thr Val Ala Ser Asn Leu Gln
145                 150                 155
```

(2) INFORMATION FOR SEQ ID NO:9:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Ala Asp Glu Glu Leu Cys Gly Gly Leu Trp Arg Leu Val Leu Ala Gln
 1               5                  10                  15

Arg Trp Met Glu Arg Leu Lys Thr Val Ala Gly Ser Lys Met Gln Gly
                20                  25                  30

Leu Leu Glu Arg Val Asn Thr Glu Ile His Phe Val Thr Lys Cys Ala
            35                  40                  45
```

-continued

```
Phe Gln Pro Pro Pro Ser Cys Leu Arg Phe Val Gln Thr Asn Ile Ser
 50                  55                  60

Arg Leu Leu Gln Glu Thr Ser Glu Gln Leu Val Ala Leu Lys Pro Trp
 65                  70                  75                  80

Ile Thr Arg Gln Asn Phe Ser Arg Cys Leu Glu Leu Gln Cys Gln Pro
                 85                  90                  95

Asp Ser Ser Thr Leu Ser Gly Gly Asn Gly Ser Gly Asn Gly Thr
                100                 105                 110

Gln Asp Cys Ser Phe Gln His Ser Pro Ile Ser Ser Asp Phe Ala Val
            115                 120                 125

Lys Ile Arg Glu Leu Ser Asp Tyr Leu Leu Gln Asp Tyr Pro Val Thr
130                 135                 140

Val Ala Ser Asn Leu Gln
145                 150

(2) INFORMATION FOR SEQ ID NO:10:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

Ala Asp Glu Glu Leu Cys Gly Gly Leu Trp Arg Leu Val Leu Ala Gln
 1                   5                  10                  15

Arg Trp Met Glu Arg Leu Lys Thr Val Ala Gly Ser Lys Met Gln Gly
                 20                  25                  30

Leu Leu Glu Arg Val Asn Thr Glu Ile His Phe Val Thr Lys Cys Ala
             35                  40                  45

Phe Gln Pro Pro Pro Ser Cys Leu Arg Phe Val Gln Thr Asn Ile Ser
 50                  55                  60

Arg Leu Leu Gln Glu Thr Ser Glu Gln Leu Val Ala Leu Lys Pro Trp
 65                  70                  75                  80

Ile Thr Arg Gln Asn Phe Ser Arg Cys Leu Glu Leu Gln Cys Gln Pro
                 85                  90                  95

Asp Ser Ser Thr Leu Ser Gly Gly Asn Gly Thr Gln Asp Cys Ser Phe
                100                 105                 110

Gln His Ser Pro Ile Ser Ser Asp Phe Ala Val Lys Ile Arg Glu Leu
            115                 120                 125

Ser Asp Tyr Leu Leu Gln Asp Tyr Pro Val Thr Val Ala Ser Asn Leu
130                 135                 140

Gln
145

(2) INFORMATION FOR SEQ ID NO:11:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

Ala Ser Lys Met Gln Gly Leu Leu Glu Arg Val Asn Thr Glu Ile His
 1                   5                  10                  15
```

```
Phe Val Thr Lys Cys Ala Phe Gln Pro Pro Ser Cys Leu Arg Phe
            20                  25                  30

Val Gln Thr Asn Ile Ser Arg Leu Leu Gln Glu Thr Ser Glu Gln Leu
            35                  40                  45

Val Ala Leu Lys Pro Trp Ile Thr Arg Gln Asn Phe Ser Arg Cys Leu
 50                  55                  60

Glu Leu Gln Cys Gln Pro Asp Ser Ser Thr Leu Ser Gly Gly Asn Gly
 65                  70                  75                  80

Ser Gly Gly Asn Gly Ser Gly Gly Asn Gly Thr Gln Asp Cys Ser Phe
                 85                  90                  95

Gln His Ser Pro Ile Ser Ser Asp Phe Ala Val Lys Ile Arg Glu Leu
            100                 105                 110

Ser Asp Tyr Leu Leu Gln Asp Tyr Pro Val Thr Val Ala Ser Asn Leu
            115                 120                 125

Gln Asp Glu Glu Leu Cys Gly Gly Leu Trp Arg Leu Val Leu Ala Gln
            130                 135                 140

Arg Trp Met Glu Arg Leu Lys Thr Val Ala Gly
145                 150                 155

(2) INFORMATION FOR SEQ ID NO:12:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

Ala Ser Lys Met Gln Gly Leu Leu Glu Arg Val Asn Thr Glu Ile His
 1                   5                  10                  15

Phe Val Thr Lys Cys Ala Phe Gln Pro Pro Ser Cys Leu Arg Phe
            20                  25                  30

Val Gln Thr Asn Ile Ser Arg Leu Leu Gln Glu Thr Ser Glu Gln Leu
            35                  40                  45

Val Ala Leu Lys Pro Trp Ile Thr Arg Gln Asn Phe Ser Arg Cys Leu
 50                  55                  60

Glu Leu Gln Cys Gln Pro Asp Ser Ser Thr Leu Ser Gly Gly Asn Gly
 65                  70                  75                  80

Ser Gly Gly Asn Gly Thr Gln Asp Cys Ser Phe Gln His Ser Pro Ile
                 85                  90                  95

Ser Ser Asp Phe Ala Val Lys Ile Arg Glu Leu Ser Asp Tyr Leu Leu
            100                 105                 110

Gln Asp Tyr Pro Val Thr Val Ala Ser Asn Leu Gln Asp Glu Glu Leu
            115                 120                 125

Cys Gly Gly Leu Trp Arg Leu Val Leu Ala Gln Arg Trp Met Glu Arg
            130                 135                 140

Leu Lys Thr Val Ala Gly
145                 150

(2) INFORMATION FOR SEQ ID NO:13:

(i) SEQUENCE CHARACTERISTICS:
        (A) LENGTH: 145 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:13:

Ala Ser Lys Met Gln Gly Leu Leu Glu Arg Val Asn Thr Glu Ile His
1               5                   10                  15

Phe Val Thr Lys Cys Ala Phe Gln Pro Pro Ser Cys Leu Arg Phe
            20                  25                  30

Val Gln Thr Asn Ile Ser Arg Leu Leu Gln Glu Thr Ser Glu Gln Leu
        35                  40                  45

Val Ala Leu Lys Pro Trp Ile Thr Arg Gln Asn Phe Ser Arg Cys Leu
    50                  55                  60

Glu Leu Gln Cys Gln Pro Asp Ser Ser Thr Leu Ser Gly Gly Asn Gly
65                  70                  75                  80

Thr Gln Asp Cys Ser Phe Gln His Ser Pro Ile Ser Ser Asp Phe Ala
            85                  90                  95

Val Lys Ile Arg Glu Leu Ser Asp Tyr Leu Leu Gln Asp Tyr Pro Val
                100                 105                 110

Thr Val Ala Ser Asn Leu Gln Asp Glu Glu Leu Cys Gly Gly Leu Trp
            115                 120                 125

Arg Leu Val Leu Ala Gln Arg Trp Met Glu Arg Leu Lys Thr Val Ala
        130                 135                 140

Gly
145

(2) INFORMATION FOR SEQ ID NO:14:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Ala Pro Pro Ser Cys Leu Arg Phe Val Gln Thr Asn Ile Ser Arg Leu
1               5                   10                  15

Leu Gln Glu Thr Ser Glu Gln Leu Val Ala Leu Lys Pro Trp Ile Thr
            20                  25                  30

Arg Gln Asn Phe Ser Arg Cys Leu Glu Leu Gln Cys Gln Pro Asp Ser
        35                  40                  45

Ser Thr Leu Ser Gly Gly Asn Gly Ser Gly Gly Asn Gly Ser Gly Gly
    50                  55                  60

Asn Gly Thr Gln Asp Cys Ser Phe Gln His Ser Pro Ile Ser Ser Asp
65                  70                  75                  80

Phe Ala Val Lys Ile Arg Glu Leu Ser Asp Tyr Leu Leu Gln Asp Tyr
            85                  90                  95

Pro Val Thr Val Ala Ser Asn Leu Gln Asp Glu Glu Leu Cys Gly Gly
                100                 105                 110

Leu Trp Arg Leu Val Leu Ala Gln Arg Trp Met Glu Arg Leu Lys Thr
            115                 120                 125

Val Ala Gly Ser Lys Met Gln Gly Leu Leu Glu Arg Val Asn Thr Glu
        130                 135                 140

Ile His Phe Val Thr Lys Cys Ala Phe Gln Pro
145                 150                 155

(2) INFORMATION FOR SEQ ID NO:15:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

```
Ala Pro Pro Ser Cys Leu Arg Phe Val Gln Thr Asn Ile Ser Arg Leu
 1               5                  10                  15

Leu Gln Glu Thr Ser Glu Gln Leu Val Ala Leu Lys Pro Trp Ile Thr
             20                  25                  30

Arg Gln Asn Phe Ser Arg Cys Leu Glu Leu Gln Cys Gln Pro Asp Ser
         35                  40                  45

Ser Thr Leu Ser Gly Gly Asn Gly Ser Gly Asn Gly Thr Gln Asp
     50                  55                  60

Cys Ser Phe Gln His Ser Pro Ile Ser Ser Asp Phe Ala Val Lys Ile
65                  70                  75                  80

Arg Glu Leu Ser Asp Tyr Leu Leu Gln Asp Tyr Pro Val Thr Val Ala
                 85                  90                  95

Ser Asn Leu Gln Asp Glu Glu Leu Cys Gly Gly Leu Trp Arg Leu Val
             100                 105                 110

Leu Ala Gln Arg Trp Met Glu Arg Leu Lys Thr Val Ala Gly Ser Lys
         115                 120                 125

Met Gln Gly Leu Leu Glu Arg Val Asn Thr Glu Ile His Phe Val Thr
     130                 135                 140

Lys Cys Ala Phe Gln Pro
145                 150
```

(2) INFORMATION FOR SEQ ID NO:16:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

```
Ala Pro Pro Ser Cys Leu Arg Phe Val Gln Thr Asn Ile Ser Arg Leu
 1               5                  10                  15

Leu Gln Glu Thr Ser Glu Gln Leu Val Ala Leu Lys Pro Trp Ile Thr
             20                  25                  30

Arg Gln Asn Phe Ser Arg Cys Leu Glu Leu Gln Cys Gln Pro Asp Ser
         35                  40                  45

Ser Thr Leu Ser Gly Gly Asn Gly Thr Gln Asp Cys Ser Phe Gln His
     50                  55                  60

Ser Pro Ile Ser Ser Asp Phe Ala Val Lys Ile Arg Glu Leu Ser Asp
65                  70                  75                  80

Tyr Leu Leu Gln Asp Tyr Pro Val Thr Val Ala Ser Asn Leu Gln Asp
                 85                  90                  95

Glu Glu Leu Cys Gly Gly Leu Trp Arg Leu Val Leu Ala Gln Arg Trp
             100                 105                 110

Met Glu Arg Leu Lys Thr Val Ala Gly Ser Lys Met Gln Gly Leu Leu
         115                 120                 125
```

Glu Arg Val Asn Thr Glu Ile His Phe Val Thr Lys Cys Ala Phe Gln
130                 135                 140

Pro
145

(2) INFORMATION FOR SEQ ID NO:17:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

Ala Asp Glu Glu Leu Cys Gly Gly Leu Trp Arg Leu Val Leu Ala Gln
1               5                   10                  15

Arg Trp Met Glu Arg Leu Lys Thr Val Ala Gly Ser Lys Met Gln Gly
            20                  25                  30

Leu Leu Glu Arg Val Asn Thr Glu Ile His Phe Val Thr Lys Cys Ala
        35                  40                  45

Phe Gln Pro Pro Pro Ser Cys Leu Arg Phe Val Gln Thr Asn Ile Ser
    50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

Asp Ser Ser Thr Leu Ser Gly Gly Ser Gly Ser Gly Ser Gly Ser Ser
            100                 105                 110

Gly Gly Ser Gly Thr Gln Asp Cys Ser Phe Gln His Ser Pro Ile Ser
        115                 120                 125

Ser Asp Phe Ala Val Lys Ile Arg Glu Leu Ser Asp Tyr Leu Leu Gln
    130                 135                 140

Asp Tyr Pro Val Thr Val Ala Ser Asn Leu Gln
145                 150                 155

(2) INFORMATION FOR SEQ ID NO:18:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

Ala Asp Glu Glu Leu Cys Gly Gly Leu Trp Arg Leu Val Leu Ala Gln
1               5                   10                  15

Arg Trp Met Glu Arg Leu Lys Thr Val Ala Gly Ser Lys Met Gln Gly
            20                  25                  30

Leu Leu Glu Arg Val Asn Thr Glu Ile His Phe Val Thr Lys Cys Ala
        35                  40                  45

Phe Gln Pro Pro Pro Ser Cys Leu Arg Phe Val Gln Thr Asn Ile Ser
    50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

```
Asp Ser Ser Thr Leu Ser Gly Gly Ser Gly Ser Gly Gly Ser Gly Thr
            100                 105                 110

Gln Asp Cys Ser Phe Gln His Ser Pro Ile Ser Ser Asp Phe Ala Val
            115                 120                 125

Lys Ile Arg Glu Leu Ser Asp Tyr Leu Leu Gln Asp Tyr Pro Val Thr
            130                 135                 140

Val Ala Ser Asn Leu Gln
145                 150

(2) INFORMATION FOR SEQ ID NO:19:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

Met Ala Thr Gln Asp Cys Ser Phe Gln His Ser Pro Ile Ser Ser Asp
1               5                   10                  15

Phe Ala Val Lys Ile Arg Glu Leu Ser Asp Tyr Leu Leu Gln Asp Tyr
            20                  25                  30

Pro Val Thr Val Ala Ser Asn Leu Gln Asp Glu Glu Leu Cys Gly Gly
            35                  40                  45

Leu Trp Arg Leu Val Leu Ala Gln Arg Trp Met Glu Arg Leu Lys Thr
    50                  55                  60

Val Ala Gly Ser Lys Met Gln Gly Leu Leu Glu Arg Val Asn Thr Glu
65                  70                  75                  80

Ile His Phe Val Thr Lys Cys Ala Phe Gln Pro Pro Ser Cys Leu
                85                  90                  95

Arg Phe Val Gln Thr Asn Ile Ser Arg Leu Leu Gln Glu Thr Ser Glu
            100                 105                 110

Gln Leu Val Ala Leu Lys Pro Trp Ile Thr Arg Gln Asn Phe Ser Arg
            115                 120                 125

Cys Leu Glu Leu Gln Cys Gln Pro Asp Ser Ser Thr Leu Gly Gly Gly
    130                 135                 140

Ser
145

(2) INFORMATION FOR SEQ ID NO:20:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

Gly Ser Gly Gly Thr Gln Asp Cys Ser Phe Gln His Ser Pro Ile Ser
1               5                   10                  15

Ser Asp Phe Ala Val Lys Ile Arg Glu Leu Ser Asp Tyr Leu Leu Gln
            20                  25                  30

Asp Tyr Pro Val Thr Val Ala Ser Asn Leu Gln Asp Glu Glu Leu Cys
            35                  40                  45

Gly Gly Leu Trp Arg Leu Val Leu Ala Gln Arg Trp Met Glu Arg Leu
```

-continued

```
            50                  55                  60
Lys Thr Val Ala Gly Ser Lys Met Gln Gly Leu Leu Glu Arg Val Asn
 65                  70                  75                  80

Thr Glu Ile His Phe Val Thr Lys Cys Ala Phe Gln Pro Pro Pro Ser
                 85                  90                  95

Cys Leu Arg Phe Val Gln Thr Asn Ile Ser Arg Leu Leu Gln Glu Thr
                100                 105                 110

Ser Glu Gln Leu Val Ala Leu Lys Pro Trp Ile Thr Arg Gln Asn Phe
                115                 120                 125

Ser Arg Cys Leu Glu Leu Gln Cys Gln Pro Asp Ser Ser Thr Leu
                130                 135                 140
```

(2) INFORMATION FOR SEQ ID NO:21:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

```
Met Ala Thr Gln Asp Cys Ser Phe Gln His Ser Pro Ile Ser Ser Asp
 1                   5                  10                  15

Phe Ala Val Lys Ile Arg Glu Leu Ser Asp Tyr Leu Leu Gln Asp Tyr
                 20                  25                  30

Pro Val Thr Val Ala Ser Asn Leu Gln Asp Glu Glu Leu Cys Gly Gly
                 35                  40                  45

Leu Trp Arg Leu Val Leu Ala Gln Arg Trp Met Glu Arg Leu Lys Thr
 50                  55                  60

Val Ala Gly Ser Lys Met Gln Gly Leu Leu Glu Arg Val Asn Thr Glu
 65                  70                  75                  80

Ile His Phe Val Thr Lys Cys Ala Phe Gln Pro Pro Ser Cys Leu
                 85                  90                  95

Arg Phe Val Gln Thr Asn Ile Ser Arg Leu Leu Gln Glu Thr Ser Glu
                100                 105                 110

Gln Leu Val Ala Leu Lys Pro Trp Ile Thr Arg Gln Asn Phe Ser Arg
                115                 120                 125

Cys Leu Glu Leu Gln Cys Gln Pro Asp Ser Ser Thr Leu Gly Gly Gly
                130                 135                 140

Ser Gly Gly Ser
145
```

(2) INFORMATION FOR SEQ ID NO:22:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

```
Gly Ser Gly Gly Gly Thr Gln Asp Cys Ser Phe Gln His Ser Pro Ile
 1                   5                  10                  15

Ser Ser Asp Phe Ala Val Lys Ile Arg Glu Leu Ser Asp Tyr Leu Leu
                 20                  25                  30
```

```
Gln Asp Tyr Pro Val Thr Val Ala Ser Asn Leu Gln Asp Glu Glu Leu
            35                  40                  45

Cys Gly Gly Leu Trp Arg Leu Val Leu Ala Gln Arg Trp Met Glu Arg
 50                  55                  60

Leu Lys Thr Val Ala Gly Ser Lys Met Gln Gly Leu Leu Glu Arg Val
 65                  70                  75                  80

Asn Thr Glu Ile His Phe Val Thr Lys Cys Ala Phe Gln Pro Pro Pro
                 85                  90                  95

Ser Cys Leu Arg Phe Val Gln Thr Asn Ile Ser Arg Leu Leu Gln Glu
                100                 105                 110

Thr Ser Glu Gln Leu Val Ala Leu Lys Pro Trp Ile Thr Arg Gln Asn
            115                 120                 125

Phe Ser Arg Cys Leu Glu Leu Gln Cys Gln Pro Asp Ser Ser Thr Leu
130                 135                 140

(2) INFORMATION FOR SEQ ID NO:23:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Met Ala Thr Gln Asp Cys Ser Phe Gln His Ser Pro Ile Ser Ser Asp
 1               5                  10                  15

Phe Ala Val Lys Ile Arg Glu Leu Ser Asp Tyr Leu Leu Gln Asp Tyr
            20                  25                  30

Pro Val Thr Val Ala Ser Asn Leu Gln Asp Glu Glu Leu Cys Gly Gly
            35                  40                  45

Leu Trp Arg Leu Val Leu Ala Gln Arg Trp Met Glu Arg Leu Lys Thr
 50                  55                  60

Val Ala Gly Ser Lys Met Gln Gly Leu Leu Glu Arg Val Asn Thr Glu
 65                  70                  75                  80

Ile His Phe Val Thr Lys Cys Ala Phe Gln Pro Pro Ser Cys Leu
                 85                  90                  95

Arg Phe Val Gln Thr Asn Ile Ser Arg Leu Leu Gln Glu Thr Ser Glu
                100                 105                 110

Gln Leu Val Ala Leu Lys Pro Trp Ile Thr Arg Gln Asn Phe Ser Arg
            115                 120                 125

Cys Leu Glu Leu Gln Cys Gln Pro Asp Ser Ser Thr Leu Gly Gly Gly
130                 135                 140

Ser Gly Gly Gly Ser Gly Gly Gly Ser
145                 150

(2) INFORMATION FOR SEQ ID NO:24:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Gly Ser Gly Gly Gly Ser Gly Gly Gly Ser Gly Thr Gln Asp Cys Ser
 1               5                  10                  15
```

```
Phe Gln His Ser Pro Ile Ser Ser Asp Phe Ala Val Lys Ile Arg Glu
         20                  25                  30

Leu Ser Asp Tyr Leu Leu Gln Asp Tyr Pro Val Thr Val Ala Ser Asn
         35                  40                  45

Leu Gln Asp Glu Glu Leu Cys Gly Gly Leu Trp Arg Leu Val Leu Ala
         50                  55                  60

Gln Arg Trp Met Glu Arg Leu Lys Thr Val Ala Gly Ser Lys Met Gln
 65              70                  75                  80

Gly Leu Leu Glu Arg Val Asn Thr Glu Ile His Phe Val Thr Lys Cys
                 85                  90                  95

Ala Phe Gln Pro Pro Pro Ser Cys Leu Arg Phe Val Gln Thr Asn Ile
                100                 105                 110

Ser Arg Leu Leu Gln Glu Thr Ser Glu Gln Leu Val Ala Leu Lys Pro
        115                 120                 125

Trp Ile Thr Arg Gln Asn Phe Ser Arg Cys Leu Glu Leu Gln Cys Gln
        130                 135                 140

Pro Asp Ser Ser Thr Leu
145              150

(2) INFORMATION FOR SEQ ID NO:25:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

Ala Asp Glu Glu Leu Cys Gly Gly Leu Trp Arg Leu Val Leu Ala Gln
 1               5                  10                  15

Arg Trp Met Glu Arg Leu Lys Thr Val Ala Gly Ser Lys Met Gln Gly
         20                  25                  30

Leu Leu Glu Arg Val Asn Thr Glu Ile His Phe Val Thr Lys Cys Ala
         35                  40                  45

Phe Gln Pro Pro Pro Ser Cys Leu Arg Phe Val Gln Thr Asn Ile Ser
         50                  55                  60

Arg Leu Leu Gln Glu Thr Ser Glu Gln Leu Val Ala Leu Lys Pro Trp
 65              70                  75                  80

Ile Thr Arg Gln Asn Phe Ser Arg Cys Leu Glu Leu Gln Cys Gln Pro
                 85                  90                  95

Asp Ser Ser Thr Leu Gly Gly Gly Ser Gly Gly Thr Gln Asp Cys Ser
                100                 105                 110

Phe Gln His Ser Pro Ile Ser Ser Asp Phe Ala Val Lys Ile Arg Glu
        115                 120                 125

Leu Ser Asp Tyr Leu Leu Gln Asp Tyr Pro Val Thr Val Ala Ser Asn
        130                 135                 140

Leu Gln
145

(2) INFORMATION FOR SEQ ID NO:26:

(i) SEQUENCE CHARACTERISTICS:
        (A) LENGTH: 147 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:26:

```
Ala Asp Glu Glu Leu Cys Gly Gly Leu Trp Arg Leu Val Leu Ala Gln
1               5                   10                  15

Arg Trp Met Glu Arg Leu Lys Thr Val Ala Gly Ser Lys Met Gln Gly
            20                  25                  30

Leu Leu Glu Arg Val Asn Thr Glu Ile His Phe Val Thr Lys Cys Ala
        35                  40                  45

Phe Gln Pro Pro Pro Ser Cys Leu Arg Phe Val Gln Thr Asn Ile Ser
    50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

Asp Ser Ser Thr Leu Gly Gly Gly Ser Gly Gly Gly Thr Gln Asp Cys
                100                 105                 110

Ser Phe Gln His Ser Pro Ile Ser Ser Asp Phe Ala Val Lys Ile Arg
            115                 120                 125

Glu Leu Ser Asp Tyr Leu Leu Gln Asp Tyr Pro Val Thr Val Ala Ser
    130                 135                 140

Asn Leu Gln
145
```

(2) INFORMATION FOR SEQ ID NO:27:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

```
Ala Asp Glu Glu Leu Cys Gly Gly Leu Trp Arg Leu Val Leu Ala Gln
1               5                   10                  15

Arg Trp Met Glu Arg Leu Lys Thr Val Ala Gly Ser Lys Met Gln Gly
            20                  25                  30

Leu Leu Glu Arg Val Asn Thr Glu Ile His Phe Val Thr Lys Cys Ala
        35                  40                  45

Phe Gln Pro Pro Pro Ser Cys Leu Arg Phe Val Gln Thr Asn Ile Ser
    50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

Asp Ser Ser Thr Leu Gly Gly Gly Ser Gly Gly Gly Ser Gly Gly Thr
                100                 105                 110

Gln Asp Cys Ser Phe Gln His Ser Pro Ile Ser Ser Asp Phe Ala Val
            115                 120                 125

Lys Ile Arg Glu Leu Ser Asp Tyr Leu Leu Gln Asp Tyr Pro Val Thr
        130                 135                 140

Val Ala Ser Asn Leu Gln
145                 150
```

(2) INFORMATION FOR SEQ ID NO:28:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

```
Ala Asp Glu Glu Leu Cys Gly Gly Leu Trp Arg Leu Val Leu Ala Gln
  1               5                  10                  15

Arg Trp Met Glu Arg Leu Lys Thr Val Ala Gly Ser Lys Met Gln Gly
             20                  25                  30

Leu Leu Glu Arg Val Asn Thr Glu Ile His Phe Val Thr Lys Cys Ala
         35                  40                  45

Phe Gln Pro Pro Pro Ser Cys Leu Arg Phe Val Gln Thr Asn Ile Ser
     50                  55                  60

Arg Leu Leu Gln Glu Thr Ser Glu Gln Leu Val Ala Leu Lys Pro Trp
 65                  70                  75                  80

Ile Thr Arg Gln Asn Phe Ser Arg Cys Leu Glu Leu Gln Cys Gln Pro
                 85                  90                  95

Asp Ser Ser Thr Leu Gly Gly Gly Ser Gly Gly Ser Gly Gly Gly Gly
            100                 105                 110

Ser Gly Thr Gln Asp Cys Ser Phe Gln His Ser Pro Ile Ser Ser Asp
        115                 120                 125

Phe Ala Val Lys Ile Arg Glu Leu Ser Asp Tyr Leu Leu Gln Asp Tyr
    130                 135                 140

Pro Val Thr Val Ala Ser Asn Leu Gln
145                 150
```

(2) INFORMATION FOR SEQ ID NO:29:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Ala Asp Glu Glu Leu Cys Gly Gly Leu Trp Arg Leu Val Leu Ala Gln
  1               5                  10                  15

Arg Trp Met Glu Arg Leu Lys Thr Val Ala Gly Ser Lys Met Gln Gly
             20                  25                  30

Leu Leu Glu Arg Val Asn Thr Glu Ile His Phe Val Thr Lys Cys Ala
         35                  40                  45

Phe Gln Pro Pro Pro Ser Cys Leu Arg Phe Val Gln Thr Asn Ile Ser
     50                  55                  60

Arg Leu Leu Gln Glu Thr Ser Glu Gln Leu Val Ala Leu Lys Pro Trp
 65                  70                  75                  80

Ile Thr Arg Gln Asn Phe Ser Arg Cys Leu Glu Leu Gln Cys Gln Pro
                 85                  90                  95

Asp Ser Ser Thr Leu Gly Gly Gly Ser Gly Gly Gly Ser Gly Gly Gly
            100                 105                 110

Ser Gly Gly Gly Thr Gln Asp Cys Ser Phe Gln His Ser Pro Ile Ser
        115                 120                 125
```

Ser Asp Phe Ala Val Lys Ile Arg Glu Leu Ser Asp Tyr Leu Leu Gln
130                 135                 140

Asp Tyr Pro Val Thr Val Ala Ser Asn Leu Gln
145                 150                 155

(2) INFORMATION FOR SEQ ID NO:30:

(i) SEQUENCE CHARACTERISTICS:
      (A) LENGTH: 161 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:30:

Ala Asp Glu Glu Leu Cys Gly Gly Leu Trp Arg Leu Val Leu Ala Gln
1               5                   10                  15

Arg Trp Met Glu Arg Leu Lys Thr Val Ala Gly Ser Lys Met Gln Gly
                20                  25                  30

Leu Leu Glu Arg Val Asn Thr Glu Ile His Phe Val Thr Lys Cys Ala
            35                  40                  45

Phe Gln Pro Pro Pro Ser Cys Leu Arg Phe Val Gln Thr Asn Ile Ser
50                  55                  60

Arg Leu Leu Gln Glu Thr Ser Glu Gln Leu Val Ala Leu Lys Pro Trp
65                  70                  75                  80

Ile Thr Arg Gln Asn Phe Ser Arg Cys Leu Glu Leu Gln Cys Gln Pro
                85                  90                  95

Asp Ser Ser Thr Leu Gly Gly Gly Ser Gly Gly Gly Ser Gly Gly Gly
            100                 105                 110

Ser Gly Gly Gly Ser Gly Gly Gly Ser Gly Thr Gln Asp Cys Ser Phe
        115                 120                 125

Gln His Ser Pro Ile Ser Ser Asp Phe Ala Val Lys Ile Arg Glu Leu
    130                 135                 140

Ser Asp Tyr Leu Leu Gln Asp Tyr Pro Val Thr Val Ala Ser Asn Leu
145                 150                 155                 160

Gln (2) INFORMATION FOR SEQ ID NO:31:

(i) SEQUENCE CHARACTERISTICS:
      (A) LENGTH: 155 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:31:

Ala Asp Tyr Pro Val Thr Val Ala Ser Asn Leu Gln Asp Glu Glu Leu
1               5                   10                  15

Cys Gly Gly Leu Trp Arg Leu Val Leu Ala Gln Arg Trp Met Glu Arg
                20                  25                  30

Leu Lys Thr Val Ala Gly Ser Lys Met Gln Gly Leu Leu Glu Arg Val
            35                  40                  45

Asn Thr Glu Ile His Phe Val Thr Lys Cys Ala Phe Gln Pro Pro Pro
50                  55                  60

Ser Cys Leu Arg Phe Val Gln Thr Asn Ile Ser Arg Leu Leu Gln Glu
65                  70                  75                  80

```
Thr Ser Glu Gln Leu Val Ala Leu Lys Pro Trp Ile Thr Arg Gln Asn
            85                  90                  95

Phe Ser Arg Cys Leu Glu Leu Gln Cys Gln Pro Asp Ser Ser Thr Leu
            100                 105                 110

Gly Gly Gly Ser Gly Gly Gly Ser Gly Gly Ser Gly Gly Gly Thr
            115                 120                 125

Gln Asp Cys Ser Phe Gln His Ser Pro Ile Ser Ser Asp Phe Ala Val
            130                 135                 140

Lys Ile Arg Glu Leu Ser Asp Tyr Leu Leu Gln
145                 150                 155

(2) INFORMATION FOR SEQ ID NO:32:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

Ala Ala Ser Asn Leu Gln Asp Glu Glu Leu Cys Gly Gly Leu Trp Arg
1               5                   10                  15

Leu Val Leu Ala Gln Arg Trp Met Glu Arg Leu Lys Thr Val Ala Gly
            20                  25                  30

Ser Lys Met Gln Gly Leu Leu Glu Arg Val Asn Thr Glu Ile His Phe
            35                  40                  45

Val Thr Lys Cys Ala Phe Gln Pro Pro Pro Ser Cys Leu Arg Phe Val
            50                  55                  60

Gln Thr Asn Ile Ser Arg Leu Leu Gln Glu Thr Ser Glu Gln Leu Val
65                  70                  75                  80

Ala Leu Lys Pro Trp Ile Thr Arg Gln Asn Phe Ser Arg Cys Leu Glu
            85                  90                  95

Leu Gln Cys Gln Pro Asp Ser Ser Thr Leu Gly Gly Gly Ser Gly Gly
            100                 105                 110

Gly Ser Gly Gly Ser Gly Gly Gly Thr Gln Asp Cys Ser Phe Gln
            115                 120                 125

His Ser Pro Ile Ser Ser Asp Phe Ala Val Lys Ile Arg Glu Leu Ser
            130                 135                 140

Asp Tyr Leu Leu Gln Asp Tyr Pro Val Thr Val
145                 150                 155

(2) INFORMATION FOR SEQ ID NO:33:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Ala Val Ala Gly Ser Lys Met Gln Gly Leu Leu Glu Arg Val Asn Thr
1               5                   10                  15

Glu Ile His Phe Val Thr Lys Cys Ala Phe Gln Pro Pro Pro Ser Cys
            20                  25                  30

Leu Arg Phe Val Gln Thr Asn Ile Ser Arg Leu Leu Gln Glu Thr Ser
            35                  40                  45
```

Glu Gln Leu Val Ala Leu Lys Pro Trp Ile Thr Arg Gln Asn Phe Ser
    50                  55                  60

Arg Cys Leu Glu Leu Gln Cys Gln Pro Asp Ser Ser Thr Leu Gly Gly
65                  70                  75                  80

Gly Ser Gly Gly Gly Ser Gly Gly Ser Gly Gly Gly Thr Gln Asp
                85                  90                  95

Cys Ser Phe Gln His Ser Pro Ile Ser Ser Asp Phe Ala Val Lys Ile
                100                 105                 110

Arg Glu Leu Ser Asp Tyr Leu Leu Gln Asp Tyr Pro Val Thr Val Ala
            115                 120                 125

Ser Asn Leu Gln Asp Glu Glu Leu Cys Gly Gly Leu Trp Arg Leu Val
    130                 135                 140

Leu Ala Gln Arg Trp Met Glu Arg Leu Lys Thr
145                 150                 155

(2) INFORMATION FOR SEQ ID NO:34:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

Ala Ser Lys Met Gln Gly Leu Leu Glu Arg Val Asn Thr Glu Ile His
1                   5                   10                  15

Phe Val Thr Lys Cys Ala Phe Gln Pro Pro Ser Cys Leu Arg Phe
                20                  25                  30

Val Gln Thr Asn Ile Ser Arg Leu Leu Gln Glu Thr Ser Glu Gln Leu
            35                  40                  45

Val Ala Leu Lys Pro Trp Ile Thr Arg Gln Asn Phe Ser Arg Cys Leu
    50                  55                  60

Glu Leu Gln Cys Gln Pro Asp Ser Ser Thr Leu Gly Gly Gly Ser Gly
65                  70                  75                  80

Gly Gly Ser Gly Gly Gly Ser Gly Gly Gly Thr Gln Asp Cys Ser Phe
                85                  90                  95

Gln His Ser Pro Ile Ser Ser Asp Phe Ala Val Lys Ile Arg Glu Leu
                100                 105                 110

Ser Asp Tyr Leu Leu Gln Asp Tyr Pro Val Thr Val Ala Ser Asn Leu
            115                 120                 125

Gln Asp Glu Glu Leu Cys Gly Gly Leu Trp Arg Leu Val Leu Ala Gln
    130                 135                 140

Arg Trp Met Glu Arg Leu Lys Thr Val Ala Gly
145                 150                 155

(2) INFORMATION FOR SEQ ID NO:35:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

Ala Pro Pro Ser Cys Leu Arg Phe Val Gln Thr Asn Ile Ser Arg Leu

```
            1               5                    10                      15
Leu  Gln  Glu  Thr  Ser  Glu  Gln  Leu  Val  Ala  Leu  Lys  Pro  Trp  Ile  Thr
                    20                    25                   30

Arg  Gln  Asn  Phe  Ser  Arg  Cys  Leu  Glu  Leu  Gln  Cys  Gln  Pro  Asp  Ser
               35                    40                    45

Ser  Thr  Leu  Gly  Gly  Gly  Ser  Gly  Gly  Ser  Gly  Gly  Gly  Ser  Gly
     50                    55                    60

Gly  Gly  Thr  Gln  Asp  Cys  Ser  Phe  Gln  His  Ser  Pro  Ile  Ser  Ser  Asp
65                   70                    75                             80

Phe  Ala  Val  Lys  Ile  Arg  Glu  Leu  Ser  Asp  Tyr  Leu  Leu  Gln  Asp  Tyr
                    85                    90                        95

Pro  Val  Thr  Val  Ala  Ser  Asn  Leu  Gln  Asp  Glu  Glu  Leu  Cys  Gly  Gly
               100                   105                   110

Leu  Trp  Arg  Leu  Val  Leu  Ala  Gln  Arg  Trp  Met  Glu  Arg  Leu  Lys  Thr
               115                   120                   125

Val  Ala  Gly  Ser  Lys  Met  Gln  Gly  Leu  Leu  Glu  Arg  Val  Asn  Thr  Glu
     130                   135                   140

Ile  His  Phe  Val  Thr  Lys  Cys  Ala  Phe  Gln  Pro
145                  150                   155
```

(2) INFORMATION FOR SEQ ID NO:36:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

```
Ala  Arg  Phe  Val  Gln  Thr  Asn  Ile  Ser  Arg  Leu  Leu  Gln  Glu  Thr  Ser
1                    5                    10                        15

Glu  Gln  Leu  Val  Ala  Leu  Lys  Pro  Trp  Ile  Thr  Arg  Gln  Asn  Phe  Ser
                    20                    25                   30

Arg  Cys  Leu  Glu  Leu  Gln  Cys  Gln  Pro  Asp  Ser  Ser  Thr  Leu  Gly  Gly
               35                    40                    45

Gly  Ser  Gly  Gly  Gly  Ser  Gly  Gly  Ser  Gly  Gly  Thr  Gln  Asp
     50                    55                    60

Cys  Ser  Phe  Gln  His  Ser  Pro  Ile  Ser  Ser  Asp  Phe  Ala  Val  Lys  Ile
65                   70                    75                             80

Arg  Glu  Leu  Ser  Asp  Tyr  Leu  Leu  Gln  Asp  Tyr  Pro  Val  Thr  Val  Ala
                    85                    90                        95

Ser  Asn  Leu  Gln  Asp  Glu  Glu  Leu  Cys  Gly  Gly  Leu  Trp  Arg  Leu  Val
               100                   105                   110

Leu  Ala  Gln  Arg  Trp  Met  Glu  Arg  Leu  Lys  Thr  Val  Ala  Gly  Ser  Lys
               115                   120                   125

Met  Gln  Gly  Leu  Leu  Glu  Arg  Val  Asn  Thr  Glu  Ile  His  Phe  Val  Thr
     130                   135                   140

Lys  Cys  Ala  Phe  Gln  Pro  Pro  Ser  Cys  Leu
145                  150                   155
```

(2) INFORMATION FOR SEQ ID NO:37:

(i) SEQUENCE CHARACTERISTICS:
        (A) LENGTH: 155 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:37:

| Ala | Thr | Asn | Ile | Ser | Arg | Leu | Leu | Gln | Glu | Thr | Ser | Glu | Gln | Leu | Val |
|---|---|---|---|---|---|---|---|---|---|---|---|---|---|---|---|
| 1 | | | | 5 | | | | | 10 | | | | | 15 | |

| Ala | Leu | Lys | Pro | Trp | Ile | Thr | Arg | Gln | Asn | Phe | Ser | Arg | Cys | Leu | Glu |
|---|---|---|---|---|---|---|---|---|---|---|---|---|---|---|---|
| | | | 20 | | | | | 25 | | | | | 30 | | |

| Leu | Gln | Cys | Gln | Pro | Asp | Ser | Ser | Thr | Leu | Gly | Gly | Gly | Ser | Gly | Gly |
|---|---|---|---|---|---|---|---|---|---|---|---|---|---|---|---|
| | | 35 | | | | | 40 | | | | | 45 | | | |

| Gly | Ser | Gly | Gly | Gly | Ser | Gly | Gly | Thr | Gln | Asp | Cys | Ser | Phe | Gln |
|---|---|---|---|---|---|---|---|---|---|---|---|---|---|---|
| | 50 | | | | 55 | | | | 60 | | | | | |

| His | Ser | Pro | Ile | Ser | Ser | Asp | Phe | Ala | Val | Lys | Ile | Arg | Glu | Leu | Ser |
|---|---|---|---|---|---|---|---|---|---|---|---|---|---|---|---|
| 65 | | | | | 70 | | | | | 75 | | | | | 80 |

| Asp | Tyr | Leu | Leu | Gln | Asp | Tyr | Pro | Val | Thr | Val | Ala | Ser | Asn | Leu | Gln |
|---|---|---|---|---|---|---|---|---|---|---|---|---|---|---|---|
| | | | | 85 | | | | | 90 | | | | | 95 | |

| Asp | Glu | Glu | Leu | Cys | Gly | Gly | Leu | Trp | Arg | Leu | Val | Leu | Ala | Gln | Arg |
|---|---|---|---|---|---|---|---|---|---|---|---|---|---|---|---|
| | | | 100 | | | | | 105 | | | | 110 | | | |

| Trp | Met | Glu | Arg | Leu | Lys | Thr | Val | Ala | Gly | Ser | Lys | Met | Gln | Gly | Leu |
|---|---|---|---|---|---|---|---|---|---|---|---|---|---|---|---|
| | | 115 | | | | | 120 | | | | | 125 | | | |

| Leu | Glu | Arg | Val | Asn | Thr | Glu | Ile | His | Phe | Val | Thr | Lys | Cys | Ala | Phe |
|---|---|---|---|---|---|---|---|---|---|---|---|---|---|---|---|
| | 130 | | | | | 135 | | | | | 140 | | | | |

| Gln | Pro | Pro | Pro | Ser | Cys | Leu | Arg | Phe | Val | Gln |
|---|---|---|---|---|---|---|---|---|---|---|
| 145 | | | | | 150 | | | | | 155 |

(2) INFORMATION FOR SEQ ID NO:38:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:38:

Gly Gly Gly Ser
1

(2) INFORMATION FOR SEQ ID NO:39:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:39:

Gly Gly Gly Ser Gly Gly Gly Ser
1            5

(2) INFORMATION FOR SEQ ID NO:40:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:40:

Gly Gly Gly Ser Gly Gly Gly Ser Gly Gly Gly Ser
1               5                   10

(2) INFORMATION FOR SEQ ID NO:41:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

Ser Gly Gly Ser Gly Gly Ser
1               5

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

Glu Phe Gly Asn Met
1               5

(2) INFORMATION FOR SEQ ID NO:43:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

Glu Phe Gly Gly Asn Met
1               5

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

Glu Phe Gly Gly Asn Gly Gly Asn Met
1               5

(2) INFORMATION FOR SEQ ID NO:45:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:45:

Gly Gly Ser Asp Met Ala Gly
1               5

(2) INFORMATION FOR SEQ ID NO:46:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:46:

Ser Gly Gly Asn Gly
1               5

(2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:47:

Ser Gly Gly Asn Gly Ser Gly Gly Asn Gly
1               5                   10

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:48:

Ser Gly Gly Asn Gly Ser Gly Gly Asn Gly Ser Gly Gly Asn Gly
1               5                   10                  15

(2) INFORMATION FOR SEQ ID NO:49:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

Ser Gly Gly Ser Gly Ser Gly Gly Ser Gly
1               5                   10

(2) INFORMATION FOR SEQ ID NO:50:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:50:

```
Ser Gly Gly Ser Gly Ser Gly Gly Ser Gly Ser Gly Gly Ser Gly
1               5                   10                  15
```

(2) INFORMATION FOR SEQ ID NO:51:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:51:

```
Gly Gly Gly Ser Gly Gly
1               5
```

(2) INFORMATION FOR SEQ ID NO:52:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:52:

```
Gly Gly Gly Ser Gly Gly Gly
1               5
```

(2) INFORMATION FOR SEQ ID NO:53:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

```
Gly Gly Gly Ser Gly Gly Gly Ser Gly Gly
1               5                   10
```

(2) INFORMATION FOR SEQ ID NO:54:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:54:

```
Gly Gly Gly Ser Gly Gly Gly Ser Gly Gly Gly Ser Gly
1               5                   10
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:55:

Gly Gly Gly Ser Gly Gly Gly Ser Gly Gly Gly Ser Gly Gly Gly
 1               5                  10                  15

(2) INFORMATION FOR SEQ ID NO:56:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:56:

Gly Gly Gly Ser Gly Gly Gly Ser Gly Gly Gly Ser Gly Gly Gly Ser
 1               5                  10                  15

Gly Gly Gly Ser Gly
            20

(2) INFORMATION FOR SEQ ID NO:57:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:57:

CTGACCATGG CNACCCAGGA CTGCTCCTTC CAA                          33

(2) INFORMATION FOR SEQ ID NO:58:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:58:

ACTGAAGCTT AGGGCTGACA CTGCAGCTCC AG                           32

(2) INFORMATION FOR SEQ ID NO:59:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:59:

ACTGAAGCTT ACAGGGTTGA GGAGTCGGGC TG                           32

(2) INFORMATION FOR SEQ ID NO:60:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:60:

GACTGCCATG GCNACYCAGG AYTGYTCYTT YCAACACAGC CCCATC            46

(2) INFORMATION FOR SEQ ID NO:61:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:61:

GACTGCCATG GCNACYCAGG AYTGYTCYTT YCAACACAGC CCCATC                46

(2) INFORMATION FOR SEQ ID NO:62:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:62:

TGTCCAAACT CATCAATGTA TC                                          22

(2) INFORMATION FOR SEQ ID NO:63:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:63:

CATGGCCATG GCCGACGAGG AGCTCTGCGG GGGCCTCT                         38

(2) INFORMATION FOR SEQ ID NO:64:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:64:

GCTAGAAGCT TACTGCAGGT TGGAGGCCAC GGTGAC                           36

(2) INFORMATION FOR SEQ ID NO:65:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:65:

CATGGCCATG GCCTCCAAGA TGCAAGGCTT GCTGGAGC                         38

(2) INFORMATION FOR SEQ ID NO:66:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:66:

GCTAGAAGCT TACCCAGCGA CAGTCTTGAG CCGCTC                           36

(2) INFORMATION FOR SEQ ID NO:67:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:67:

CATGGCCATG GCCCCCCCCA GCTGTCTTCG CTTCGT       36

(2) INFORMATION FOR SEQ ID NO:68:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:68:

GCTAGAAGCT TAGGGCTGAA AGGCACATTT GGTGACA       37

(2) INFORMATION FOR SEQ ID NO:69:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:69:

CCCTGTCTGG CGGCAACGGC ACCCAGGACT GCTCCTTCCA AC       42

(2) INFORMATION FOR SEQ ID NO:70:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:70:

GCGGTAACGG CAGTGGAGGT AATGGCACCC AGGACTGCTC CTTCCAAC       48

(2) INFORMATION FOR SEQ ID NO:71:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:71:

ACGGCAGTGG TGGCAATGGG AGCGGCGGAA ATGGAACCCA GGACTGCTCC TTCCAAC       57

(2) INFORMATION FOR SEQ ID NO:72:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:72:

GTGCCGTTGC CGCCAGACAG GGTTGAGGAG TCGGGCTG       38

(2) INFORMATION FOR SEQ ID NO:73:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:73:

ATTACCTCCA CTGCCGTTAC CGCCTGACAG GGTTGAGGAG TCGGGCTG                    48

(2) INFORMATION FOR SEQ ID NO:74:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:74:

GCTCCCATTG CCACCACTGC CGTTACCTCC AGACAGGGTT GAGGAGTCGG GCTG             54

(2) INFORMATION FOR SEQ ID NO:75:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:75:

GATGAGGATC CGGTGGCAAT GGGAGCGGCG GAAATGGAAC CCAGGACTGC TCCTTCCACC       60

(2) INFORMATION FOR SEQ ID NO:76:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:76:

GATGACGGAT CCGTTACCTC CAGACAGGGT TGAGGAGTCG GGCTG                       45

(2) INFORMATION FOR SEQ ID NO:77:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:77:

GATGACGGAT CCGGAGGTAA TGGCACCCAG GACTGCTCCT TCCAAC                      46

(2) INFORMATION FOR SEQ ID NO:78:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:78:

GACTGCCATG GCCGACGAGG AGCTCTGCG                                         29

(2) INFORMATION FOR SEQ ID NO:79:

```
    (i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:79:

GACTCAAGCT TACTGCAGGT TGGAGGCC                                              28

(2) INFORMATION FOR SEQ ID NO:80:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:80:

GACTCGGGAT CCGGAGGTTC TGGCACCCAG GACTGCTCC                                  39

(2) INFORMATION FOR SEQ ID NO:81:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:81:

GACTGGGATC CGGTGGCAGT GGGAGCGGCG GATCTGGAAC C                               41

(2) INFORMATION FOR SEQ ID NO:82:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:82:

GACTTGGGAT CCACTACCTC CAGACAGGGT TGAGGAGTC                                  39

(2) INFORMATION FOR SEQ ID NO:83:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:83:

ACTGACGGAT CCACCGCCCA GGGTTGAGGA GTCGGGCTG                                  39

(2) INFORMATION FOR SEQ ID NO:84:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:84:

ACTGACGGAT CCACCTCCTG ACCCACCGCC CAGGGTTGAG GAGTCGGGCT G                    51

(2) INFORMATION FOR SEQ ID NO:85:

(i) SEQUENCE CHARACTERISTICS:
```

```
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:85:

ACTGACGGAT CCACCTCCTG ACCCACCTCC TGACCCACCG CCCAGGGTTG AGGAGTCGGG      60

CTG                                                                   63

(2) INFORMATION FOR SEQ ID NO:86:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:86:

ACGTAAAGCT TACAGGGTTG AGGAGTCG                                        28

(2) INFORMATION FOR SEQ ID NO:87:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:87:

GTCAGTGGAT CCGGAGGTAC CCAGGACTGC TCCTTCCAAC                            40

(2) INFORMATION FOR SEQ ID NO:88:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:88:

GTCAGTGGAT CCGGAGGTGG CACCCAGGAC TGCTCCTTCC AAC                        43

(2) INFORMATION FOR SEQ ID NO:89:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:89:

GTCAGTGGAT CCGGAGGTGG CTCAGGGGGA GGTAGTGGTA CCCAGGACTG CTCCTTCCAC      60

(2) INFORMATION FOR SEQ ID NO:90:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:90:

GTTGCCATGG CNTCNAAYCT GCARGAYGAR GARCTGTGCG GGGGCCTCTG GCGGCTG         57

(2) INFORMATION FOR SEQ ID NO:91:
```

(i) SEQUENCE CHARACTERISTICS:
    (A) LENGTH: 57 base pairs
    (B) TYPE: nucleic acid
    (C) STRANDEDNESS: single
    (D) TOPOLOGY: linear (xi) SEQUENCE DESCRIPTION: SEQ ID NO:91:

GTTGCCATGG CNAAYCTGCA RGAYGARGAR CTGTGYGGGG GCCTCTGGCG GCTGGTC    57

(2) INFORMATION FOR SEQ ID NO:92:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:92:

GTTGCCATGG CNCTGCARGA YGARGARCTG TGYGGYGGCC TCTGGCGGCT GGTCCTG    57

(2) INFORMATION FOR SEQ ID NO:93:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:93:

GTTGCCATGG CNCARGAYGA RGARCTGTGY GGYGGYCTCT GGCGGCTGGT CCTGGCA    57

(2) INFORMATION FOR SEQ ID NO:94:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:94:

GTTGCCATGG CNGAYGARGA RCTGTGYGGY GGYCTCTGGC GGCTGGTCCT GGCACAG    57

(2) INFORMATION FOR SEQ ID NO:95:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:95:

GTTGCCATGG CNGARGARCT GTGYGGYGGY CTCTGGCGGC TGGTCCTGGC ACAGCGC    57

(2) INFORMATION FOR SEQ ID NO:96:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:96:

GTTGCCATGG CNGARCTGTG YGGYGGYCTG TGGCGYCTGG TCCTGGCACA GCGCTGG    57

(2) INFORMATION FOR SEQ ID NO:97:

(i) SEQUENCE CHARACTERISTICS:

(A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:97:

GTTGCCATGG CNCTGTGYGG YGGYCTGTGG CGYCTGGTCC TGGCACAGCG CTGGATG        57

(2) INFORMATION FOR SEQ ID NO:98:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:98:

TATGCAAGCT TAGGCCACGG TGACTGGGTA        30

(2) INFORMATION FOR SEQ ID NO:99:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:99:

TATGCAAGCT TAGGAGGCCA CGGTGACTGG        30

(2) INFORMATION FOR SEQ ID NO:100:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:100:

TATGCAAGCT TAGTTGGAGG CCACGGTGAC        30

(2) INFORMATION FOR SEQ ID NO:101:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:101:

TATGCAAGCT TACAGGTTGG AGGCCACGGT        30

(2) INFORMATION FOR SEQ ID NO:102:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:102:

TATGCAAGCT TACTGCAGGT TGGAGGCCAC        30

(2) INFORMATION FOR SEQ ID NO:103:

(i) SEQUENCE CHARACTERISTICS:
        (A) LENGTH: 30 base pairs (B) TYPE: nucleic acid
            (C) STRANDEDNESS: single
            (D) TOPOLOGY: linear (xi) SEQUENCE DESCRIPTION: SEQ ID NO:103:

TATGCAAGCT TAGTCCTGCA GGTTGGAGGC                                             30

(2) INFORMATION FOR SEQ ID NO:104:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:104:

TATGCAAGCT TACTCGTCCT GCAGGTTGGA                                             30

(2) INFORMATION FOR SEQ ID NO:105:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:105:

TATGCAAGCT TACTCCTCGT CCTGCAGGTT                                             30

(2) INFORMATION FOR SEQ ID NO:106:

(i) SEQUENCE CHARACTERISTICS:
            (A) LENGTH: 405 base pairs
            (B) TYPE: nucleic acid
            (C) STRANDEDNESS: single
            (D) TOPOLOGY: linear (xi) SEQUENCE DESCRIPTION: SEQ ID NO:106:

GCCACCCAGG ACTGCTCCTT CCAACACAGC CCCATCTCCT CCGACTTCGC TGTCAAAATC            60

CGTGAGCTGT CTGACTACCT GCTTCAAGAT TACCCAGTCA CCGTGGCCTC CAACCTGCAG           120

GACGAGGAGC TCTGCGGGGC GCTCTGGCGG CTGGTCCTGG CACAGCGCTG GATGGAGCGG           180

CTCAAGACTG TCGCTGGGTC CAAGATGCAA GGCTTGCTGG AGCGCGTGAA CACGGAGATA          240

CACTTTGTCA CCAAATGTGC CTTTCAGCCC CCCCCCAGCT GTCTTCGCTT CGTCCAGACC          300

AACATCTCCC GCCTCCTGCA GGAGACCTCC GAGCAGCTGG TGGCGCTGAA GCCCTGGATC          360

ACTCGCCAGA ACTTCTCCCG GTGCCTGGAG CTGCAGTGTC AGCCC                          405

(2) INFORMATION FOR SEQ ID NO:107:

(i) SEQUENCE CHARACTERISTICS:
            (A) LENGTH: 420 base pairs
            (B) TYPE: nucleic acid
            (C) STRANDEDNESS: single
            (D) TOPOLOGY: linear (xi) SEQUENCE DESCRIPTION: SEQ ID NO:107:

GCCACCCAGG ACTGCTCCTT CCAACACAGC CCCATCTCCT CCGACTTCGC TGTCAAAATC            60

CGTGAGCTGT CTGACTACCT GCTTCAAGAT TACCCAGTCA CCGTGGCCTC CAACCTGCAG           120

GACGAGGAGC TCTGCGGGGG CCTCTGGCGG CTGGTCCTGG CACAGCGCTG GATGGAGCGG          180

CTCAAGACTG TCGCTGGGTC CAAGATGCAA GGCTTGCTGG AGCGCGTGAA CACGGAGATA          240

CACTTTGTCA CCAAATGTGC CTTTCAGCCC CCCCCCAGCT GTCTTCGCTT CGTCCAGACC          300

```
AACATCTCCC GCCTCCTGCA GGAGACCTCC GAGCAGCTGG TGGCGCTGAA GCCCTGGATC      360

ACTCGCCAGA ACTTCTCCCG GTGCCTGGAG CTGCAGTGTC AGCCCGACTC CTCAACCCTG      420

(2) INFORMATION FOR SEQ ID NO:108:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (xi) SEQUENCE DESCRIPTION: SEQ ID NO:108:

GCCACCCAGG ACTGCTCCTT CCAACACAGC CCCATCTCCT CCGACTTCGC TGTCAAAATC       60

CGTGAGCTGT CTGACTACCT GCTTCAAGAT TACCCAGTCA CCGTGGCCTC CAACCTGCAG      120

GACGAGGAGC TCTGCGGGGG CCTCTGGCGG CTGGTCCTGG CACAGCGCTG GATGGAGCGG      180

CTCAAGACTG TCGCTGGGTC CAAGATGCAA GGCTTGCTGG AGCGCGTGAA CACGGAGATA      240

CACTTTGTCA CCAAATGTGC CTTTCAGGAG ACCTCCGAGC AGCTGGTGGC GCTGAAGCCC      300

TGGATCACTC GCCAGAACTT CTCCCGGTGC CTGGAGCTGC AGTGTCAGCC CGACTCCTCA      360

ACCCTG                                                                 366

(2) INFORMATION FOR SEQ ID NO:109:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (xi) SEQUENCE DESCRIPTION: SEQ ID NO:109:

GGAACTCAGG ATTGTTCTTT CCAACACAGC CCCATCTCCT CCGACTTCGC TGTCAAAATC       60

CGTGAGCTGT CTGACTACCT GCTTCAAGAT TACCCAGTCA CCGTGGCCTC CAACCTGCAG      120

GACGAGGAGC TCTGCGGGGG CCTCTGGCGG CTGGTCCTGG CACAGCGCTG GATGGAGCGG      180

CTCAAGACTG TCGCTGGGTC CAAGATGCAA GGCTTGCTGG AGCGCGTGAA CACGGAGATA      240

CACTTTGTCA CCAAATGTGC CTTTCAGCCC CCCCCCAGCT GTCTTCGCTT CGTCCAGACC      300

AACATCTCCC GCCTCCTGCA GGAGACCTCC GAGCAGCTGG TGGCGCTGAA GCCCTGGATC      360

ACTCGCCAGA ACTTCTCCCG GTGCCTGGAG CTGCAGTGTC AGCCC                      405

(2) INFORMATION FOR SEQ ID NO:110:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (xi) SEQUENCE DESCRIPTION: SEQ ID NO:110:

GGTACCCAGG ATTGTTCTTT CCAACACAGC CCCATCTCCT CCGACTTCGC TGTCAAAATC       60

CGTGAGCTGT CTGACTACCT GCTTCAAGAT TACCCAGTCA CCGTGGCCTC CAACCTGCAG      120

GACGAGGAGC TCTGCGGGGG CCTCTGGCGG CTGGTCCTGG CACAGCGCTG GATGGAGCGG      180

CTCAAGACTG TCGCTGGGTC CAAGATGCAA GGCTTGCTGG AGCGCGTGAA CACGGAGATA      240

CACTTTGTCA CCAAATGTGC CTTTCAGCCC CCCCCCAGCT GTCTTCGCTT CGTCCAGACC      300

AACATCTCCC GCCTCCTGCA GGAGACCTCC GAGCAGCTGG TGGCGCTGAA GCCCTGGATC      360

ACTCGCCAGA ACTTCTCCCG GTGCCTGGAG CTGCAGTGTC AGCCCGACTC CTCAACCCTG      420
```

(2) INFORMATION FOR SEQ ID NO:111:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (xi) SEQUENCE DESCRIPTION: SEQ ID NO:111:

```
GCCACTCAGG ACTGTTCTTT CCAACACAGC CCCATCTCCT CCGACTTCGC TGTCAAAATC      60
CGTGAGCTGT CTGACTACCT GCTTCAAGAT TACCCAGTCA CCGTGGCCTC CAACCTGCAG     120
GACGAGGAGC TCTGCGGGGG CCTCTGGCGG CTGGTCCTGG CACAGCGCTG GATGGAGCGG     180
CTCAAGACTG TCGCTGGGTC CAAGATGCAA GGCTTGCTGG AGCGCGTGAA CACGGAGATA     240
CACTTTGTCA CCAAATGTGC CTTTCAGCCC CCCCCCAGCT GTCTTCGCTT CGTCCAGACC     300
AACATCTCCC GCCTCCTGCA GGAGACCTCC GAGCAGCTGG TGGCGCTGAA GCCCTGGATC     360
ACTCGCCAGA ACTTCTCCCG GTGCCTGGAG CTGCAGTGTC AGCCC                     405
```

(2) INFORMATION FOR SEQ ID NO:112:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (xi) SEQUENCE DESCRIPTION: SEQ ID NO:112:

```
GCCACTCAGG ACTGCTCTTT TCAACACAGC CCCATCTCCT CCGACTTCGC TGTCAAAATC      60
CGTGAGCTGT CTGACTACCT GCTTCAAGAT TACCCAGTCA CCGTGGCCTC CAACCTGCAG     120
GACGAGGAGC TCTGCGGGGG CCTCTGGCGG CTGGTCCTGG CACAGCGCTG GATGGAGCGG     180
CTCAAGACTG TCGCTGGGTC CAAGATGCAA GGCTTGCTGG AGCGCGTGAA CACGGAGATA     240
CACTTTGTCA CCAAATGTGC CTTTCAGCCC CCCCCCAGCT GTCTTCGCTT CGTCCAGACC     300
AACATCTCCC GCCTCCTGCA GGAGACCTCC GAGCAGCTGG TGGCGCTGAA GCCCTGGATC     360
ACTCGCCAGA ACTTCTCCCG GTGCCTGGAG CTGCAGTGTC AGCCCGACTC CTCAACCCTG     420
```

(2) INFORMATION FOR SEQ ID NO:113:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:113:

```
GCCGACGAGG AGCTCTGCGG GGGCCTCTGG CGGCTGGTCC TGGCACAGCG CTGGATGGAG      60
CGGCTCAAGA CTGTCGCTGG GTCCAAGATG CAAGGCTTGC TGGAGCGCGT GAACACGGAG     120
ATACACTTTG TCACCAAATG TGCCTTTCAG CCCCCCCCCA GCTGTCTTCG CTTCGTCCAG     180
ACCAACATCT CCCGCCTCCT GCAGGAGACC TCCGAGCAGC TGGTGGCGCT GAAGCCCTGG     240
ATCACTCGCC AGAACTTCTC CCGGTGCCTG GAGCTGCAGT GTCAGCCCGA CTCCTCAACC     300
CTGTCTGGAG GTAACGGATC CGGTGGCAAT GGGAGCGGCG GAAATGGAAC CCAGGACTGC     360
TCCTTCCAAC ACAGCCCCAT CTCCTCCGAC TTCGCTGTCA AAATCCGTGA GCTGTCTGAC     420
TACCTGCTTC AAGATTACCC AGTCACCGTG GCCTCCAACC TGCAG                     465
```

(2) INFORMATION FOR SEQ ID NO:114:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (xi) SEQUENCE DESCRIPTION: SEQ ID NO:114:

```
GCCGACGAGG AGCTCTGCGG GGGCCTCTGG CGGCTGGTCC TGGCACAGCG CTGGATGGAG      60

CGGCTCAAGA CTGTCGCTGG GTCCAAGATG CAAGGCTTGC TGGAGCGCGT GAACACGGAG     120

ATACACTTTG TCACCAAATG TGCCTTTCAG CCCCCCCCCA GCTGTCTTCG CTTCGTCCAG     180

ACCAACATCT CCCGCCTCCT GCAGGAGACC TCCGAGCAGC TGGTGGCGCT GAAGCCCTGG     240

ATCACTCGCC AGAACTTCTC CCGGTGCCTG GAGCTGCAGT GTCAGCCCGA CTCCTCAACC     300

CTGTCAGGCG GTAACGGCAG TGGAGGTAAT GGCACCCAGG ACTGCTCCTT CCAACACAGC     360

CCCATCTCCT CCGACTTCGC TGTCAAAATC CGTGAGCTGT CTGACTACCT GCTTCAAGAT     420

TACCCAGTCA CCGTGGCCTC CAACCTGCAG                                     450
```

(2) INFORMATION FOR SEQ ID NO:115:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (xi) SEQUENCE DESCRIPTION: SEQ ID NO:115:

```
GCCGACGAGG AGCTCTGCGG GGGCCTCTGG CGGCTGGTCC TGGCACAGCG CTGGATGGAG      60

CGGCTCAAGA CTGTCGCTGG GTCCAAGATG CAAGGCTTGC TGGAGCGCGT GAACACGGAG     120

ATACACTTTG TCACCAAATG TGCCTTTCAG CCCCCCCCCA GCTGTCTTCG CTTCGTCCAG     180

ACCAACATCT CCCGCCTCCT GCAGGAGACC TCCGAGCAGC TGGTGGCGCT GAAGCCCTGG     240

ATCACTCGCC AGAACTTCTC CCGGTGCCTG GAGCTGCAGT GTCAGCCCGA CTCCTCAACC     300

CTGTCTGGCG GCAACGGCAC CCAGGACTGC TCCTTCCAAC ACAGCCCCAT CTCCTCCGAC     360

TTCGCTGTCA AAATCCGTGA GCTGTCTGAC TACCTGCTTC AAGATTACCC AGTCACCGTG     420

GCCTCCAACC TGCAG                                                     435
```

(2) INFORMATION FOR SEQ ID NO:116:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:116:

```
GCCTCCAAGA TGCAAGGCTT GCTGGAGCGC GTGAACACGG AGATACACTT TGTCACCAAA      60

TGTGCCTTTC AGCCCCCCCC CAGCTGTCTT CGCTTCGTCC AGACCAACAT CTCCCGCCTC     120

CTGCAGGAGA CCTCCGAGCA GCTGGTGGCG CTGAAGCCCT GGATCACTCG CCAGAACTTC     180

TCCCGGTGCC TGGAGCTGCA GTGTCAGCCC GACTCCTCAA CCCTGTCTGG AGGTAACGGA     240

TCCGGTGGCA ATGGGAGCGG CGGAAATGGA ACCCAGGACT GCTCCTTCCA ACACAGCCCC     300

ATCTCCTCCG ACTTCGCTGT CAAAATCCGT GAGCTGTCTG ACTACCTGCT TCAAGATTAC     360

CCAGTCACCG TGGCCTCCAA CCTGCAGGAC GAGGAGCTCT GCGGGGGCCT CTGGCGGCTG     420

GTCCTGGCAC AGCGCTGGAT GGAGCGGCTC AAGACTGTCG CTGGG                    465
```

(2) INFORMATION FOR SEQ ID NO:117:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (xi) SEQUENCE DESCRIPTION: SEQ ID NO:117:

```
GCCTCCAAGA TGCAAGGCTT GCTGGAGCGC GTGAACACGG AGATACACTT TGTCACCAAA      60

TGTGCCTTTC AGCCCCCCCC CAGCTGTCTT CGCTTCGTCC AGACCAACAT CTCCCGCCTC     120

CTGCAGGAGA CCTCCGAGCA GCTGGTGGCG CTGAAGCCCT GGATCACTCG CCAGAACTTC     180

TCCCGGTGCC TGGAGCTGCA GTGTCAGCCC GACTCCTCAA CCCTGTCTGG AGGTAACGGA     240

TCCGGAGGTA ATGGCACCCA GGACTGCTCC TTCCAACACA GCCCCATCTC CTCCGACTTC     300

GCTGTCAAAA TCCGTGAGCT GTCTGACTAC CTGCTTCAAG ATTACCCAGT CACCGTGGCC     360

TCCAACCTGC AGGACGAGGA GCTCTGCGGG GGCCTCTGGC GGCTGGTCCT GGCACAGCGC     420

TGGATGGAGC GGCTCAAGAC TGTCGCTGGG                                     450
```

(2) INFORMATION FOR SEQ ID NO:118:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (xi) SEQUENCE DESCRIPTION: SEQ ID NO:118:

```
GCCTCCAAGA TGCAAGGCTT GCTGGAGCGC GTGAACACGG AGATACACTT TGTCACCAAA      60

TGTGCCTTTC AGCCCCCCCC CAGCTGTCTT CGCTTCGTCC AGACCAACAT CTCCCGCCTC     120

CTGCAGGAGA CCTCCGAGCA GCTGGTGGCG CTGAAGCCCT GGATCACTCG CCAGAACTTC     180

TCCCGGTGCC TGGAGCTGCA GTGTCAGCCC GACTCCTCAA CCCTGTCTGG CGGCAACGGC     240

ACGCAGGACT GCTCCTTCCA ACACAGCCCC ATCTCCTCCG ACTTCGCTGT CAAAATCCGT     300

GAGCTGTCTG ACTACCTGCT TCAAGATTAC CCAGTCACCG TGGCCTCCAA CCTGCAGGAC     360

GAGGAGCTCT GCGGGGGCCT CTGGCGGCTG GTCCTGGCAC AGCGCTGGAT GGAGCGGCTC     420

AAGACTGTCG CTGGG                                                     435
```

(2) INFORMATION FOR SEQ ID NO:119:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:119:

```
GCCCCCCCCA GCTGTCTTCG CTTCGTCCAG ACCAACATCT CCCGCCTCCT GCAGGAGACC      60

TCCGAGCAGC TGGTGGCGCT GAAGCCCTGG ATCACTCGCC AGAACTTCTC CCGGTGCCTG     120

GAGCTGCAGT GTCAGCCCGA CTCCTCAACC CTGTCTGGAG GTAACGGCAG TGGTGGCAAT     180

GGGAGCGGTG GAAATGGAAC CCAGGACTGC TCCTTCCAAC ACAGCCCCAT CTCCTCCGAC     240

TTCGCTGTCA AAATCCGTGA GCTGTCTGAC TACCTGCTTC AAGATTACCC AGTCACCGTG     300

GCCTCCAACC TGCAGGACGA GGAGCTCTGC GGGGGCCTCT GGCGGCTGGT CCTGGCACAG     360

CGCTGGATGG AGCGGCTCAA GACTGTCGCT GGGTCCAAGA TGCAAGGCTT GCTGGAGCGC     420
```

GTGAACACGG AGATACACTT TGTCACCAAA TGTGCCTTTC AGCCC         465

(2) INFORMATION FOR SEQ ID NO:120:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (xi) SEQUENCE DESCRIPTION: SEQ ID NO:120:

GCCCCCCCCA GCTGTCTTCG CTTCGTCCAG ACCAACATCT CCCGCCTCCT GCAGGAGACC    60

TCCGAGCAGC TGGTGGCGCT GAAGCCCTGG ATCACTCGCC AGAACTTCTC CCGGTGCCTG   120

GAGCTGCAGT GTCAGCCCGA CTCCTCAACC CTGTCAGGCG GTAACGGCAG TGGAGGTAAT   180

GGCACCCAGG ACTGCTCCTT CCAACACAGC CCCATCTCCT CCGACTTCGC TGTCAAAATC   240

CGTGAGCTGT CTGACTACCT GCTTCAAGAT TACCCAGTCA CCGTGGCCTC CAACCTGCAG   300

GACGAGGAGC TCTGCGGGGG CCTCTGGCGG CTGGTCCTGG CACAGCGCTG GATGGAGCGG   360

CTCAAGACTG TCGCTGGGTC CAAGATGCAA GGCTTGCTGG AGCGCGTGAA CACGGAGATA   420

CACTTTGTCA CCAAATGTGC CTTTCAGCCC                                    450

(2) INFORMATION FOR SEQ ID NO:121:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (xi) SEQUENCE DESCRIPTION: SEQ ID NO:121:

GCCCCCCCCA GCTGTCTTCG CTTCGTCCAG ACCAACATCT CCCGCCTCCT GCAGGAGACC    60

TCCGAGCAGC TGGTGGCGCT GAAGCCCTGG ATCACTCGCC AGAACTTCTC CCGGTGCCTG   120

GAGCTGCAGT GTCAGCCCGA CTCCTCAACC CTGTCTGGCG GCAACGGCAC GCAGGACTGC   180

TCCTTCCAAC ACAGCCCCAT CTCCTCCGAC TTCGCTGTCA AAATCCGTGA GCTGTCTGAC   240

TACCTGCTTC AAGATTACCC AGTCACCGTG GCCTCCAACC TGCAGGACGA GGAGCTCTGC   300

GGGGGCCTCT GGCGGCTGGT CCTGGCACAG CGCTGGATGG AGCGGCTCAA GACTGTCGCT   360

GGGTCCAAGA TGCAAGGCTT GCTGGAGCGC GTGAACACGG AGATACACTT TGTCACCAAA   420

TGTGCCTTTC AGCCC                                                    435

(2) INFORMATION FOR SEQ ID NO:122:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (xi) SEQUENCE DESCRIPTION: SEQ ID NO:122:

GCCGACGAGG AGCTCTGCGG GGGCCTCTGG CGGCTGGTCC TGGCACAGCG CTGGATGGAG    60

CGGCTCAAGA CTGTCGCTGG GTCCAAGATG CAAGGCTTGC TGGAGCGCGT GAACACGGAG   120

ATACACTTTG TCACCAAATG TGCCTTTCAG CCCCCCCCCA GCTGTCTTCG CTTCGTCCAG   180

ACCAACATCT CCCGCCTCCT GCAGGAGACC TCCGAGCAGC TGGTGGCGCT GAAGCCCTGG   240

ATCACTCGCC AGAACTTCTC CCGGTGCCTG GAGCTGCAGT GTCAGCCCGA CTCCTCAACC   300

CTGTCTGGAG GTAGTGGATC CGGAGGTTCT GGCAACCCAG GACTGCTCCT TCCAACACAG   360

```
CCCCATCTCC TCCGACTTCG CTGTCAAAAT CCGTGAGCTG TCTGACTACC TGCTTCAAGA        420

TTACCCAGTC ACCGTGGCCT CCAACCTGCA G                                       451

(2) INFORMATION FOR SEQ ID NO:123:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:123:

GCCGACGAGG AGCTCTGCGG GGGCCTCTGG CGGCTGGTCC TGGCACAGCG CTGGATGGAG         60

CGGCTCAAGA CTGTCGCTGG GTCCAAGATG CAAGGCTTGC TGGAGCGCGT GAACACGGAG        120

ATACACTTTG TCACCAAATG TGCCTTTCAG CCCCCCCCCA GCTGTCTTCG CTTCGTCCAG        180

ACCAACATCT CCCGCCTCCT GCAGGAGACC TCCGAGCAGC TGGTGGCGCT GAAGCCCTGG        240

ATCACTCGCC AGAACTTCTC CCGGTGCCTG GAGCTGCAGT GTCAGCCCGA CTCCTCAACC        300

CTGTCTGGAG GTAGTGGATC CGGTGGCAGT GGGAGCGGCG GATCTGGAAC CCAGGACTGC        360

TCCTTCCAAC ACAGCCCCAT CTCCTCCGAC TTCGCTGTCA AAATCCGTGA GCTGTCTGAC        420

TACCTGCTTC AAGATTACCC AGTCACCGTG GCCTCCAACC TGCAG                       465

(2) INFORMATION FOR SEQ ID NO:124:

(i) SEQUENCE CHARACTERISTICS:
        (A) LENGTH: 437 base pairs
        (B) TYPE: nucleic acid
        (C) STRANDEDNESS: single
        (D) TOPOLOGY: linear (xi) SEQUENCE DESCRIPTION: SEQ ID NO:124:

CCATGGCCAC CCAGGACTGC TCCTTCCAAC ACAGCCCCAT CTCCTCCGAC TTCGCTGTCA         60

AAATCCGTGA GCTGTCTGAC TACCTGCTTC AAGATTACCC AGTCACCGTG GCCTCCAACC        120

TGCAGGACGA GGAGCTCTGC GGGGGCCTCT GGCGGCTGGT CCTGGCACAG CGCTGGATGG        180

AGCGGCTCAA GACTGTCGCT GGGTCCAAGA TGCAAGGCTT GCTGGAGCGC GTGAACACGG        240

AGATACACTT TGTCACCAAA TGTGCCTTTC AGCCCCCCCC CAGCTGTCTT CGCTTCGTCC        300

AGACCAACAT CTCCCGCCTC CTGCAGGAGA CCTCCGAGCA GCTGGTGGCG CTGAAGCCCT        360

GGATCACTCG CCAGAACTTC TCCCGGTGCC TGGAGCTGCA GTGTCAGCCC GACTCCTCAA        420

CCCTGGGCGG TGGATCC                                                      437

(2) INFORMATION FOR SEQ ID NO:125:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (xi) SEQUENCE DESCRIPTION: SEQ ID NO:125:

GGATCCGGAG GTACCCAGGA CTGCTCCTTC AACACAGCC CCATCTCCTC CGACTTCGCT         60

GTCAAAATCC GTGAGCTGTC TGACTACCTG CTTCAAGATT ACCCAGTCAC CGTGGCCTCC        120

AACCTGCAGG ACGAGGAGCT CTGCGGGGGC CTCTGGCGGC TGGTCCTGGC ACAGCGCTGG        180

ATGGAGCGGC TCAAGACTGT CGCTGGGTCC AAGATGCAAG GCTTGCTGGA GCGCGTGAAC        240

ACGGAGATAC ACTTTGTCAC CAAATGTGCC TTTCAGCCCC CCCCAGCTG TCTTCGCTTC         300
```

```
GTCCAGACCA ACATCTCCCG CCTCCTGCAG GAGACCTCCG AGCAGCTGGT GGCGCTGAAG        360

CCCTGGATCA CTCGCCAGAA CTTCTCCCGG TGCCTGGAGC TGCAGTGTCA GCCCGACTCC        420

TCAACCCTGT AAGCTT                                                         436
```

(2) INFORMATION FOR SEQ ID NO:126:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO:126:

```
CCATGGCCAC CCAGGACTGC TCCTTCCAAC ACAGCCCCAT CTCCTCCGAC TTCGCTGTCA         60

AAATCCGTGA GCTGTCTGAC TACCTGCTTC AAGATTACCC AGTCACCGTG GCCTCCAACC        120

TGCAGGACGA GGAGCTCTGC GGGGGCCTCT GGCGGCTGGT CCTGGCACAG CGCTGGATGG        180

AGCGGCTCAA GACTGTCGCT GGGTCCAAGA TGCAAGGCTT GCTGGAGCGC GTGAACACGG        240

AGATACACTT TGTCACCAAA TGTGCCTTTC AGCCCCCCCC CAGCTGTCTT CGCTTCGTCC        300

AGACCAACAT CTCCCGCCTC CTGCAGGAGA CCTCCGAGCA GCTGGTGGCG CTGAAGCCCT        360

GGATCACTCG CCAGAACTTC TCCCGGTGCC TGGAGCTGCA GTGTCAGCCC GACTCCTCAA        420

CCCTGGGCGG TGGGTCAGGA GGTGGATCC                                           449
```

(2) INFORMATION FOR SEQ ID NO:127:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (xi) SEQUENCE DESCRIPTION: SEQ ID NO:127:

```
GGATCCGGAG GTGGCACCCA GGACTGCTCC TTCCAACACA GCCCCATCTC CTCCGACTTC         60

GCTGTCAAAA TCCGTGAGCT GTCTGACTAC CTGCTTCAAG ATTACCCAGT CACCGTGGCC        120

TCCAACCTGC AGGACGAGGA GCTCTGCGGG GGCCTCTGGC GGCTGGTCCT GGCACAGCGC        180

TGGATGGAGC GGCTCAAGAC TGTCGCTGGG TCCAAGATGC AAGGCTTGCT GGAGCGCGTG        240

AACACGGAGA TACACTTTGT CACCAAATGT GCCTTTCAGC CCCCCCCCAG CTGTCTTCGC        300

TTCGTCCAGA CCAACATCTC CCGCCTCCTG CAGGAGACCT CCGAGCAGCT GGTGGCGCTG        360

AAGCCCTGGA TCACTCGCCA GAACTTCTCC CGGTGCCTGG AGCTGCAGTG TCAGCCCGAC        420

TCCTCAACCC TGTAAGCTT                                                      439
```

(2) INFORMATION FOR SEQ ID NO:128:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (xi) SEQUENCE DESCRIPTION: SEQ ID NO:128:

```
CCATGGCCAC CCAGGACTGC TCCTTCCAAC ACAGCCCCAT CTCCTCCGAC TTCGCTGTCA         60

AAATCCGTGA GCTGTCTGAC TACCTGCTTC AAGATTACCC AGTCACCGTG GCCTCCAACC        120

TGCAGGACGA GGAGCTCTGC GGGGGCCTCT GGCGGCTGGT CCTGGCACAG CGCTGGATGG        180

AGCGGCTCAA GACTGTCGCT GGGTCCAAGA TGCAAGGCTT GCTGGAGCGC GTGAACACGG        240
```

```
AGATACACTT TGTCACCAAA TGTGCCTTTC AGCCCCCCCC CAGCTGTCTT CGCTTCGTCC      300

AGACCAACAT CTCCCGCCTC CTGCAGGAGA CCTCCGAGCA GCTGGTGGCG CTGAAGCCCT      360

GGATCACTCG CCAGAACTTC TCCCGGTGCC TGGAGCTGCA GTGTCAGCCC GACTCCTCAA      420

CCCTGGGCGG TGGGTCAGGA GGTGGGTCAG GAGGTGGATC C                         461

(2) INFORMATION FOR SEQ ID NO:129:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (xi) SEQUENCE DESCRIPTION: SEQ ID NO:129:

GGATCCGGAG GTGGCTCAGG GGGAGGTAGT GGTACCCAGG ACTGCTCCTT CCAACACAGC       60

CCCATCTCCT CCGACTTCGC TGTCAAAATC CGTGAGCTGT CTGACTACCT GCTTCAAGAT      120

TACCCAGTCA CCGTGGCCTC CAACCTGCAG GACGAGGAGC TCTGCGGGGG CCTCTGGCGG      180

CTGGTCCTGG CACAGCGCTG GATGGAGCGG CTCAAGACTG TCGCTGGGTC CAAGATGCAA      240

GGCTTGCTGG AGCGCGTGAA CACGGAGATA CACTTTGTCA CCAAATGTGC CTTTCAGCCC      300

CCCCCCAGCT GTCTTCGCTT CGTCCAGACC AACATCTCCC GCCTCCTGCA GGAGACCTCC      360

GAGCAGCTGG TGGCGCTGAA GCCCTGGATC ACTCGCCAGA ACTTCTCCCG GTGCCTGGAG      420

CTGCAGTGTC AGCCCGACTC CTCAACCCTG TAAGCTT                              457

(2) INFORMATION FOR SEQ ID NO:130:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (xi) SEQUENCE DESCRIPTION: SEQ ID NO:130:

GCCGACGAGG AGCTCTGCGG GGGCCTCTGG CGGCTGGTCC TGGCACAGCG CTGGATGGAG       60

CGGCTCAAGA CTGTCGCTGG GTCCAAGATG CAAGGCTTGC TGGAGCGCGT GAACACGGAG      120

ATACACTTTG TCACCAAATG TGCCTTTCAG CCCCCCCCCA GCTGTCTTCG CTTCGTCCAG      180

ACCAACATCT CCCGCCTCCT GCAGGAGACC TCCGAGCAGC TGGTGGCGCT GAAGCCCTGG      240

ATCACTCGCC AGAACTTCTC CCGGTGCCTG GAGCTGCAGT GTCAGCCCGA CTCCTCAACC      300

CTGGGCGGTG GATCCGGAGG TACCCAGGAC TGCTCCTTCC AACACAGCCC CATCTCCTCC      360

GACTTCGCTG TCAAAATCCG TGAGCTGTCT GACTACCTGC TTCAAGATTA CCCAGTCACC      420

GTGGCCTCCA ACCTGCAG                                                    438

(2) INFORMATION FOR SEQ ID NO:131:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (xi) SEQUENCE DESCRIPTION: SEQ ID NO:131:

GCCGACGAGG AGCTCTGCGG GGGCCTCTGG CGGCTGGTCC TGGCACAGCG CTGGATGGAG       60

CGGCTCAAGA CTGTCGCTGG GTCCAAGATG CAAGGCTTGC TGGAGCGCGT GAACACGGAG      120

ATACACTTTG TCACCAAATG TGCCTTTCAG CCCCCCCCCA GCTGTCTTCG CTTCGTCCAG      180
```

```
ACCAACATCT CCCGCCTCCT GCAGGAGACC TCCGAGCAGC TGGTGGCGCT GAAGCCCTGG        240

ATCACTCGCC AGAACTTCTC CCGGTGCCTG GAGCTGCAGT GTCAGCCCGA CTCCTCAACC        300

CTGGGCGGTG GATCCGGAGG TGGCACCCAG GACTGCTCCT TCCAACACAG CCCCATCTCC        360

TCCGACTTCG CTGTCAAAAT CCGTGAGCTG TCTGACTACC TGCTTCAAGA TTACCCAGTC        420

ACCGTGGCCT CCAACCTGCA G                                                  441

(2) INFORMATION FOR SEQ ID NO:132:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (xi) SEQUENCE DESCRIPTION: SEQ ID NO:132:

GCCGACGAGG AGCTCTGCGG GGGCCTCTGG CGGCTGGTCC TGGCACAGCG CTGGATGGAG         60

CGGCTCAAGA CTGTCGCTGG GTCCAAGATG CAAGGCTTGC TGGAGCGCGT GAACACGGAG        120

ATACACTTTG TCACCAAATG TGCCTTTCAG CCCCCCCCCA GCTGTCTTCG CTTCGTCCAG        180

ACCAACATCT CCCGCCTCCT GCAGGAGACC TCCGAGCAGC TGGTGGCGCT GAAGCCCTGG        240

ATCACTCGCC AGAACTTCTC CCGGTGCCTG GAGCTGCAGT GTCAGCCCGA CTCCTCAACC        300

CTGGGCGGTG GGTCAGGAGG TGGATCCGGA GGTACCCAGG ACTGCTCCTT CCAACACAGC        360

CCCATCTCCT CCGACTTCGC TGTCAAAATC CGTGAGCTGT CTGACTACCT GCTTCAAGAT        420

TACCCAGTCA CCGTGGCCTC CAACCTGCAG                                         450

(2) INFORMATION FOR SEQ ID NO:133:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (xi) SEQUENCE DESCRIPTION: SEQ ID NO:133:

GCCGACGAGG AGCTCTGCGG GGGCCTCTGG CGGCTGGTCC TGGCACAGCG CTGGATGGAG         60

CGGCTCAAGA CTGTCGCTGG GTCCAAGATG CAAGGCTTGC TGGAGCGCGT GAACACGGAG        120

ATACACTTTG TCACCAAATG TGCCTTTCAG CCCCCCCCCA GCTGTCTTCG CTTCGTCCAG        180

ACCAACATCT CCCGCCTCCT GCAGGAGACC TCCGAGCAGC TGGTGGCGCT GAAGCCCTGG        240

ATCACTCGCC AGAACTTCTC CCGGTGCCTG GAGCTGCAGT GTCAGCCCGA CTCCTCAACC        300

CTGGGCGGTG GATCCGGAGG TGGCTCAGGG GGAGGTAGTG GTACCCAGGA CTGCTCCTTC        360

CAACACAGCC CCATCTCCTC CGACTTCGCT GTCAAAATCC GTGAGCTGTC TGACTACCTG        420

CTTCAAGATT ACCCAGTCAC CGTGGCCTCC AACCTGCAG                               459

(2) INFORMATION FOR SEQ ID NO:134:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:134:

GCCGACGAGG AGCTCTGCGG GGGCCTCTGG CGGCTGGTCC TGGCACAGCG CTGGATGGAG         60

CGGCTCAAGA CTGTCGCTGG GTCCAAGATG CAAGGCTTGC TGGAGCGCGT GAACACGGAG        120
```

```
ATACACTTTG TCACCAAATG TGCCTTTCAG CCCCCCCCCA GCTGTCTTCG CTTCGTCCAG       180

ACCAACATCT CCCGCCTCCT GCAGGAGACC TCCGAGCAGC TGGTGGCGCT GAAGCCCTGG       240

ATCACTCGCC AGAACTTCTC CCGGTGCCTG GAGCTGCAGT GTCAGCCCGA CTCCTCAACC       300

CTGGGCGGTG GGTCAGGAGG TGGGTCAGGA GGTGGATCCG GAGGTGGCAC CCAGGACTGC       360

TCCTTCCAAC ACAGCCCCAT CTCCTCCGAC TTCGCTGTCA AAATCCGTGA GCTGTCTGAC       420

TACCTGCTTC AAGATTACCC AGTCACCGTG GCCTCCAACC TGCAG                      465
```

(2) INFORMATION FOR SEQ ID NO:135:

(i) SEQUENCE CHARACTERISTICS:
        (A) LENGTH: 483 base pairs
        (B) TYPE: nucleic acid
        (C) STRANDEDNESS: single
        (D) TOPOLOGY: linear (xi) SEQUENCE DESCRIPTION: SEQ ID NO:135:

```
GCCGACGAGG AGCTCTGCGG GGGCCTCTGG CGGCTGGTCC TGGCACAGCG CTGGATGGAG        60

CGGCTCAAGA CTGTCGCTGG GTCCAAGATG CAAGGCTTGC TGGAGCGCGT GAACACGGAG       120

ATACACTTTG TCACCAAATG TGCCTTTCAG CCCCCCCCCA GCTGCCTTCG CTTCGTCCAG       180

ACCAACATCT CCCGCCTCCT GCAGGAGACC TCCGAGCAGC TGGTGGCGCT GAAGCCCTGG       240

ATCACTCGCC AGAACTTCTC CCGGTGCCTG GAGCTGCAGT GTCAGCCCGA CTCCTCAACC       300

CTGGGCGGTG GGTCAGGAGG TGGGTCAGGA GGTGGATCCG GAGGTGGCTC AGGGGGAGGT       360

AGTGGTACCC AGGACTGCTC CTTCCAACAC AGCCCCATCT CCTCCGACTT CGCTGTCAAA       420

ATCCGTGAGC TGTCTGACTA CCTGCTTCAA GATTACCCAG TCACCGTGGC CTCCAACCTG       480

CAG                                                                    483
```

(2) INFORMATION FOR SEQ ID NO:136:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:136:

```
GCCGATTACC CAGTCACCGT GGCCTCCAAC CTGCAGGACG AGGAGCTCTG CGGGGGCCTC        60

TGGCGGCTGG TCCTGGCACA GCGCTGGATG GAGCGGCTCA AGACTGTCGC TGGGTCCAAG       120

ATGCAAGGCT TGCTGGAGCG CGTGAACACG GAGATACACT TTGTCACCAA ATGTGCCTTT       180

CAGCCCCCCC CCAGCTGTCT TCGCTTCGTC CAGACCAACA TCTCCCGCCT CCTGCAGGAG       240

ACCTCCGAGC AGCTGGTGGC GCTGAAGCCC TGGATCACTC GCCAGAACTT CTCCCGGTGC       300

CTGGAGCTGC AGTGTCAGCC CGACTCCTCA ACCCTGGGCG GTGGGTCAGG AGGTGGGTCA       360

GGAGGTGGAT CCGGAGGTGG CACCCAGGAC TGCTCCTTCC AACACAGCCC CATCTCCTCC       420

GACTTCGCTG TCAAAATCCG TGAGCTGTCT GACTACCTGC TTCAA                      465
```

(2) INFORMATION FOR SEQ ID NO:137:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:137:

−continued

```
GCCGCCTCCA ACCTGCAGGA CGAGGAGCTC TGCGGGGGCC TCTGGCGGCT GGTCCTGGCA    60

CAGCGCTGGA TGGAGCGGCT CAAGACTGTC GCTGGGTCCA AGATGCAAGG CTTGCTGGAG   120

CGCGTGAACA CGGAGATACA CTTTGTCACC AAATGTGCCT TTCAGCCCCC CCCCAGCTGT   180

CTTCGCTTCG TCCAGACCAA CATCTCCCGC CTCCTGCAGG AGACCTCCGA GCAGCTGGTG   240

GCGCTGAAGC CCTGGATCAC TCGCCAGAAC TTCTCCCGGT GCCTGGAGCT GCAGTGTCAG   300

CCCGACTCCT CAACCCTGGG CGGTGGGTCA GGAGGTGGGT CAGGAGGTGG ATCCGGAGGT   360

GGCACCCAGG ACTGCTCCTT CCAACACAGC CCCATCTCCT CCGACTTCGC TGTCAAAATC   420

CGTGAGCTGT CTGACTACCT GCTTCAAGAT TACCCAGTCA CCGTG                   465
```

(2) INFORMATION FOR SEQ ID NO:138:

(i) SEQUENCE CHARACTERISTICS:
  (A) LENGTH: 465 base pairs
  (B) TYPE: nucleic acid
  (C) STRANDEDNESS: single
  (D) TOPOLOGY: linear (xi) SEQUENCE DESCRIPTION: SEQ ID NO:138:

```
GCCGTCGCTG GGTCCAAGAT GCAAGGCTTG CTGGAGCGCG TGAACACGGA GATACACTTT    60

GTCACCAAAT GTGCCTTTCA GCCCCCCCCC AGCTGTCTTC GCTTCGTCCA GACCAACATC   120

TCCCGCCTCC TGCAGGAGAC CTCCGAGCAG CTGGTGGCGC TGAAGCCCTG GATCACTCGC   180

CAGAACTTCT CCCGGTGCCT GGAGCTGCAG TGTCAGCCCG ACTCCTCAAC CCTGGGCGGT   240

GGGTCAGGAG GTGGGTCAGG AGGTGGATCC GGAGGTGGCA CCCAGGACTG CTCCTTCCAA   300

CACAGCCCCA TCTCCTCCGA CTTCGCTGTC AAAATCCGTG AGCTGTCTGA CTACCTGCTT   360

CAAGATTACC CAGTCACCGT GGCCTCCAAC CTGCAGGACG AGGAGCTCTG CGGGGGCCTC   420

TGGCGGCTGG TCCTGGCACA GCGCTGGATG GAGCGGCTCA AGACT                   465
```

(2) INFORMATION FOR SEQ ID NO:139:

(i) SEQUENCE CHARACTERISTICS:
  (A) LENGTH: 465 base pairs
  (B) TYPE: nucleic acid
  (C) STRANDEDNESS: single
  (D) TOPOLOGY: linear (xi) SEQUENCE DESCRIPTION: SEQ ID NO:139:

```
GCCTCCAAGA TGCAAGGCTT GCTGGAGCGC GTGAACACGG AGATACACTT TGTCACCAAA    60

TGTGCCTTTC AGCCCCCCCC CAGCTGTCTT CGCTTCGTCC AGACCAACAT CTCCCGCCTC   120

CTGCAGGAGA CCTCCGAGCA GCTGGTGGCG CTGAAGCCCT GGATCACTCG CCAGAACTTC   180

TCCCGGTGCC TGGAGCTGCA GTGTCAGCCC GACTCCTCAA CCCTGGGCGG TGGGTCAGGA   240

GGTGGGTCAG GAGGTGGATC CGGAGGTGGC ACCCAGGACT GCTCCTTCCA ACACAGCCCC   300

ATCTCCTCCG ACTTCGCTGT CAAAATCCGT GAGCTGTCTG ACTACCTGCT TCAAGATTAC   360

CCAGTCACCG TGGCCTCCAA CCTGCAGGAC GAGGAGCTCT GCGGGGGCCT CTGGCGGCTG   420

GTCCTGGCAC AGCGCTGGAT GGAGCGGCTC AAGACTGTCG CTGGG                   465
```

(2) INFORMATION FOR SEQ ID NO:140:

(i) SEQUENCE CHARACTERISTICS:
  (A) LENGTH: 465 base pairs
  (B) TYPE: nucleic acid
  (C) STRANDEDNESS: single
  (D) TOPOLOGY: linear (xi) SEQUENCE DESCRIPTION: SEQ ID NO:140:

| | | | | | |
|---|---|---|---|---|---|
| GCCCCCCCCA | GCTGTCTTCG | CTTCGTCCAG | ACCAACATCT | CCCGCCTCCT | GCAGGAGACC | 60
| TCCGAGCAGC | TGGTGGCGCT | GAAGCCCTGG | ATCACTCGCC | AGAACTTCTC | CCGGTGCCTG | 120
| GAGCTGCAGT | GTCAGCCCGA | CTCCTCAACC | CTGGGCGGTG | GGTCAGGAGG | TGGGTCAGGA | 180
| GGTGGATCCG | GAGGTGGCAC | CCAGGACTGC | TCCTTCCAAC | ACAGCCCCAT | CTCCTCCGAC | 240
| TTCGCTGTCA | AAATCCGTGA | GCTGTCTGAC | TACCTGCTTC | AAGATTACCC | AGTCACCGTG | 300
| GCCTCCAACC | TGCAGGACGA | GGAGCTCTGC | GGGGGCCTCT | GGCGGCTGGT | CCTGGCACAG | 360
| CGCTGGATGG | AGCGGCTCAA | GACTGTCGCT | GGGTCCAAGA | TGCAAGGCTT | GCTGGAGCGC | 420
| GTGAACACGG | AGATACACTT | TGTCACCAAA | TGTGCCTTTC | AGCCC | | 465

(2) INFORMATION FOR SEQ ID NO:141:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:141:

| | | | | | |
|---|---|---|---|---|---|
| GCCCGCTTCG | TCCAGACCAA | CATCTCCCGC | CTCCTGCAGG | AGACCTCCGA | GCAGCTGGTG | 60
| GCGCTGAAGC | CCTGGATCAC | TCGCCAGAAC | TTCTCCCGGT | GCCTGGAGCT | GCAGTGTCAG | 120
| CCCGACTCCT | CAACCCTGGG | CGGTGGGTCA | GGAGGTGGGT | CAGGAGGTGG | ATCCGGAGGT | 180
| GGCACCCAGG | ACTGCTCCTT | CCAACACAGC | CCCATCTCCT | CCGACTTCGC | TGTCAAAATC | 240
| CGTGAGCTGT | CTGACTACCT | GCTTCAAGAT | TACCCAGTCA | CCGTGGCCTC | CAACCTGCAG | 300
| GACGAGGAGC | TCTGCGGGGG | CCTCTGGCGG | CTGGTCCTGG | CACAGCGCTG | GATGGAGCGG | 360
| CTCAAGACTG | TCGCTGGGTC | CAAGATGCAA | GGCTTGCTGG | AGCGCGTGAA | CACGGAGATA | 420
| CACTTTGTCA | CCAAATGTGC | CTTTCAGCCC | CCCCCAGCT | GTCTT | | 465

(2) INFORMATION FOR SEQ ID NO:142:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (xi) SEQUENCE DESCRIPTION: SEQ ID NO:142:

| | | | | | |
|---|---|---|---|---|---|
| GCCACCAACA | TCTCCCGCCT | CCTGCAGGAG | ACCTCCGAGC | AGCTGGTGGC | GCTGAAGCCC | 60
| TGGATCACTC | GCCAGAACTT | CTCCCGGTGC | CTGGAGCTGC | AGTGTCAGCC | CGACTCCTCA | 120
| ACCCTGGGCG | GTGGGTCAGG | AGGTGGGTCA | GGAGGTGGAT | CCGGAGGTGG | CACCCAGGAC | 180
| TGCTCCTTCC | AACACAGCCC | CATCTCCTCC | GACTTCGCTG | TCAAAATCCG | TGAGCTGTCT | 240
| GACTACCTGC | TTCAAGATTA | CCCAGTCACC | GTGGCCTCCA | ACCTGCAGGA | CGAGGAGCTC | 300
| TGCGGGGGCC | TCTGGCGGCT | GGTCCTGGCA | CAGCGCTGGA | TGGAGCGGCT | CAAGACTGTC | 360
| GCTGGGTCCA | AGATGCAAGG | CTTGCTGGAG | CGCGTGAACA | CGGAGATACA | CTTTGTCACC | 420
| AAATGTGCCT | TTCAGCCCCC | CCCCAGCTGT | CTTCGCTTCG | TCCAG | | 465

(2) INFORMATION FOR SEQ ID NO:143:

(i) SEQUENCE CHARACTERISTICS:
        (A) LENGTH: 134 amino acids
        (B) TYPE: amino acid (C) STRANDEDNESS: single
        (D) TOPOLOGY: linear (ii) MOLECULE TYPE: None (xi) SEQUENCE DESCRIPTION: SEQ ID NO:143:

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

Glu Leu Gln Cys Gln Pro
    130

(2) INFORMATION FOR SEQ ID NO:144:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:144:

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu
    130                 135

(2) INFORMATION FOR SEQ ID NO:145:

(i) SEQUENCE CHARACTERISTICS:
        (A) LENGTH: 209 amino acids (B) TYPE: amino acid
            (C) STRANDEDNESS: single
            (D) TOPOLOGY: linear (ii) MOLECULE TYPE: None (xi) SEQUENCE DESCRIPTION: SEQ ID NO:145:

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
        50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
        130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
                180                 185                 190

Glu Gln Val Pro Pro Val Pro Ser Pro Gln Asp Leu Leu Leu Val Glu
            195                 200                 205

His (2) INFORMATION FOR SEQ ID NO:146:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO:146:

ACCCAGGACT GCTCCTTCCA ACACAGCCCC ATCTCCTCCG ACTTCGCTGT CAAAATCCGT      60

GAGCTGTCTG ACTACCTGCT TCAAGATTAC CCAGTCACCG TGGCCTCCAA CCTGCAGGAC     120

GAGGAGCTCT GCGGGGGCCT CTGGCGGCTG GTCCTGGCAC AGCGCTGGAT GGAGCGGCTC     180

AAGACTGTCG CTGGGTCCAA GATGCAAGGC TTGCTGGAGC GCGTGAACAC GGAGATACAC     240

TTTGTCACCA AATGTGCCTT TCAGCCCCCC CCCAGCTGTC TTCGCTTCGT CCAGACCAAC     300

ATCTCCCGCC TCCTGCAGGA GACCTCCGAG CAGCTGGTGG CGCTGAAGCC CTGGATCACT     360

CGCCAGAACT TCTCCCGGTG CCTGGAGCTG CAGTGTCAGC CC                        402

(2) INFORMATION FOR SEQ ID NO:147:

(i) SEQUENCE CHARACTERISTICS:
        (A) LENGTH: 630 base pairs (B) TYPE: nucleic acid
        (C) STRANDEDNESS: single
        (D) TOPOLOGY: linear (xi) SEQUENCE DESCRIPTION: SEQ ID NO:147:

ACCCAGGACT GCTCCTTCCA ACACAGCCCC ATCTCCTCCG ACTTCGCTGT CAAAATCCGT      60

GAGCTGTCTG ACTACCTGCT TCAAGATTAC CCAGTCACCG TGGCCTCCAA CCTGCAGGAC     120

GAGGAGCTCT GCGGGGGCCT CTGGCGGCTG GTCCTGGCAC AGCGCTGGAT GGAGCGGCTC     180

AAGACTGTCG CTGGGTCCAA GATGCAAGGC TTGCTGGAGC GCGTGAACAC GGAGATACAC     240

TTTGTCACCA AATGTGCCTT TCAGCCCCCC CCCAGCTGTC TTCGCTTCGT CCAGACCAAC     300

ATCTCCCGCC TCCTGCAGGA GACCTCCGAG CAGCTGGTGG CGCTGAAGCC CTGGATCACT     360

CGCCAGAACT TCTCCCGGTG CCTGGAGCTG CAGTGTCAGC CCGACTCCTC AACCCTGCCA     420

CCCCCATGGA GTCCCCGGCC CCTGGAGGCC ACAGCCCCGA CAGCCCCGCA GCCCCCTCTG     480

CTCCTCCTAC TGCTGCTGCC CGTGGGCCTC CTGCTGCTGG CCGCTGCCTG GTGCCTGCAC     540

TGGCAGAGGA CGCGGCGGAG GACACCCCGC CCTGGGGAGC AGGTGCCCCC CGTCCCCAGT     600

CCCCAGGACC TGCTGCTTGT GGAGCACTGA                                     630

(2) INFORMATION FOR SEQ ID NO:148:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:148:

Gly Gly Gly Ser Gly Gly Gly Ser Gly Gly Gly Ser Gly Gly Gly Ser
 1               5                  10                  15

Gly Gly Gly Ser Gly Gly Gly Ser Gly Gly Gly Ser Gly
            20                  25

(2) INFORMATION FOR SEQ ID NO:149:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:149:

Pro Pro Pro Trp Ser Pro Arg Pro Leu Gly Ala Thr Ala Pro Thr Ala
 1               5                  10                  15

Gly Gln Pro Pro Leu
            20

(2) INFORMATION FOR SEQ ID NO:150:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:150:

Pro Pro Pro Trp Ser Pro Arg Pro Leu Gly Ala Thr Ala Pro Thr
 1               5                  10                  15

(2) INFORMATION FOR SEQ ID NO:151:

(i) SEQUENCE CHARACTERISTICS:
    (A) LENGTH: 16 amino acids
    (B) TYPE: amino acid
    (C) STRANDEDNESS: single
    (D) TOPOLOGY: linear (xi) SEQUENCE DESCRIPTION: SEQ ID NO:151:

Val Glu Thr Val Phe His Arg Val Ser Gln Asp Gly Leu Leu Thr Ser
 1               5                  10                  15